(12) United States Patent
Ballinger et al.

(10) Patent No.: US 11,995,828 B2
(45) Date of Patent: May 28, 2024

(54) DENSLEY-PACKED ANALYTE LAYERS AND DETECTION METHODS

(71) Applicant: Pacific Biosciences of California, Inc., Menlo Park, CA (US)

(72) Inventors: Dennis Ballinger, Pleasanton, CA (US); Norman Burns, Pleasanton, CA (US); Manohar Furtado, Pleasanton, CA (US); Niandong Liu, Pleasanton, CA (US); Windsor Owens, Pleasanton, CA (US); Bryan Staker, Pleasanton, CA (US)

(73) Assignee: PACIFIC BIOSCIENCES OF CALIFORNIA, INC., Menlo Park, CA (US)

( * ) Notice: Subject to any disclaimer, the term of this patent is extended or adjusted under 35 U.S.C. 154(b) by 0 days.

(21) Appl. No.: 18/052,880

(22) Filed: Nov. 4, 2022

(65) Prior Publication Data

US 2024/0005488 A1    Jan. 4, 2024

Related U.S. Application Data

(63) Continuation of application No. 17/204,795, filed on Mar. 17, 2021, now abandoned, which is a
(Continued)

(51) Int. Cl.
*G06T 7/174* (2017.01)
*C12Q 1/6816* (2018.01)
(Continued)

(52) U.S. Cl.
CPC .......... *G06T 7/0012* (2013.01); *C12Q 1/6816* (2013.01); *G06T 7/174* (2017.01); *G06T 7/70* (2017.01); *G06T 2207/30072* (2013.01)

(58) Field of Classification Search
None
See application file for complete search history.

(56) References Cited

U.S. PATENT DOCUMENTS

| 4,987,065 | A | * | 1/1991 | Stavrianopoulos | .... C12N 15/00 |
| | | | | | 435/6.12 |
| 5,302,509 | A | * | 4/1994 | Cheeseman | .......... C12Q 1/6869 |
| | | | | | 536/25.3 |

(Continued)

FOREIGN PATENT DOCUMENTS

| BY | 4655 | 9/2002 |
| CN | 1584592 A | 2/2005 |

(Continued)

OTHER PUBLICATIONS

Babcock et al., A high-density 3D localization algorithm for stochastic optical reconstruction microscopy. Optical Nanoscopy vol. 1, Article No. 6 (2012).
(Continued)

*Primary Examiner* — Tsung Yin Tsai
(74) *Attorney, Agent, or Firm* — Wilson Sonsini Goodrich & Rosati

(57) ABSTRACT

Disclosed herein are methods and systems for detection and discrimination of optical signals from a densely packed substrate. These have broad applications for biomolecule detection near or below the diffraction limit of optical systems, including in improving the efficiency and accuracy of polynucleotide sequencing applications.

11 Claims, 39 Drawing Sheets

Specification includes a Sequence Listing.

Related U.S. Application Data continuation of application No. PCT/US2019/051796, filed on Sep. 18, 2019.

(60) Provisional application No. 62/733,525, filed on Sep. 19, 2018.

(51) Int. Cl.
   *G06T 7/00* (2017.01)
   *G06T 7/70* (2017.01)

(56) References Cited

U.S. PATENT DOCUMENTS

| | | | |
|---|---|---|---|
| 5,494,810 A | 2/1996 | Barany et al. | |
| 5,763,594 A | 6/1998 | Hiatt et al. | |
| 6,103,474 A | 8/2000 | Dellinger et al. | |
| 6,214,987 B1 | 4/2001 | Hiatt et al. | |
| 6,232,465 B1 | 5/2001 | Hiatt et al. | |
| 6,654,505 B2 | 11/2003 | Bridgham et al. | |
| 6,852,487 B1 | 2/2005 | Barany et al. | |
| 7,057,026 B2 | 6/2006 | Barnes et al. | |
| 7,122,319 B2 | 10/2006 | Liu et al. | |
| 7,769,548 B2 | 8/2010 | Garcia | |
| 7,838,302 B2 | 11/2010 | Zhuang et al. | |
| 7,948,015 B2 | 5/2011 | Rothberg et al. | |
| 7,960,104 B2 | 6/2011 | Drmanac et al. | |
| 8,149,418 B2 | 4/2012 | Tearney et al. | |
| 8,158,346 B2 | 4/2012 | Balasubramanian et al. | |
| 8,175,452 B1 | 5/2012 | Staker et al. | |
| 8,218,834 B2 | 7/2012 | Homman et al. | |
| 8,428,454 B2 | 4/2013 | Staker et al. | |
| 8,676,013 B2 | 3/2014 | Bouma et al. | |
| 9,193,998 B2 | 11/2015 | Khurana et al. | |
| 9,551,026 B2 | 1/2017 | Fernandez et al. | |
| 10,378,053 B2 | 8/2019 | Staker et al. | |
| 10,510,435 B2 | 12/2019 | Cai et al. | |
| 10,829,816 B2 | 11/2020 | Staker et al. | |
| 10,901,230 B2 | 1/2021 | Skinner et al. | |
| 11,047,005 B2 | 6/2021 | Staker et al. | |
| 11,060,140 B2 | 7/2021 | Staker et al. | |
| 11,248,266 B2 | 2/2022 | Staker et al. | |
| 11,434,532 B2 * | 9/2022 | Staker | G06T 7/73 |
| 11,650,202 B2 * | 5/2023 | Staker | G01N 33/582 |
| | | | 506/18 |
| 2002/0028519 A1 | 3/2002 | Yguerabide et al. | |
| 2002/0086322 A1 | 7/2002 | Yu et al. | |
| 2003/0118595 A1 | 6/2003 | Niemeyer et al. | |
| 2003/0207300 A1 | 11/2003 | Matray et al. | |
| 2003/0215862 A1 | 11/2003 | Parce et al. | |
| 2004/0191794 A1 | 9/2004 | Weindel et al. | |
| 2005/0049796 A1 | 3/2005 | Webb et al. | |
| 2005/0148100 A1 | 7/2005 | Su et al. | |
| 2005/0153320 A1 | 7/2005 | Herron et al. | |
| 2005/0250094 A1 | 11/2005 | Storhoff et al. | |
| 2006/0275782 A1 | 12/2006 | Gunderson et al. | |
| 2007/0072208 A1 | 3/2007 | Drmanac | |
| 2007/0087382 A1 | 4/2007 | Howorka et al. | |
| 2008/0018898 A1 | 1/2008 | Gunstream et al. | |
| 2008/0161194 A1 | 7/2008 | Turner et al. | |
| 2009/0017271 A1 | 1/2009 | Meiring et al. | |
| 2009/0081688 A1 | 3/2009 | Luo et al. | |
| 2009/0317810 A1 | 12/2009 | Lofton-Day et al. | |
| 2010/0075407 A1 | 3/2010 | Duffy et al. | |
| 2010/0301398 A1 | 12/2010 | Rothberg et al. | |
| 2011/0009296 A1 | 1/2011 | Kain et al. | |
| 2011/0071048 A1 | 3/2011 | Oshima | |
| 2011/0165559 A1 | 7/2011 | Lane et al. | |
| 2012/0020537 A1 | 1/2012 | Garcia et al. | |
| 2012/0052490 A1 | 3/2012 | Eid et al. | |
| 2012/0226653 A1 | 9/2012 | McLaughlin et al. | |
| 2012/0307121 A1 | 12/2012 | Lu et al. | |
| 2012/0330567 A1 | 12/2012 | Bauer et al. | |
| 2013/0045872 A1 | 2/2013 | Zhou et al. | |
| 2013/0053256 A1 | 2/2013 | Hubbell | |
| 2013/0059740 A1 | 3/2013 | Drmanac et al. | |
| 2013/0124100 A1 | 5/2013 | Drmanac et al. | |
| 2013/0265459 A1 | 10/2013 | Duparre et al. | |
| 2014/0194311 A1 | 7/2014 | Gullberg et al. | |
| 2014/0226881 A1 | 8/2014 | Piestun et al. | |
| 2014/0287468 A1 | 9/2014 | Richard | |
| 2015/0152473 A1 | 6/2015 | Nadeau et al. | |
| 2015/0267251 A1 | 9/2015 | Cai et al. | |
| 2015/0330974 A1 * | 11/2015 | Staker | G01N 33/582 |
| | | | 506/18 |
| 2016/0003809 A1 | 1/2016 | Dunaway | |
| 2016/0201119 A1 | 7/2016 | Staker et al. | |
| 2017/0152554 A1 | 6/2017 | Drmanac et al. | |
| 2017/0220733 A1 | 8/2017 | Zhuang et al. | |
| 2018/0023124 A1 | 1/2018 | Collins et al. | |
| 2018/0274028 A1 * | 9/2018 | Staker | G16B 30/00 |
| 2019/0276886 A1 | 9/2019 | Skinner et al. | |
| 2019/0284552 A1 | 9/2019 | Collins et al. | |
| 2019/0323080 A1 | 10/2019 | Staker et al. | |
| 2019/0353887 A1 | 11/2019 | Riza | |
| 2020/0063200 A1 | 2/2020 | Staker et al. | |
| 2020/0140933 A1 | 5/2020 | Staker et al. | |
| 2020/0217850 A1 | 7/2020 | Liu et al. | |
| 2020/0393691 A1 | 12/2020 | Owens et al. | |
| 2021/0072233 A1 * | 3/2021 | Staker | G01N 33/582 |
| 2021/0277469 A1 * | 9/2021 | Staker | G06T 7/73 |

FOREIGN PATENT DOCUMENTS

| | | |
|---|---|---|
| CN | 1653480 A | 8/2005 |
| CN | 101865843 A | 10/2010 |
| CN | 101865843 B | 5/2012 |
| CN | 107735497 A | 2/2018 |
| CN | 110031907 A | 7/2019 |
| EP | 1388587 A4 | 12/2006 |
| EP | 2251435 A1 | 11/2010 |
| EP | 2620510 A1 | 7/2013 |
| EP | 3595806 A1 | 1/2020 |
| JP | 2002524739 A | 8/2002 |
| JP | 2007536528 A | 12/2007 |
| JP | 2008249711 A | 10/2008 |
| JP | 2010500563 A | 1/2010 |
| JP | 2014164004 A | 9/2014 |
| JP | 2017504039 A | 2/2017 |
| KR | 20160048714 A | 5/2016 |
| WO | WO-9511461 A1 | 4/1995 |
| WO | WO-9967641 A2 | 12/1999 |
| WO | WO-9967641 A3 | 3/2000 |
| WO | WO-2005113817 A9 | 8/2006 |
| WO | WO-2007097754 A1 | 8/2007 |
| WO | WO-2008033167 A2 | 3/2008 |
| WO | WO-2008091296 A2 | 7/2008 |
| WO | WO-2009097626 A2 | 8/2009 |
| WO | WO-2011137183 A1 | 11/2011 |
| WO | WO-2012031011 A1 | 3/2012 |
| WO | WO-2014015269 A1 | 1/2014 |
| WO | WO-2014078855 A1 | 5/2014 |
| WO | WO-2014137474 A1 | 9/2014 |
| WO | WO-2015027112 A1 | 2/2015 |
| WO | WO-2015104245 A1 | 7/2015 |
| WO | WO-2016074338 A1 | 5/2016 |
| WO | WO-2016134191 A1 | 8/2016 |
| WO | WO-2016156845 A1 | 10/2016 |
| WO | WO-2017079573 A1 | 5/2017 |
| WO | WO-2017079593 A1 | 5/2017 |
| WO | WO-2017123770 A1 | 7/2017 |
| WO | WO-2017161251 A1 | 9/2017 |
| WO | WO-2017196527 A1 | 11/2017 |
| WO | WO-2017223041 A1 | 12/2017 |
| WO | WO-2018161013 A1 | 9/2018 |
| WO | WO-2018170518 A1 | 9/2018 |
| WO | WO-2018175402 A1 | 9/2018 |

OTHER PUBLICATIONS

Bentley et al. Accurate whole human genome sequencing using reversible terminator chemistry. Nature 456(7218):53-59 (2008).
CAS Registry No. 361411-90-7 (entered into database 2001) (Year: 2001).

(56) References Cited

OTHER PUBLICATIONS

Chai J, et al. Single-molecule protein arrays enabled by scanning probe block copolymer lithography. Proc Natl Acad Sci U S A. Dec. 6, 2011;108(49):19521-5. Epub Nov. 21, 2011.
Cho et al. Optimization of Aptamer Microarray Technology for Multiple Protein Targets. Analytica Chimica Acta 564(1):82-90 (2006).
Dai et al., Optical imaging of individual biomolecules in densely packed clusters. Nature Nanotechnology 11: 798-807 (2016).
Drmanac et al. Human Genome Sequencing Using Unchained Base Reads on Self-Assembling DNA nanoarrays. Science Reports, 327:78-81 (Jan. 1, 2010).
Extended European Search Report issued in European Patent Application No. 19861989.2 dated May 19, 2022.
Gavrilovic et al. Quantification of Colocalization and Cross-Tk Based on Spectral Angles. J Microsc 324(3):311-324 (2009).
Gu et al.: Multiplex single-molecule interaction profiling of DNA-barcoded proteins. Nature 515:54-557 and Supplementary Information, entire document 2014.
Gunderson et al.: Decoding randomly ordered DNA arrays. Genome Research 14(5):870-877 (2004).
Guo et al. Four-color DNA sequencing with 3'-O-modified nucleotide reversible terminators and chemically cleavable fluorescent dideoxynucleotides. PNAS USA 105(27):9145-9150 (2008).
Guo et al. Supporting Information for Four-color DNA sequencing with 3'-O-modified nucleotide reversible terminators and chemically cleavable fluorescent dideoxynucleotides. PNAS USA PNAS USA 105(27):9145-9150 (2008).
Hager et al. Arrays of Individual DNA Molecules on Nanopatterned Substrates. Scientific Reports 7:42075 (2017).
Illumina Sequencing Technology, Technology Spotlight: Illumina® Sequencing, Illumina, Inc. (2010).
Ju et al.: Four-Color DNA Sequencing by Synthesis Using Cleavable Fluorescent Nucleotide Reversible Terminators. PNAS USA 103:19635-19640 (2006).
Kao et al. BayesCall: A Model-Based Base-Cling algorithm for High-Throughput Short-Read Sequencing. Genome Research 19:1884-1895 (2009).
Kozlov, et al. Efficient strategies for the conjugation of oligonucleotides to antibodies enabling highly sensitive protein detection. Biopolymers. Apr. 5, 2004;73(5):621-30.
Kumar et al. PEG-Labeled Nucleotides and Nanopore Detection for Single Molecule DNA Sequencing by Synthesis. Scientific Reports 2:1-8 (2012).
Lee et al., Ion-sensitive field-effect transistor for biological sensing. Sensors. 9(9):7111-7131 (2009).
Levene et al., Zero-mode waveguides for single-molecule analysis at high concentrations. Science. 299(5607)682-686 (2003).
Levy et al. Advancements in Next-Generation Sequencing. Annu Rev Genomics Hum Genet 17:95-115 (2016).
Liu et al. Comparison of Next-Generation Sequencing Systems. J Biomed Biotechnol 2012: 251364 (2012).
Moerner, et al., Methods of single-molecule fluorescence spectroscopy and microscopy. Review of Scientific Instruments. 74(8):3597-3619 (2003).
Mukamel et al., Statistical deconvolution for superresolution fluorescence microscopy. Biophys J 102(10):2391-2400 (2012).
Munck et al., Sub-diffraction imaging on standard microscopes through photobleaching microscopy with non-linear processing. J Cell Sci 125(Pt 9):2257-2266 (2012).
Office Action and Translation issued in Chinese Patent Application No. 2019800762595 dated May 17, 2022.
PCT/US2013/070797 International Search Report and Written Opinion dated Feb. 21, 2014.
PCT/US2018/023187 International Search Report and Written Opinion dated May 31, 2018.
PCT/US2018/023310 International Search Report and Written Opinion dated Sep. 4, 2018.
PCT/US2018/051183 International Search Report and Written Opinion dated Jan. 18, 2019.
PCT/US2019/015243 International Search Report and Written Opinion dated Mar. 22, 2019.
PCT/US2019/051796 International Search Report and Written Opinion dated Jan. 3, 2020.
Ramanathan et al., An integrative approach for the optical sequencing of single DNA molecules. Analytical Biochemistry 330(2):227-241 (2004).
Riley et al. Reed-Solomon Codes. https://www.cs.cmu.edu/-guyb/realworld/reedsolomon/reedsolomoncodes.html (1996).
Rotman, B., Measurement of activity of single molecules of beta-D-galactosidase. Proceedings of the National Academy of Sciences of the United States of America. 47:1981-1991 (1961).
Small et al., Fluorophore localization algorithms for super-resolution microscopy. Nature Methods 11: 267-279 (2014).
Song et al., Aptamer-based biosensors, TrAC Trends in Analytical Chemistry. 27(2):108-117 (2008).
Svobodova et al., Comparison of Different Methods for Generation of Single-Stranded DNA for SELEX Processes. Anal Bioanal Chem 404(3): 835-842 (2012).
TUERK. Systematic evolution of ligands by exponential enrichment: RNA ligands to bacteriophage T4 DNA polymerase. Science 249:505-510 (1990).
U.S. Appl. No. 16/458,977 Non-Final Office Action dated Jan. 22, 2021.
U.S. Appl. No. 16/572,535 Non-Final Office Action dated Mar. 30, 2020.
U.S. Appl. No. 17/204,795 Non-Final Office Action dated Oct. 25, 2021.
U.S. Appl. No. 17/084,017 Office Action dated Feb. 2, 2021.
U.S. Appl. No. 14/443,655 Office Action dated Jun. 12, 2018.
U.S. Appl. No. 14/443,655 Office Action dated Jun. 25, 2019.
U.S. Appl. No. 14/443,655 Office Action dated Mar. 9, 2017.
U.S. Appl. No. 14/443,655 Office Action dated Nov. 14, 2016.
U.S. Appl. No. 14/443,655 Office Action dated Oct. 18, 2017.
U.S. Appl. No. 14/912,883 Office Action dated Apr. 3, 2019.
U.S. Appl. No. 15/925,656 Office Action dated Sep. 27, 2018.
Wang et al., An adaptive decorrelation method removes Illumina DNA base-calling errors caused by crosstalk between adjacent clusters. Scientific Reports vol. 7, Article No. 41348 (2017).
Wang et al., Sub-diffraction limit localization of proteins in volumetric space using Bayesian restoration of fluorescence images from ultrathin specimens. PLoS Comput Biol 8(8):e1002671 (2012).

* cited by examiner

| Parameter | Unit | Case 1 | Case 2 | Case 3 | Case 4 | Case 5 | Case 6 |
|---|---|---|---|---|---|---|---|
| *Inputs* | | | | | | | |
| Pitch | nm | 220 | 236 | 261 | 200 | 250 | 333 |
| # Molecules / um^2 | NA | 20.7 | 17.9 | 14.7 | 25.0 | 16.0 | 9.0 |
| # Cycles | NA | 100 | 100 | 100 | 100 | 100 | 100 |
| Lane width | mm | 63 | 63 | 63 | 63 | 63 | 63 |
| Lane length | mm | 63 | 63 | 63 | 63 | 63 | 63 |
| Frame rate | Hz | 85 | 85 | 85 | 85 | 85 | 85 |
| *Outputs* | | | | | | | |
| Throughput (30X genome) | per run | 90 | 78 | 64 | 109 | 70 | 39 |
| Throughput (30X genome) | per day | 93 | 81 | 66 | 113 | 72 | 41 |
| Throughput (Gb) | per run | 8,127 | 7,044 | 5,785 | 9,838 | 6,297 | 3,542 |
| Throughput (Gb) | per day | 8,398 | 7,280 | 5,978 | 10,167 | 6,507 | 3,660 |
| # Spots / chip | 10^9 | 81.3 | 70.4 | 57.9 | 98.4 | 63.0 | 35.4 |
| Imaging time per cycle | min | 13.9 | 13.9 | 13.9 | 13.9 | 13.9 | 13.9 |

Figure 1

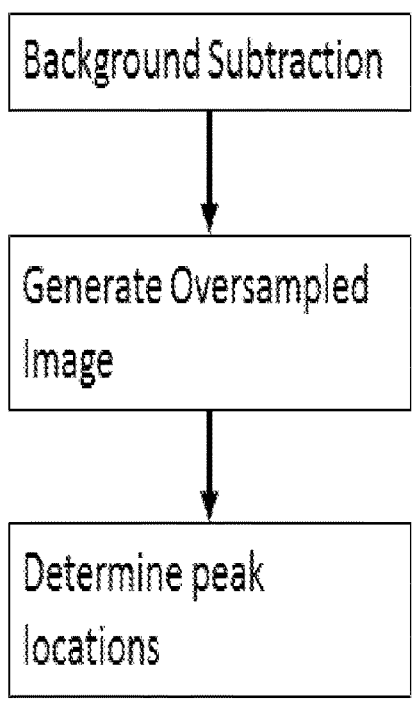
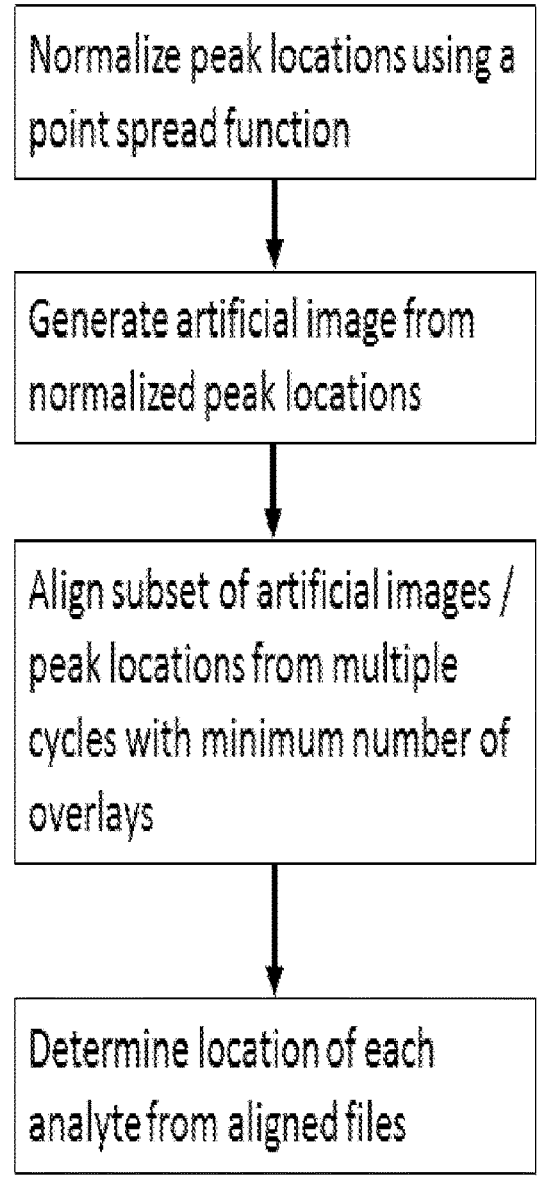
Figure 10A
Figure 10B

4-Color Composite

Case #1A

Case #4A

DENSLEY-PACKED ANALYTE LAYERS AND DETECTION METHODS

CROSS-REFERENCE

This application is a continuation of Ser. No. 17/204,795, filed Mar. 17, 2021, which is a continuation of PCT/US2019/051796, filed Sep. 18, 2019, which claims priority to U.S. Provisional Patent Application No. 62/733,525 filed Sep. 19, 2018, which are incorporated herein by reference in their entireties.

SEQUENCE LISTING

The instant application contains a Sequence Listing which has been submitted electronically in XML format and is hereby incorporated by reference in its entirety. Said XML copy, created on Sep. 15, 2023, is named 55495-808_302_SL.xml and is 11,829 bytes in size.

BACKGROUND

Affordable, rapid sequencing is causing a revolution in medicine and healthcare globally. As price of a genome has dropped dramatically since the first human genome was sequenced in year 2000, a significant milestone, $1,000 genome, was recently achieved. However, there is huge demand for lower cost sequencing that can enable applications such as large population sequencing, disease screening and early detection.

A standard for measuring the cost of sequencing is the price of a 30× human genome, defined as 90 gigabases. The major cost components for sequencing systems are primarily the consumables which include biochip and reagents and secondarily the instrument costs.

SUMMARY

Recognized herein is the need for improved imaging methods and improved substrates and methods of producing substrates with dense layers of analytes. For example, to reach a $10 30× genome, a 100-fold cost reduction, it may be desirable to increase the amount of data per chip unit area by 100-fold and/or decrease the amount of reagent per data point by 100-fold. Thus, it may be desirable to provide chips with high density deoxyribonucleic acid (DNA) packing that can be imaged by a super-resolution imaging system.

In an example 1,000 genome platform with cluster densities of ten million molecules per square centimeter, each molecule occupies on average 10 um$^2$ of chip area. Thus, the average effective pitch is 3,160 nm. If densities increase 100-fold, for the same chip area and reagent, a 100-fold more information may be obtained resulting in 100-fold reduction in costs. At 100-fold higher density, the new pitch may need to be 320 nm.

Thus, to reduce sequencing cost, it is essential to achieve high density packing of target DNA molecules distributed on a surface of a low-cost biochip. However, the fluorescent signals generated from these densely packed molecules during sequencing need to be resolved by a super-resolution optical imaging system that can resolve optical signals below the diffraction limit of light.

Furthermore, although other methods exist that are not constrained by the diffraction limit of optical signals, such as electrical based systems developed by companies such as Ion Torrent and Oxford Nanopore, the lowest sequencing costs of all existing technologies may be achieved by optical based systems through the combination of high throughput imaging and low cost consumables.

Affordable, rapid sequencing may be causing a revolution in medicine and healthcare globally. As price of a genome has dropped dramatically since the first human genome was sequenced in year 2000, a significant milestone, $1,000 genome, was recently achieved. However, recognized herein is a huge demand for lower cost sequencing that can enable applications such as large population sequencing, disease screening and early detection. The present disclosure provides methods and systems to achieve a $10 genome in a substantially contracted time frame. At this price point, it may be economical to sequence every newborn and may remove the cost barrier for deep sequencing and single cell analysis.

A standard for measuring the cost of sequencing is the price of a 30× human genome, defined as 90 gigabases. The major cost components for sequencing systems may be primarily associated with the consumables, which may include a biochip and reagents, and secondarily the instrument costs. Thus, to reach a $10 30× genome, a 100-fold cost reduction, it may be desirable to increase the amount of data per chip unit area by 100-fold and/or decrease the amount of reagent per data point by 100-fold. Thus, it may be desirable to provide chips with high density DNA packing that can be imaged by a super-resolution imaging system.

In an example 1,000 genome platform with cluster densities of ten million molecules per square centimeter, each molecule occupies on average 10 micrometers (um$^2$) of chip area. Thus, the average effective pitch is 3,160 nanometers (nm). If densities increase 100-fold, for the same chip area and reagent, a 100-fold more information may be obtained resulting in 100-fold reduction in costs. At 100-fold higher density, the new pitch may need to be 320 nm.

Thus, to reduce sequencing cost, it may be essential to achieve high density packing of target DNA molecules distributed on a surface of a low-cost biochip. However, the fluorescent signals generated from these densely packed molecules during sequencing may need to be resolved by a super-resolution optical imaging system that can resolve optical signals below the diffraction limit of light.

Furthermore, although other methods exist that are not constrained by the diffraction limit of optical signals, such as electrical based systems developed by companies such as Ion Torrent and Oxford Nanopore, the lowest sequencing costs of all existing technologies are achieved by optical based systems through the combination of high throughput imaging and low cost consumables.

The present disclosure provides methods and systems for analyte detection, such as nucleic acid sequencing (e.g., to achieve a S10 genome in a substantially contracted time frame). Methods and systems of the present disclosure may be used to identify a nucleic acid molecule, such as DNA or a ribonucleic acid (RNA) molecule, a polypeptide, and/or a protein. At a price point that may be achieved using methods and systems of the present disclosure, it may be economical to sequence every newborn and may remove the cost barrier for deep sequencing and single cell analysis.

An aspect of the present disclosure comprises a method for sequencing a plurality of analytes disposed at high density on a surface of a substrate, comprising: providing a substrate comprising a surface, wherein the surface comprises a plurality of analytes disposed on the surface at a density such that a minimum effective pitch between binding locations of analytes of said plurality of analytes is less than $\lambda/(2*NA)$, wherein 'NA' is a numerical aperture of said optical imaging module, and wherein said surface comprises reagents for sequencing by synthesis; performing a plurality of cycles of probe binding to said plurality of analytes, a cycle of said plurality of cycles comprising: contacting said plurality of analytes with a plurality of probes, a probe of said plurality of probes comprising a detectable label; (ii) imaging a field of said surface with an optical system to detect an optical signal from each probe brought in contact with said plurality of analytes, thereby detecting a plurality of optical signals in said field for said cycle; determining a peak location from each of said plurality of optical signals from images of said field from at least two of said plurality of cycles; overlaying said peak locations for each optical signal and applying an optical distribution model at each cluster of optical signals to determine a relative position of each detected probe on said surface; resolving said optical signals in each field image from each cycle using said determined relative position and a resolving function; identifying said detectable labels for each field and each cycle from said deconvolved optical signals; and identifying analytes disposed on the surface of the substrate from said identified detectable labels across said plurality of cycles at each analyte position. In some embodiments, concatemers are loaded on the surface and closely packed to enable a center to center distance of ~250 nanometers (nm) with a variance of +/−25 nm. In some embodiments, the average center-to-center distance between molecules of about 315 nm. In some embodiments, the plurality of analytes (e.g., nucleic acid molecules) may be deposited adjacent to a surface such that adjacent analytes of the plurality of analytes may have average center-to-center spacings of at least 10 nanometers (nm), 50 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, or more. The average center-to-center spacings may be less than or equal to 500 nm, 490 nm, 480 nm, 470 nm, 460 nm, 450 nm, 440 nm, 430 nm, 420 nm, 410 nm, 400 nm, 390 nm, 380 nm, 370 nm, 360 nm, 350 nm, 340 nm, 330 nm, 320 nm, 310 nm, 300 nm, 290 nm, 280 nm, 270 nm, 260 nm, 250 nm, 240 nm, 230 nm, 220 nm, 210 nm, 200 nm, 190 nm, 180 nm, 170 nm, 160 nm, 150 nm, 140 nm, 130 nm, 120 nm, 110 nm, 100 nm, 50 nm, or less. The plurality of analytes may be nucleic acid molecules (DNA and/or RNA), proteins and/or polypeptides. The plurality of analytes may be disposed adjacent to a surface such that an individual analyte of the plurality of analytes may be resolved (e.g., optically resolved). The plurality of analytes may be disposed adjacent to the surface such that adjacent analytes of the plurality of analytes do not touch or contact each other. In some embodiments, said surface is unpatterned. In some embodiments, said surface is patterned. In some embodiments, one or more analytes of said plurality of analytes are treated with a repellant or attractive substance. In some embodiments, said repellant or attractive substance comprises zwitterionic features. In some embodiments, said repellant or attractive substance comprises PEG, a polysaccharide, ampholine ampholytes, sulphobetaine, and/or BSA. In some embodiments, said analytes are DNA concatemers. In some embodiments, said DNA concatemers are hybridized to ssDNA hairs. In some embodiments, said analytes are proteins or peptides. In some embodiments, said probes comprise a plurality of reversible terminator nucleotides. In some embodiments, said plurality of reversible terminator nucleotides comprises at least four distinct nucleotides each with a distinct detectable label. In some embodiments, said resolving comprises removing interfering optical signals from neighboring polynucleotides using a center-to-center distance between said neighboring polynucleotides from said determined relative positions. In some embodiments, said resolving function comprises machine learning. In some embodiments, said resolving function comprises nearest neighbor variable regression. In some embodiments, said polynucleotides are densely packed on said substrate such that there is overlap between optical signals emitted by said detectable labels from nucleotides incorporated into adjacent polynucleotides, and wherein said adjacent polynucleotides each comprise a distinct sequence. In some embodiments, the polynucleotides are deposited on said surface at an average density of more than 4 molecules per square micron. In some embodiments, said imaging of said surface is performed at a resolution of one pixel per 300 nm or higher along an axis of the image field. In some embodiments, an optical imagining module is configured to obtain said plurality of optical signals at a resolution of one pixel per 250 nanometers or higher. In some embodiments, an optical imagining module is configured to obtain said plurality of optical signals at a resolution of one pixel per 200 nanometers or higher. In some embodiments, an optical imagining module is configured to obtain said plurality of optical signals at a resolution of one pixel per 150 nanometers or higher. In some embodiments, an optical imagining module is configured to obtain said plurality of optical signals at a resolution of one pixel per 100 nanometers or higher. In some embodiments, the method further comprises generating an oversampled image with a higher pixel density from each of said field images from each cycle. In some embodiments, said overlaying said peak locations comprises aligning positions of said optical signal peaks detected in each field for a plurality of said cycles to generate a cluster of optical peak positions for each polynucleotide from said plurality of cycles. In some embodiments, said overlaying said peak locations comprises aligning positions of said optical signal peaks detected in each field for a subset of said cycles to generate a cluster of optical peak positions for each polynucleotide from said subset of cycles. In some embodiments, said optical distribution model comprises a point spread function. In some embodiments, said relative position of said analytes deposited to the surface of the substrate is determined within 10 nm RMS.

Another aspect of the present disclosure comprises a method for accurately determining a relative position of analytes deposited on a surface of a densely packed substrate, comprising: providing a substrate comprising a surface, wherein the surface comprises a plurality of analytes deposited on the surface at discrete locations; performing a plurality of cycles of probe binding and signal detection on said surface, each cycle comprising: contacting said analytes with a plurality of probes from a probe set, wherein said probes comprise a detectable label, wherein each of said probes binds specifically to a target analyte; and imaging a field of said surface with an optical system to detect a plurality of optical signals from individual probes bound to said analytes at discrete locations on said surface; determining a peak location from each of said plurality of optical signals from images of said field from at least two of said plurality of cycles; and overlaying said peak locations for each optical signal and applying an optical distribution model at each cluster of optical signals to determine a relative position of each detected analyte on said surface with improved accuracy. In some embodiments, concatemers are loaded on the surface and closely packed to enable a center to center distance of ~250 nm with a variance of +/−25 nm. In some embodiments, the average center-to-center distance between molecules of about 315 nm. In some embodiments, the plurality of analytes (e.g., nucleic acid molecules) may be deposited adjacent to a surface such that adjacent analytes of the plurality of analytes may have average center-to-center spacings of at least 10 nanometers (nm), 50 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, or more. The average center-to-center spacings may be less than or equal to 500 nm, 490 nm, 480 nm, 470 nm, 460 nm, 450 nm, 440 nm, 430 nm, 420 nm, 410 nm, 400 nm, 390 nm, 380 nm, 370 nm, 360 nm, 350 nm, 340 nm, 330 nm, 320 nm, 310 nm, 300 nm, 290 nm, 280 nm, 270 nm, 260 nm, 250 nm, 240 nm, 230 nm, 220 nm, 210 nm, 200 nm, 190 nm, 180 nm, 170 nm, 160 nm, 150 nm, 140 nm, 130 nm, 120 nm, 110 nm, 100 nm, 50 nm, or less. In some embodiments, said surface is unpatterned. In some embodiments, said surface is patterned. In some embodiments, the method further comprises: resolving said optical signals in each field image from each cycle using said determined relative position and a resolving function; and identifying said detectable labels bound to said deposited analytes for each field and each cycle from said deconvolved optical signals. In some embodiments, one or more analytes of said plurality of analytes are treated with a repellant or attractive substance. In some embodiments, said repellant or attractive substance comprises zwitterionic features. In some embodiments, said repellant or attractive substance comprises PEG, a polysaccharide, ampholine ampholytes, sulphobetaine, and/or BSA. In some embodiments, said analytes are DNA concatemers. In some embodiments, said DNA concatemers are hybridized to ssDNA hairs. In some embodiments, said analytes are proteins or peptides. In some embodiments, the method further comprises using said detectable label identity for each analyte detected at each cycle to identify a plurality of said analytes on said substrate. In some embodiments, said resolving comprises removing interfering optical signals from neighboring analytes using a center-to-center distance between said neighboring analytes from said determined relative positions of said neighboring analytes. In some embodiments, said resolving function comprises machine learning. In some embodiments, said resolving function comprises nearest neighbor variable regression. In some embodiments, said analytes are single biomolecules. In some embodiments, said analytes deposited on said surface are spaced apart on average less than the diffraction limit of the light emitted by the detectable labels and imaged by the optical system. In some embodiments, the deposited analytes comprises an average center-to-center distance between each analyte and the nearest adjacent analyte of less than 500 nm. In some embodiments, said overlaying said peak locations comprises aligning positions of said optical signal peaks detected in each field for a plurality of said cycles to generate a cluster of optical peak positions for each analyte from said plurality of cycles. In some embodiments, said relative position is determined with an accuracy of within 10 nm RMS. In some embodiments, said method resolves optical signals from a surface at a density of about 4 to about 25 analytes per square micron.

Another aspect of the present disclosure comprises a system for determining the identity of a plurality of analytes, comprising an optical imaging device configured to image a plurality of optical signals from a field of a substrate over a plurality of cycles of probe binding to analytes deposited on a surface of the substrate; and an image processing module, said module configured to: determine a peak location from each of said plurality of optical signals from images of said field from at least two of said plurality of cycles; determine a relative position of each detected analyte on said surface with improved accuracy by applying an optical distribution model to each cluster of optical signals from said plurality of cycles; and deconvolve said optical signals in each field image from each cycle using said determined relative position and a resolving function. In some embodiments, concatemers are loaded on the surface and closely packed to enable a center to center distance of ~250 nm with a variance of +/−25 nm. In some embodiments, the average center-to-center distance between molecules of about 315 nm. In some embodiments, the plurality of analytes (e.g., nucleic acid molecules) may be deposited adjacent to a surface such that adjacent analytes of the plurality of analytes may have average center-to-center spacings of at least 10 nanometers (nm), 50 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, or more. The average center-to-center spacings may be less than or equal to 500 nm, 490 nm, 480 nm, 470 nm, 460 nm, 450 nm, 440 nm, 430 nm, 420 nm, 410 nm, 400 nm, 390 nm, 380 nm, 370 nm, 360 nm, 350 nm, 340 nm, 330 nm, 320 nm, 310 nm, 300 nm, 290 nm, 280 nm, 270 nm, 260 nm, 250 nm, 240 nm, 230 nm, 220 nm, 210 nm, 200 nm, 190 nm, 180 nm, 170 nm, 160 nm, 150 nm, 140 nm, 130 nm, 120 nm, 110 nm, 100 nm, 50 nm, or less. In some embodiments, said surface is patterned. In some embodiments, said surface is unpatterned. In some embodiments, said surface is patterned. In some embodiments, said image processing module is further configured to determine an identity of said analytes deposited on said surface using said deconvolved optical signals. In some embodiments, said optical image device comprises a moveable stage defining a scannable area. In some embodiments, said optical image device comprises a sensor and optical magnification configured to sample a surface of a substrate at below the diffraction limit in said scannable area. In some embodiments, the system further comprises a substrate comprising analytes deposited to a surface of the substrate at a center-to-center spacing below the diffraction limit. In some embodiments, said resolving comprises removing interfering optical signals from neighboring analytes using a center-to-center distance between said neighboring analytes to determine said relative positions of said neighboring analytes. In some embodiments, said surface is unpatterned. In some embodiments, said surface is patterned.

Another aspect of the present disclosure comprises a method for processing or analyzing a plurality of analytes, comprising: disposing said plurality of analytes adjacent to a surface of a substrate at a density wherein a minimum effective pitch is less than a measure of $\lambda/(2*NA)$; obtaining a plurality of optical signals from said substrate over one or more cycles of probes binding to analytes of said plurality of analytes disposed adjacent to said substrate, wherein at least a subset of said plurality of optical signals overlap, which plurality of optical signals comprise light having a wavelength ($\lambda$); applying an imaging algorithm to process said plurality of optical signals to identify a position of an analyte of said plurality of analytes or a relative position of said analyte with respect to another analyte of said plurality of analytes; and using said positions or relative positions to identify said analytes of said plurality of analytes. In some embodiments, concatemers are loaded on the surface and closely packed to enable a center to center distance of ~250 nm with a variance of +/−25 nm. In some embodiments, the average center-to-center distance between molecules of about 315 nm. In some embodiments, the plurality of analytes (e.g., nucleic acid molecules) may be deposited adjacent to a surface such that adjacent analytes of the plurality of analytes may have average center-to-center spacings of at least 10 nanometers (nm), 50 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, or more. The average center-to-center spacings may be less than or equal to 500 nm, 490 nm, 480 nm, 470 nm, 460 nm, 450 nm, 440 nm, 430 nm, 420 nm, 410 nm, 400 nm, 390 nm, 380 nm, 370 nm, 360 nm, 350 nm, 340 nm, 330 nm, 320 nm, 310 nm, 300 nm, 290 nm, 280 nm, 270 nm, 260 nm, 250 nm, 240 nm, 230 nm, 220 nm, 210 nm, 200 nm, 190 nm, 180 nm, 170 nm, 160 nm, 150 nm, 140 nm, 130 nm, 120 nm, 110 nm, 100 nm, 50 nm, or less. In some embodiments, said surface is unpatterned. In some embodiments, said surface is patterned. In some embodiments, one or more analytes of said plurality of analytes are treated with a repellant or attractive substance. In some embodiments, said repellant or attractive substance comprises zwitterionic features. In some embodiments, said repellant or attractive substance comprises PEG, a polysaccharide, ampholine ampholytes, sulphobetaine, and/or BSA. In some embodiments, said analytes are DNA concatemers. In some embodiments, said DNA concatemers are hybridized to ssDNA hairs. In some embodiments, said analytes are proteins or peptides. In some embodiments, step (b) further comprises configuring an optical processing module to overlay said plurality of optical signals from said one or more cycles of probes binding to analytes and step (c) further comprises applying an optical distribution model said overlay of said plurality of optical signals to determine a relative position of each detected analyte. In some embodiments, said imaging algorithm comprises a resolving function. In some embodiments, said resolving function comprises machine learning. In some embodiments, said resolving function comprises nearest neighbor variable regression. In some embodiments, said resolving function comprises removing interfering optical signals from neighboring analytes using a center-to-center distance between said neighboring analytes. In some embodiments, said plurality of analytes are disposed adjacent to said substrate at a density of about 1 to 25 molecules per square micron. In some embodiments, an optical imagining module is configured to obtain said plurality of optical signals at a resolution of one pixel per 300 nanometers or higher. In some embodiments, an optical imagining module is configured to obtain said plurality of optical signals at a resolution of one pixel per 250 nanometers or higher. In some embodiments, an optical imagining module is configured to obtain said plurality of optical signals at a resolution of one pixel per 200 nanometers or higher. In some embodiments, an optical imagining module is configured to obtain said plurality of optical signals at a resolution of one pixel per 150 nanometers or higher. In some embodiments, an optical imagining module is configured to obtain said plurality of optical signals at a resolution of one pixel per 100 nanometers or higher.

Another aspect of the present disclosure comprises a method of controlling a distribution of an average minimum center-to-center distance between analytes of a plurality of analytes deposited on a surface, said method comprising treating said one or more analytes with a repellant or attractive substance. In some embodiments, concatemers are loaded on the surface and closely packed to enable a center to center distance of ~250 nm with a variance of +/−25 nm. In some embodiments, the average center-to-center distance between molecules of about 315 nm. In some embodiments, the plurality of analytes (e.g., nucleic acid molecules) may be deposited adjacent to a surface such that adjacent analytes of the plurality of analytes may have average center-to-center spacings of at least 10 nanometers (nm), 50 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, or more. The average center-to-center spacings may be less than or equal to 500 nm, 490 nm, 480 nm, 470 nm, 460 nm, 450 nm, 440 nm, 430 nm, 420 nm, 410 nm, 400 nm, 390 nm, 380 nm, 370 nm, 360 nm, 350 nm, 340 nm, 330 nm, 320 nm, 310 nm, 300 nm, 290 nm, 280 nm, 270 nm, 260 nm, 250 nm, 240 nm, 230 nm, 220 nm, 210 nm, 200 nm, 190 nm, 180 nm, 170 nm, 160 nm, 150 nm, 140 nm, 130 nm, 120 nm, 110 nm, 100 nm, 50 nm, or less. In some embodiments, said surface is unpatterned. In some embodiments, said surface is patterned. In some embodiments, said repellant or attractive substance comprises zwitterionic features. In some embodiments, said repellant or attractive substance comprises PEG, a polysaccharide, ampholine ampholytes, sulphobetaine, and/or BSA. In some embodiments, said analytes are DNA concatemers. In some embodiments, said DNA concatemers are hybridized to ssDNA hairs. In some embodiments, said analytes are proteins or peptides. In some embodiments, said average minimum center-to-center distance between one or more analytes of a plurality of analytes is less than about 500 nm. In some embodiments, said average minimum center-to-center distance between one or more analytes of a plurality of analytes is about 315 nm. In some embodiments, the plurality of analytes (e.g., nucleic acid molecules) may be deposited adjacent to a surface such that adjacent analytes of the plurality of analytes may have average center-to-center spacings of at least 10 nanometers (nm), 50 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, or more. The average center-to-center spacings may be less than or equal to 500 nm, 490 nm, 480 nm, 470 nm, 460 nm, 450 nm, 440 nm, 430 nm, 420 nm, 410 nm, 400 nm, 390 nm, 380 nm, 370 nm, 360 nm, 350 nm, 340 nm, 330 nm, 320 nm, 310 nm, 300 nm, 290 nm, 280 nm, 270 nm, 260 nm, 250 nm, 240 nm, 230 nm, 220 nm, 210 nm, 200 nm, 190 nm, 180 nm, 170 nm, 160 nm, 150 nm, 140 nm, 130 nm, 120 nm, 110 nm, 100 nm, 50 nm, or less. In some embodiments, said average minimum center-to-center distance between one or more analytes of a plurality of analytes is about 250 nm. In some embodiments, said treating of said one or more analytes with a repellant or attractive substance comprises applying said repellant or attractive substance to said surface prior to depositing said plurality of analytes to said surface. In some embodiments, said surface is unpatterned. In some embodiments, said surface is patterned.

Another aspect of the present disclosure comprises a method of controlling a distribution of an average minimum center-to-center distance between one or more analytes of a plurality of analytes deposited on a surface, said method comprising: treating said one or more analytes with a repellant or attractive substance; exposing said plurality of analytes to gas-liquid interface such that said plurality of analytes forms a monolayer of analytes deposited across said surface. In some embodiments, concatemers are loaded on the surface and closely packed to enable a center to center distance of –250 nm with a variance of +/–25 nm. In some embodiments, the average center-to-center distance between molecules of about 315 nm. In some embodiments, the plurality of analytes (e.g., nucleic acid molecules) may be deposited adjacent to a surface such that adjacent analytes of the plurality of analytes may have average center-to-center spacings of at least 10 nanometers (nm), 50 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, or more. The average center-to-center spacings may be less than or equal to 500 nm, 490 nm, 480 nm, 470 nm, 460 nm, 450 nm, 440 nm, 430 nm, 420 nm, 410 nm, 400 nm, 390 nm, 380 nm, 370 nm, 360 nm, 350 nm, 340 nm, 330 nm, 320 nm, 310 nm, 300 nm, 290 nm, 280 nm, 270 nm, 260 nm, 250 nm, 240 nm, 230 nm, 220 nm, 210 nm, 200 nm, 190 nm, 180 nm, 170 nm, 160 nm, 150 nm, 140 nm, 130 nm, 120 nm, 110 nm, 100 nm, 50 nm, or less. In some embodiments, said surface is unpatterned. In some embodiments, said surface is patterned. In some embodiments, said gas-liquid interface is an air-water interface. In some embodiments, the depositing of (c) comprises pulling or dragging. In some embodiments, said average minimum center-to-center distance between one or more analytes of a plurality of analytes is less than about 500 nm. In some embodiments, said average minimum center-to-center distance between one or more analytes of a plurality of analytes is about 315 nm. In some embodiments, said average minimum center-to-center distance between one or more analytes of a plurality of analytes is about 250 nm.

Another aspect of the present disclosure comprises a system comprising a plurality of nucleic acid molecules adjacent to a surface, which plurality of nucleic acid molecules do not contact one another. In some embodiments, concatemers are loaded on the surface and closely packed to enable a center to center distance of –250 nm with a variance of +/–25 nm. In some embodiments, the average center-to-center distance between molecules of about 315 nm. In some embodiments, the plurality of analytes (e.g., nucleic acid molecules) may be deposited adjacent to a surface such that adjacent analytes of the plurality of analytes may have average center-to-center spacings of at least 10 nanometers (nm), 50 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, or more. The average center-to-center spacings may be less than or equal to 500 nm, 490 nm, 480 nm, 470 nm, 460 nm, 450 nm, 440 nm, 430 nm, 420 nm, 410 nm, 400 nm, 390 nm, 380 nm, 370 nm, 360 nm, 350 nm, 340 nm, 330 nm, 320 nm, 310 nm, 300 nm, 290 nm, 280 nm, 270 nm, 260 nm, 250 nm, 240 nm, 230 nm, 220 nm, 210 nm, 200 nm, 190 nm, 180 nm, 170 nm, 160 nm, 150 nm, 140 nm, 130 nm, 120 nm, 110 nm, 100 nm, 50 nm, or less. In some embodiments, said surface is unpatterned. In some embodiments, said surface is patterned. In some embodiments, said plurality of nucleic acid molecules are a plurality of concatemers. In some embodiments, adjacent nucleic acid molecules of said plurality of nucleic acid molecules have an average center-to-center spacing of less than about 500 nm.

Another aspect of the present disclosure comprises a method, comprising providing a plurality of nucleic acid molecules adjacent to a surface under conditions such that said plurality of nucleic acid molecules do not contact one another. In some embodiments, concatemers are loaded on the surface and closely packed to enable a center to center distance of –250 nm with a variance of +/–25 nm. In some embodiments, the average center-to-center distance between molecules of about 315 nm. In some embodiments, the plurality of analytes (e.g., nucleic acid molecules) may be deposited adjacent to a surface such that adjacent analytes of the plurality of analytes may have average center-to-center spacings of at least 10 nanometers (nm), 50 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, or more. The average center-to-center spacings may be less than or equal to 500 nm, 490 nm, 480 nm, 470 nm, 460 nm, 450 nm, 440 nm, 430 nm, 420 nm, 410 nm, 400 nm, 390 nm, 380 nm, 370 nm, 360 nm, 350 nm, 340 nm, 330 nm, 320 nm, 310 nm, 300 nm, 290 nm, 280 nm, 270 nm, 260 nm, 250 nm, 240 nm, 230 nm, 220 nm, 210 nm, 200 nm, 190 nm, 180 nm, 170 nm, 160 nm, 150 nm, 140 nm, 130 nm, 120 nm, 110 nm, 100 nm, 50 nm, or less. In some embodiments, said surface is unpatterned. In some embodiments, said surface is patterned. In some embodiments, said plurality of nucleic acid molecules are a plurality of concatemers. In some embodiments, adjacent nucleic acid molecules of said plurality of nucleic acid molecules have an average center-to-center spacing of less than about 500 nm.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 1 shows sequencer throughput versus array pitch and outlines a system design which meets the criteria needed for a S10 genome.

FIG. 10A shows a flowchart of operations for initial raw image analysis, according to an embodiment of the present disclosure.

FIG. 10B shows a flowchart of operations for location determination from optical signal peak information from a plurality of cycles, according to an embodiment of the present disclosure.

FIGS. 27A-27B show various base pair reads. FIG. 27C shows the resolution of base calling at individual spots for *E. coli* sequencing.

DETAILED DESCRIPTION

Figure 2A:
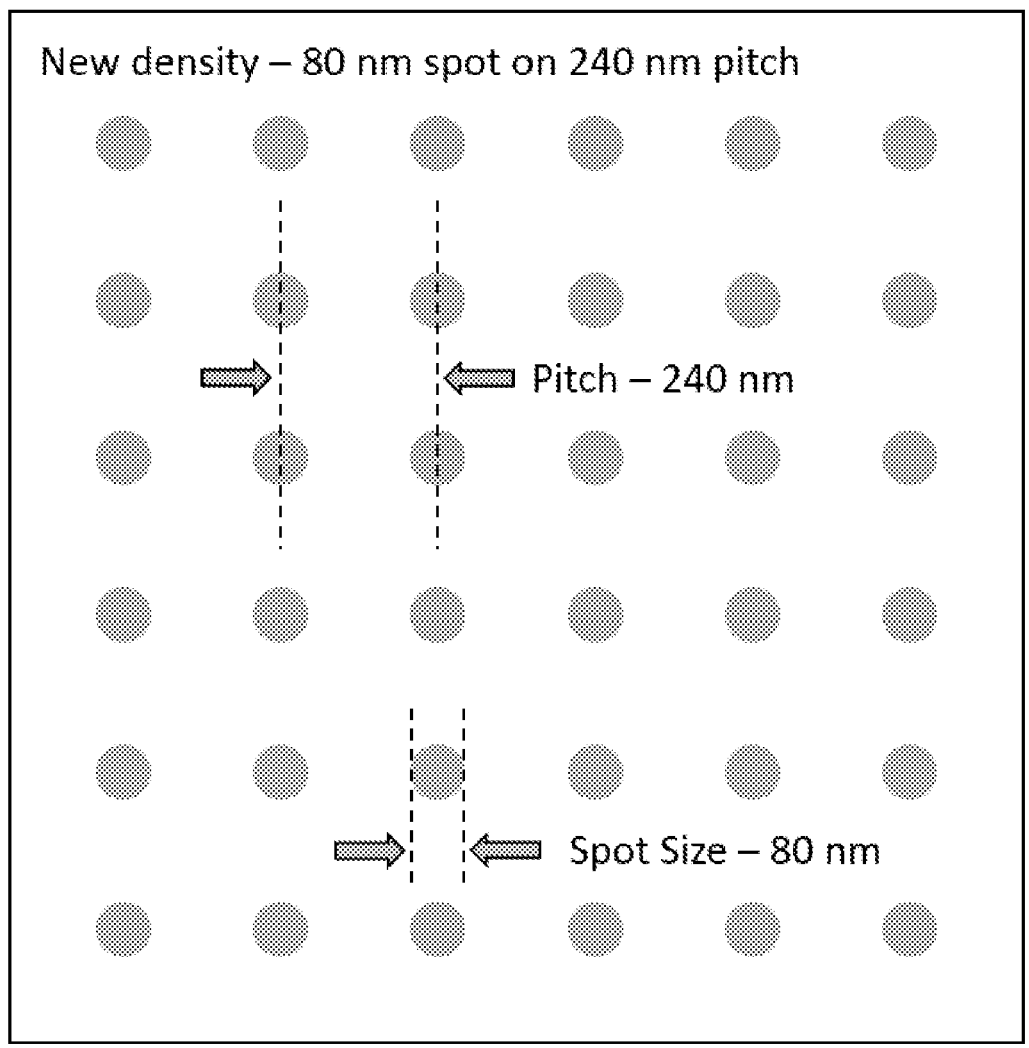
FIG. 2A shows a proposed embodiment of a high-density region of 80 nm diameter binding regions (spots) on a 240 nm pitch for low cost sequencing.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein, the term "center-to-center distance" generally refers to a distance between two adjacent molecules as measured by the difference between the average position of each molecule on a substrate. The term average minimum center-to-center distance refers specifically to the average distance between the center of each analyte disposed on the substrate and the center of its nearest neighboring analyte, although the term center-to-center distance refers also to the minimum center-to-center distance in the context of limitations corresponding to the density of analytes on the substrate. As used herein, the term "pitch" or "average effective pitch" is generally used to refer to average minimum center-to-center distance. In the context of regular arrays of analytes, pitch may also be used to determine a center-to-center distance between adjacent molecules along a defined axis.

As used herein, the term "overlaying" (e.g., overlaying images) generally refers to overlaying images from different cycles to generate a distribution of detected optical signals (e.g., position and intensity, or position of peak) from each analyte over a plurality of cycles. This distribution of detected optical signals can be generated by overlaying images, overlaying artificial processed images, or overlaying datasets comprising positional information. Thus, as used herein, the term "overlaying images" generally encompasses any of these mechanisms to generate a distribution of position information for optical signals from a single probe bound to a single analyte for each of a plurality of cycles.

A "cycle" is generally defined by completion of one or more passes and stripping of the detectable label from the substrate. Subsequent cycles of one or more passes per cycle can be performed. For the methods and systems described herein, multiple cycles are performed on a single substrate or sample. For deoxyribonucleic acid (DNA) sequencing, multiple cycles may require the use of a reversible terminator and a removable detectable label from an incorporated nucleotide. For proteins, multiple cycles may require that the probe removal (stripping) conditions either maintain proteins folded in their proper configuration, or that the probes used are chosen to bind to peptide sequences so that the binding efficiency is independent of the protein fold configuration.

A "pass" in a detection assay generally refers to a process where a plurality of probes comprising a detectable label are introduced to the bound analytes, selective binding occurs between the probes and distinct target analytes, and a plurality of signals are detected from the detectable labels. A pass includes introduction of a set of antibodies that bind specifically to a target analyte. A pass can also include introduction of a set of labelled nucleotides for incorporation into the growing strand during sequencing by synthesis. There can be multiple passes of different sets of probes before the substrate is stripped of all detectable labels, or before the detectable label or reversible terminator is removed from an incorporated nucleotide during sequencing. In general, if four nucleotides are used during a pass, a cycle may only include a single pass for standard four nucleotide sequencing by synthesis.

As used herein, an "image" generally refers to an image of a field taken during a cycle or a pass within a cycle. In some embodiments, a single image is limited to detection of a single color of a detectable label.

As used herein, the term "field" generally refers to a single region of a substrate that is imaged. During a typical assay a single field is imaged at least once per cycle. For example, for a 20 cycle assay, with 4 colors, there can be 20*4=80 images, all of the same field.

A "target analyte" or "analyte" generally refers to a molecule, compound, complex, substance or component that is to be identified, quantified, and otherwise characterized. A target analyte can comprise by way of example, but not limitation to, a single molecule (of any molecular size), a single biomolecule, a polypeptide, a protein (folded or unfolded), a polynucleotide molecule (ribonucleic acid (RNA), complementary DNA (cDNA), or DNA), a fragment thereof, a modified molecule thereof, such as a modified nucleic acid, or a combination thereof. In an embodiment, a target polynucleotide comprises a hybridized primer to facilitate sequencing by synthesis. The target analytes are recognized by probes, which can be used to sequence, identify, and quantify the target analytes using optical detection methods described herein.

A "probe," as used herein generally refers to a molecule that is capable of binding to other molecules (e.g., a complementary labelled nucleotide during sequencing by synthesis, polynucleotides, polypeptides or full-length proteins, etc.), cellular components or structures (lipids, cell walls, etc.), or cells for detecting or assessing the properties of the molecules, cellular components or structures, or cells. The probe comprises a structure or component that binds to the target analyte. In some embodiments, multiple probes may recognize different parts of the same target analyte. Examples of probes include, but are not limited to, a labelled reversible terminator nucleotide, an aptamer, an antibody, a polypeptide, an oligonucleotide (DNA, RNA), or any combination thereof. Antibodies, aptamers, oligonucleotide sequences and combinations thereof as probes are also described in detail below.

The probe can comprise a detectable label that is used to detect the binding of the probe to a target analyte. The probe can be directly or indirectly bound to, hybridized to, conjugated to, or covalently linked to the target analyte.

As used herein, the term "detectable label" generally refers to a molecule bound to a probe that can generate a detectable optical signal when the probe is bound to a target analyte and imaged using an optical imaging system. The detectable label can be directly or indirectly bound to, hybridized to, conjugated to, or covalently linked to the probe. In some embodiments, the detectable label is a fluorescent molecule or a chemiluminescent molecule. The probe can be detected optically via the detectable label.

As used herein, the term "optical distribution model" generally refers to a statistical distribution of probabilities for light detection from a point source. These include, for example, a Gaussian distribution. The Gaussian distribution can be modified to include anticipated aberrations in detection to generate a point spread function as an optical distribution model.

Provided herein are systems and methods that facilitate optical detection and discrimination of probes bound to tightly packed analytes bound to the surface of a substrate. In part, the methods and systems described herein rely on repeated detection of a plurality of target analytes on the surface of a substrate to improve the accuracy of identification of a relative location of each analyte on the substrate. This information can then be used to perform signal resolving on each image of a field of the substrate for each cycle to reliably identify a signal from a probe bound to the target analyte. In some embodiments, the resolving comprises deconvolution. In some embodiments, this type of deconvolution processing can be used to distinguish between different probes bound to the target analyte that have overlapping emission spectrum when activated by an activating light. In some embodiments, the deconvolution processing can be used to separate optical signals from neighboring analytes. This is especially useful for substrates with analytes having a density wherein optical detection is challenging due to the diffraction limit of optical systems.

In some embodiments, the methods and systems described herein are particularly useful in sequencing. By providing methods and systems that facilitate reliable optical detection on densely packed substrates, costs associated with sequencing, such as reagents, number of clonal molecules used, processing and read time, can all be reduced to greatly advance sequencing technologies, specifically, sequencing by synthesis using optically detected nucleotides.

Although the systems and methods described herein have important implications for advancing sequencing technology, the methods and systems described herein are generally applicable to optical detection of analytes bound to the surface of a substrate, including on the single molecule level.

Sequencing Cost Reduction

Sequencing technologies include image-based systems developed by companies such as Illumina and Complete Genomics and electrical based systems developed by companies such as Ion Torrent and Oxford Nanopore. Image-based sequencing systems currently have the lowest sequencing costs of all existing sequencing technologies. Image-based systems achieve low cost through the combination of high throughput imaging optics and low-cost consumables. However, prior art optical detection systems have minimum center-to-center spacing between adjacent resolvable molecules of about a micron, in part due to the diffraction limit of optical systems. In some embodiments, described herein are methods for attaining significantly lower costs for an image-based sequencing system using existing biochemistries using cycled detection, determination of precise positions of analytes, and use of the positional information for highly accurate deconvolution of imaged signals to accommodate increased packing densities below the diffraction limit.

Densely-Packed Analyte Layers and Detection Methods

Provided herein are systems and methods to facilitate imaging of signals from analytes deposited on a surface with a center-to-center spacing below the diffraction limit. These systems and methods use advanced imaging systems to generate super-resolution images, and cycled detection to facilitate positional determination of molecules on the substrate with high accuracy and resolving of images to obtain signal identity for each molecule on a densely packed surface with high accuracy. These methods and systems allow sequencing by synthesis on a densely packed substrate to provide highly efficient and very high throughput polynucleotide sequence determination with high accuracy.

The major cost components for sequencing systems are primarily the consumables which include biochip and reagents and secondarily the instrument costs. To reach a S10 30× genome, a 100-fold cost reduction, the amount of data per unit area needs to increase by 100-fold and the amount of reagent per data point needs to drop by 100-fold.

FIG. 1 shows sequencer throughput versus array pitch and outlines a system design which meets the criteria needed for a S10 genome. The basic idea is that to achieve a 100-fold cost reduction, the amount of data per unit area needs to increase by 100-fold and the amount of reagent per data point needs to drop by 100-fold. To achieve these reductions in costs, provided herein are methods and systems that facilitate reliable sequencing of polynucleotides deposited on the surface of a substrate at a density below the diffraction limit. These high densities allow for more efficient usage of reagents and increase the amount of data per unit area. In addition, the increase in the reliability of detection allows for a decrease in the number of clonal copies that may be synthesized to identify and correct errors in sequencing and detection, further reducing reagent costs and data processing costs.

High Density Distributions of Analytes on a Surface of a Substrate

FIG. 2A shows a proposed embodiment of a high-density region of 80 nm diameter binding regions (spots) on a 240 nm pitch. In this embodiment, an ordered array can be used where single-stranded DNA molecule exclusively binds to specified regions on chip. In some embodiments, concatemers (i.e., a long continuous DNA molecule that contains multiple copies of the same DNA sequence linked in series) smaller than 40 kB are used so as to not overfill the spot. The size of the concatemers scales roughly with area, meaning the projected length of the smaller concatemer may be approximate 4 kB to 5 kB resulting in approximately 10 copies if the same amplification process is used. It is also possible to use 4 kB lengths of DNA and sequence each concatemer directly. Another option is to bind a shorter segment of DNA with unsequenced filler DNA to bring the total length up to the size needed to create an exclusionary molecule.

Figure 2B:
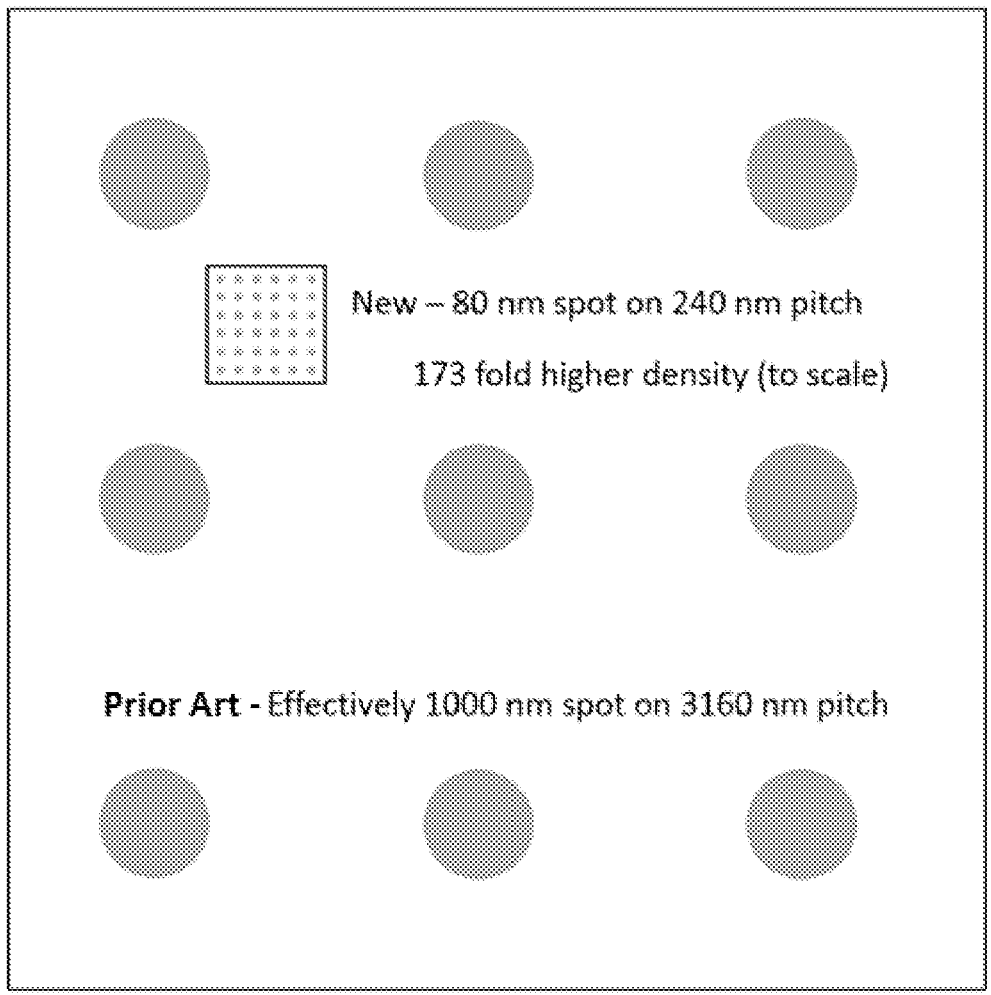
FIG. 2B is a comparison of the proposed substrate density compared to a sample effective density used for a 1,000 genome.

FIG. 2B is a comparison of the proposed pitch compared to a sample effective pitch used for a S1,000 genome. The density of the new array is 170-fold higher, meeting the criteria of achieving 100-fold higher density. The number of copies per imaging spot per unit area also meets the criteria of being at least 100-fold lower than the prior existing platform. This helps ensure that the reagent costs are 100-fold more cost effective than baseline.

Imaging Densely Packed Single Biomolecules and the Diffraction Limit

One constraint for increased molecular density for an imaging platform is the diffraction limit. The equation for the diffraction limit of an optical system is:

$$D = \lambda/2NA$$

where D is the diffraction limit, $\lambda$, is the wavelength of light, and NA is the numerical aperture of the optical system. Typical air imaging systems have NA's of 1.0 to 1.2. Using $\lambda = 600$ nm, the diffraction limit is between 250 nm and 300 nm. For a water immersion system, the NA is ~1.0, giving a diffraction limit of 300 nm.

If features on an array or other substrate surface comprising biomolecules are too close, two optical signals may overlap substantially so that you just see a single blob that cannot be reliably resolved based on the image alone. This can be exacerbated by errors introduced by the optical imaging system, such as blur due to inaccurate tracking of a moving substrate, or optical variations in the light path between the sensor and the surface of a substrate.

The transmitted light or fluorescence emission wavefronts emanating from a point in the specimen plane of the microscope become diffracted at the edges of the objective aperture, effectively spreading the wavefronts to produce an image of the point source that is broadened into a diffraction pattern having a central disk of finite, but larger size than the original point. Therefore, due to diffraction of light, the image of a specimen never perfectly represents the real details present in the specimen because there is a lower limit below which the microscope optical system cannot resolve structural details.

The observation of sub-wavelength structures with microscopes is difficult because of the diffraction limit. A point object in a microscope, such as a fluorescent protein or polynucleotide, may generate an image at the intermediate plane that may include a diffraction pattern created by the action of interference. When highly magnified, the diffraction pattern of the point object may be observed to include a central spot (diffraction disk) surrounded by a series of diffraction rings. Combined, this point source diffraction pattern is referred to as an Airy disk.

The size of the central spot in the Airy pattern is related to the wavelength of light and the aperture angle of the objective. For a microscope objective, the aperture angle is described by the numerical aperture (NA), which includes the term $\sin(\theta)$, the half angle over which the objective can gather light from the specimen. In terms of resolution, the radius of the diffraction Airy disk in the lateral (x,y) image plane is defined by the following formula: Abbe Resolution=$\lambda/2*NA$, where $\lambda$ is the average wavelength of illumination in transmitted light or the excitation wavelength band in fluorescence. The objective numerical aperture (NA=$n \cdot \sin(\theta)$) is defined by the refractive index of the imaging medium (n; usually air, water, glycerin, or oil) multiplied by the sine of the aperture angle ($\sin(\theta)$). As a result of this relationship, the size of the spot created by a point source decreases with decreasing wavelength and increasing numerical aperture, but always remains a disk of finite diameter. The Abbe resolution (i.e., Abbe limit) is also referred to herein as the diffraction limit and defines the resolution limit of the optical system.

If the distance between the two Airy disks or point-spread functions is greater than the diffraction limit, the two point sources are considered to be resolved (and can readily be distinguished). Otherwise, the Airy disks merge together and are considered not to be resolved.

Figure 20:
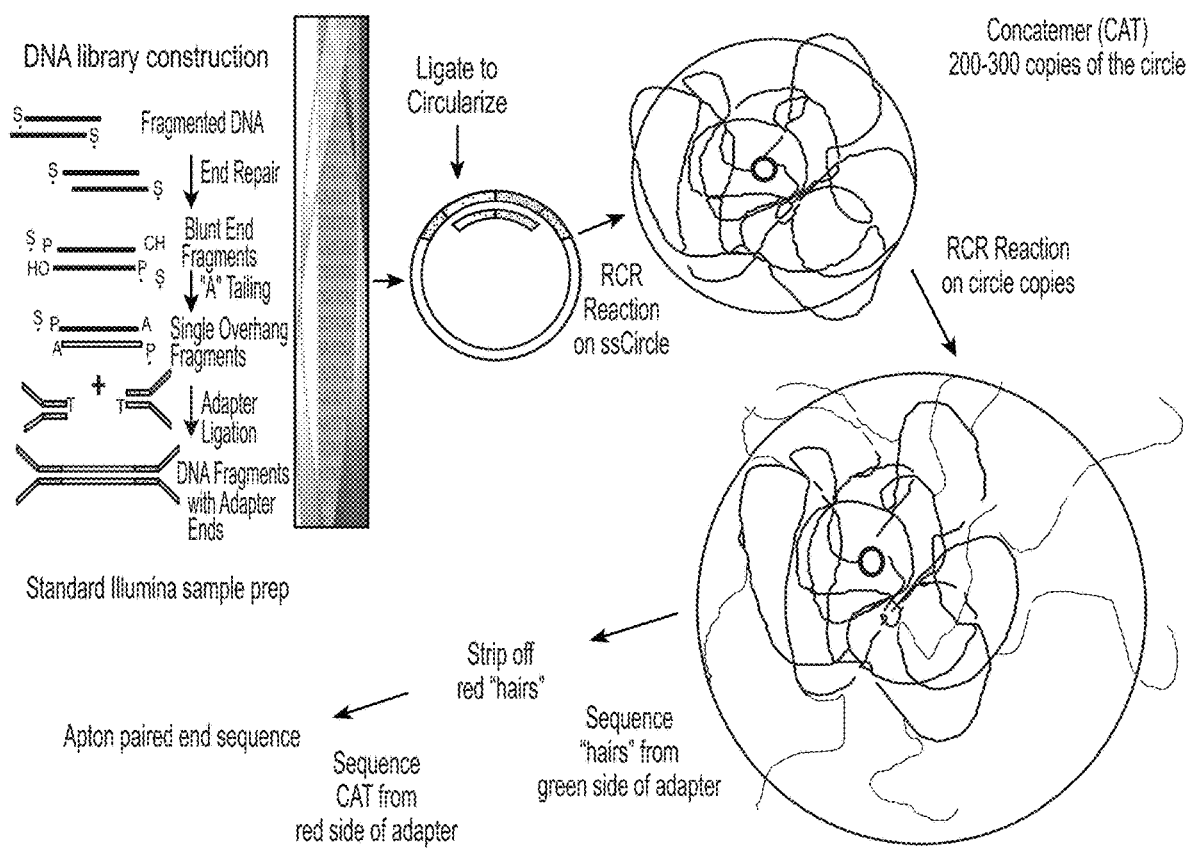
FIG. 20 shows a flowchart of DNA library construction, circularization, and concatemer formation, including synthesis of ssDNA 'hairs' on the concatemer to facilitate exclusion for formation of a layer of concatemers, according to an embodiment of the present disclosure.

Thus, light emitted from a detectable label point source with wavelength 2, traveling in a medium with refractive index n and converging to a spot with half-angle $\theta$ may make a diffraction limited spot with a diameter: d=$\lambda/2*NA$. Considering green light around 500 nm and a NA (Numerical Aperture) of 1, the diffraction limit is roughly d=$\lambda/2$=250 nm (0.25 pm), which limits the density of analytes such as proteins, nucleotides and other sequencing substrates (e.g., as shown in FIG. 20) on a surface able to be imaged by conventional imaging techniques. As used herein, sequencing substrates include any analyte that sequence information can be derived from, such as a template for a sequencing reaction. Even in cases where an optical microscope is equipped with the highest available quality of lens elements, is perfectly aligned, and has the highest numerical aperture, the resolution remains limited to approximately half the wavelength of light in the best-case scenario. To increase the resolution, shorter wavelengths can be used such as UV and X-ray microscopes. These techniques offer better resolution but are expensive, suffer from lack of contrast in biological samples and may damage the sample.

Image Resolving

In some embodiments, the image resolving methods described herein comprise deconvolution. Deconvolution is an algorithm-based process used to reverse the effects of convolution on recorded data. The concept of deconvolution is widely used in the techniques of signal processing and image processing. Because these techniques are in turn widely used in many scientific and engineering disciplines, deconvolution finds many applications.

In optics and imaging, the term "deconvolution" is specifically used to refer to the process of reversing the optical distortion that takes place in an optical microscope, electron microscope, telescope, or other imaging instrument, thus creating clearer images. It is usually done in the digital domain by a software algorithm, as part of a suite of microscope image processing techniques.

The usual method is to assume that the optical path through the instrument is optically perfect, convolved with a point spread function (PSF), that is, a mathematical function that describes the distortion in terms of the pathway a theoretical point source of light (or other waves) takes through the instrument. Usually, such a point source contributes a small area of fuzziness to the final image. If this function can be determined, it is then a matter of computing its inverse or complementary function, and convolving the acquired image with that. Deconvolution maps to division in the Fourier co-domain. This allows deconvolution to be easily applied with experimental data that are subject to a Fourier transform. An example is NMR spectroscopy where the data are recorded in the time domain, but analyzed in the frequency domain. Division of the time-domain data by an exponential function has the effect of reducing the width of Lorenzian lines in the frequency domain. The result is the original, undistorted image.

However, for diffraction limited imaging, deconvolution is also needed to further refine the signals to improve resolution beyond the diffraction limit, even if the point spread function is perfectly known. It is very hard to separate two objects reliably at distances smaller than the Nyquist distance. However, described herein are methods and systems using cycled detection, analyte position determination, alignment, and deconvolution to reliably detect objects separated by distances much smaller than the Nyquist distance.

Making High Density Random Layers of Concatemers for Sequencing

Also provided herein are methods of making and using high density concatemer layers. In some embodiments, the concatemers are randomly distributed on a surface of a substrate in a close-packed layer for individual detection and sequencing. In some embodiments, provided herein are methods of making and randomly distributing a layer of concatemers on a substrate such that they achieve a high density or average center-to-center distance.

Concatemers (i.e., CATs), are long single-stranded DNA molecules made through rolling circle amplification (RCA) of a ssCircular DNA. In some embodiments, the concatemers each comprise from a few up to several hundred copies of a target DNA sequence inserted between known sequence adapters. A library of concatemers comprising target DNA sequences can be generated. In some embodiments, the concatemers comprise features that self-exclude to facilitate layering a close-packed single layer of concatemers on a substrate with minimal overlap or a minimum distance between adjacent concatemers and without needing specific attachment points on the substrate. These exclusionary features facilitate close-packed layers while minimizing the number of nearest neighbor concatemers that are too close to be resolved by optical imaging, as described herein.

In some embodiments, provided herein are substrates comprising a surface, wherein the surface is bound to a close-packed, randomly distributed collection of amplified targets, such as DNA concatemers.

In some embodiments, this substrate is used to facilitate nucleotide sequencing, including of whole genomes or exomes. In some embodiments, large numbers of individual cellular targets can be sequenced. These can represent a selected panel of targets using cluster sequencing. Sequencing as described herein can be used, for example, to (i) detect multiple genetic variants (e.g., for genotyping, drug resistance determination, paternity, or identification), (ii) sequence multiple cDNA molecules for gene expression analysis for enumeration of pathway dynamics, or (iii) detect methylated residues on a target polynucleotide following bi-sulphite treatment. In some embodiments, sequencing methods require target amplification to generate small clusters of ~200 target copies as described in the embodiments.

The method, in one embodiment, comprises: the creation of circularized single stranded molecules for targets across the genome using ligase reactions, amplification of the circularized DNA using isothermal whole genome amplification methods to generate clusters of circularized amplified targets (CAT) that have a few hundred copies, and ensuring that the CATs are coated with appropriate reagents to generate nanospheres that have a uniform size around 250 nm with a distribution around 225-275 nm.

The method, in one embodiment further comprises: distributing the CATs on a bio-chip in a densely packed collection and attaching them to the surface with removal of the coating materials, and ensuring that the CATs remain bound to the slide through multiple cycles of sequencing reactions.

In some embodiments, the target biomolecules are detected and/or sequenced and authenticated based on repeat hybridizations. This facilitates improved accuracy, including a decrease in sensitivity and/or specificity to provide improved target identification and/or sequencing.

In some embodiments, single base extension assays and oligonucleotide ligation assays are performed at single molecule levels to provide authentication. This level of authentication allows very high multiplexing and digital counting to quantify relative and absolute abundance with a higher accuracy previously unavailable via optical imaging.

Sequencing

Optical detection imaging systems are diffraction-limited, and thus have a theoretical maximum resolution of ~300 nm with fluorophores typically used in sequencing. To date, the best sequencing Systems have had center-to-center spacings between adjacent polynucleotides of ~600 nm on their arrays, or ~2× the diffraction limit. This factor of 2× is needed to account for intensity, array & biology variations that can result in errors in position. To achieve a 10 genome, an approximately 200 nm center to center spacing is required, which requires sub-diffraction-limited imaging capability.

For sequencing, the purpose of the system and methods described herein are to resolve polynucleotides that are sequenced on a substrate with a center-to-center spacing below the diffraction limit of the optical system.

As described herein, we provide methods and systems to achieve sub-diffraction-limited imaging in part by identifying a position of each analyte with a high accuracy (e.g., 10 nm RMS or less). By comparison, state of the art Super Resolution systems can only identify location with an accuracy down to 20 nm RMS, 2× worse than this system. Thus, the methods and system disclosed herein enable sub-diffraction limited-imaging to identify densely-packed molecules on a substrate to achieve a high data rate per unit of enzyme, data rate per unit of time, and high data accuracy. These sub-diffraction limited imaging techniques are broadly applicable to techniques using cycled detection as described herein.

Multiple Cycles of Sequencing Concatemers
Methods of Making CATs
Creation of Circularized ssDNA Targets In some embodiments, described herein are methods of preparing a library of concatemers to distribute as a layer onto the surface of a substrate, e.g., as randomly distributed, densely packed layer. To synthesize concatemers comprising target DNA to be sequenced, first, target DNA can be amplified and converted into circular DNA templates. In some embodiments, amplification products undergo circular template ligation, which can be conducted via template mediated enzymatic ligation (e.g., T4 DNA ligase) or template-free ligation using special DNA ligases (i.e., CircLigase) to form a precursor to the concatemers formed via rolling circle amplification of the circular DNA templates.

RCA/RCR Basic Technique

Rolling circle replication describes a process of unidirectional nucleic acid replication that can rapidly synthesize multiple copies of circular molecules of DNA or RNA.

RCA (rolling circle amplification) is an isothermal nucleic acid amplification technique where the polymerase continuously adds single nucleotides to a primer annealed to a circular template which results in a long concatemer ssDNA that contains tens to hundreds of tandem repeats (complementary to the circular template).

Rolling circle amplification can be performed by exposing the circular DNA templates to: 1. A DNA polymerase. 2. A suitable buffer that is compatible with the polymerase. 3. A short DNA or RNA primer. 4. Deoxynucleotide triphosphates (dNTPs).

In some embodiments, the polymerase used in rolling circle amplification is Phi29, Bst, or Vent exo-DNA polymerase for DNA amplification, and T7 RNA polymerase for RNA amplification. RCA can be conducted at a constant temperature (room temperature to 37° C.) in both free solution and on top of deposited targets (solid phase amplification). A DNA RCA reaction typically proceeds via primer-induced single-strand DNA elongation.

Figure 19:
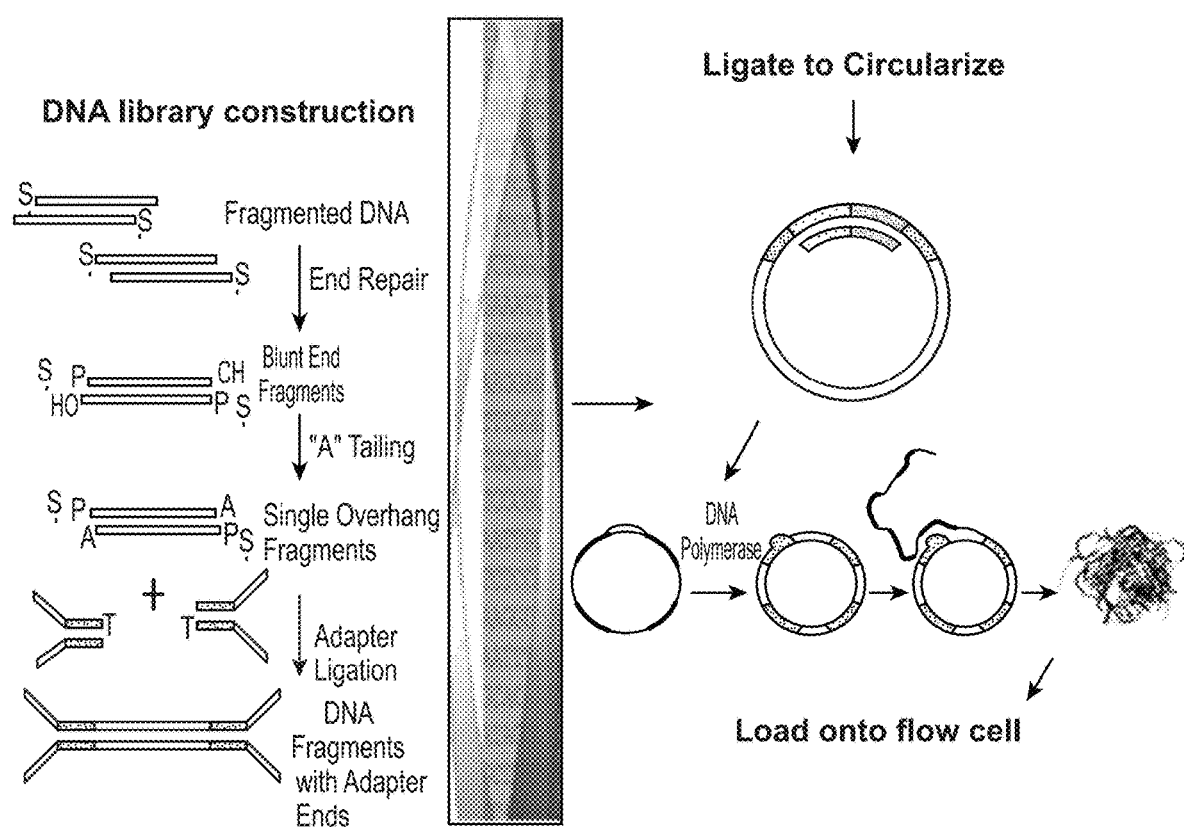
FIG. 19 shows a flowchart of deoxyribonucleic acid (DNA) library construction, circularization, and concatemer formation, according to an embodiment of the present disclosure.

In some embodiments, a method for constructing concatemer libraries of sequencing substrates to load onto a physical substrate, such as a flow cell, is shown in FIG. 19. In some embodiments, concatemer libraries of sequencing substrates are constructed as shown in FIG. 20. 'Hairs' are ssDNA molecules that can be generated by using a reverse primer to synthesize in the opposite direction as the extending concatemer DNA. These 'hairs' can be used to control the size and/or exclusion properties of the concatemers. In some embodiments, the sequencing reaction described herein occurs using the ssDNA 'hairs' as templates.

Terminating RCR Reaction

The rolling circle amplification of the CAT can be stopped by the addition of EDTA to chelate the essential Mg2+ co-factor of the phi29 enzyme. Phi29 is a strongly displacing polymerase, while the standard polymerases used for sequencing, for example Therminator 9, are only weakly displacing. A more displacing enzyme for sequencing this substrate may be used or adapted.

Alternatively, one may use single strand binding proteins (SSBs) or helicases, or combinations of them to aid in the displacement. These may be added to the extension reaction or used as pre-incubation operations to prepare the substrate for sequencing.

Alternatively, the rolling circle reaction may be stopped using an unlabeled reversible terminator. This may be a way to make the stoppage more uniform within the solution, yielding more uniform-sized CATs than stoppage with EDTA. Additionally, the sequencing reaction may then be initiated from the unblocking operation, followed by extension with labeled reversible terminator nucleotides. This may allow for the natural selection of substrates that where the extending 3' end was accessible for the normal reactions of sequencing by synthesis.

The phi29 is likely very tightly bound to the extending end of the CAT. The use of a reversible terminator to stop the reaction may destabilize that interaction. Other protein denaturants like chaotropic salts or detergents may be necessary to displace the phi29 to enable the sequencing reaction Concatemer Composition The CATs have several identical copies of the target DNA on the extending single strand. CATs can also have several identical reverse copies of the target DNA on ssDNA 'hairs' generated as described above.

In some embodiments concatemers are at least 1,000 nucleotides in length (no more than, from 400,000).

In some embodiments, concatemers are at least 150 nm in diameter (no more than 300 nm). Preferably, the exclusion zone between adjacent concatemers is not less than the minimum center-to-center distance necessary to achieve the desired density or pitch.

Densely-Packed Random Arrays
Methods of Making Arrays (Randomly Distributed Close Packed Layer of Concatemers)
Controlled Spacing Provided herein are several mechanisms to control the distribution of minimum center-to-center distance between CATs arrayed on an un-patterned surface. In some embodiments, these methods and compositions facilitate formation of a uniform, close-packed self-assembled random layer of CATs with a controlled minimum center-to-center distance between adjacent CATs such that they can be sequenced with minimal cross-talk between the dye-labeled sequencing substrates.

The CATs themselves are mutually repellant in solution due to their strong negative charge, but they may nonetheless be too close to each other for effective diffusion-limited resolution of labeled adjacent CATs once adsorbed to a surface.

In some embodiments, the concatemers are 'encased' or 'enveloped' in a shell of a repellant or attractive substance to increase their effective exclusion size without altering the size of the CAT itself or the number of copies of the sequencing substrate they contain.

In some embodiments, a protein layer to which the CATs adsorb on the surface of the substrate is modified to space the interacting proteins out on the surface. For example, the CATs can interact with the glass, silicon or modified (e.g. amino-silanated) surface through an interaction with proteins that have been previously adsorbed to the surface.

Thus, modifications of the CAT or the protein partner of the binding pair can assist in size exclusion to achieve a uniform, densely-packed layer of concatemers on a surface without specific attachment points for the CATs. In some embodiments, these modifications include crosslinking or attaching molecules like PEG or polysaccharide to coat the CAT or its protein binding partner.

Figure 21A:
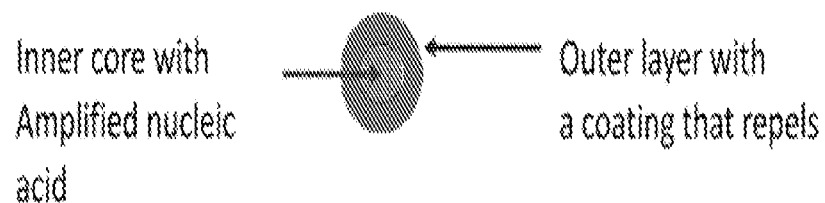
FIGS. 21A and 21B depict coated concatemers to facilitate exclusion from other concatemers in a layer of concatemers, according to an embodiment of the present disclosure.
Figure 21B:
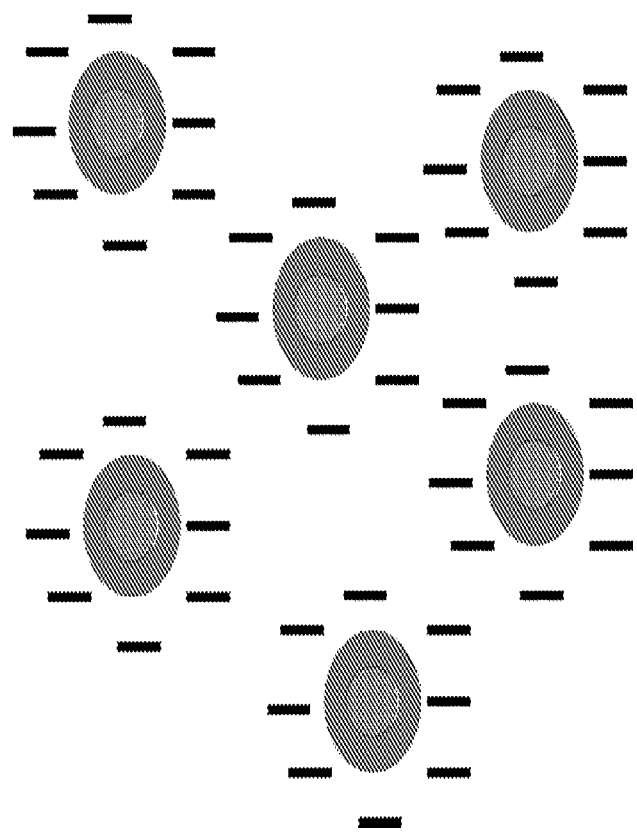
Figure 22:
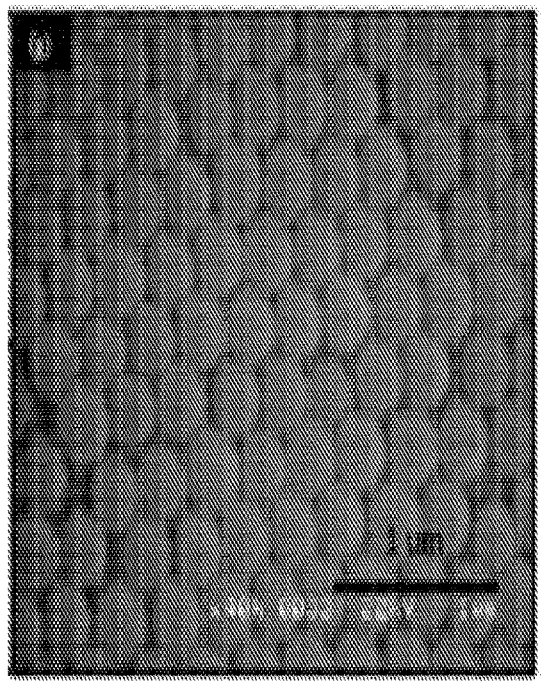
FIG. 22 shows an embodiment of a closely-packed randomly distributed layer of concatemers, according to an embodiment of the present disclosure.
Figure 22:
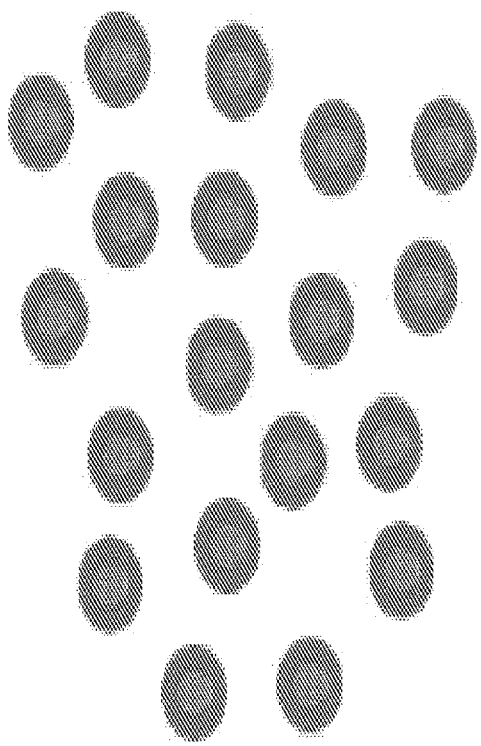

Shown in FIG. 21A an UB is an embodiment depicting coated concatemers.

The inner core in this embodiment may be multiple copies of a DNA target that are entwined. The outer layer, i.e., the coating, can include compounds like PEG, compounds with zwitterionic features, ampholine ampholytes, sulphobetaine, and other similar molecules with the positive charges interacting with nucleic acid on the inside and negative charges on the outside the ensure the nanospheres do not clump.

Loading of CATs on the Chip

In some embodiments concatemers are distributed onto an unpatterned surface of a substrate in a high density layer. This close-packed formation facilitates formation of tightly packed sequencing substrates to enable higher throughput and/or lower cost sequencing. In some embodiments, said surface is patterned. An example of a densely packed concatemer layer on an unpatterned surface is shown in FIG. 25.

In some embodiments, concatemers are loaded on a biochip and closely packed to enable a center to center distance of ~250 nm with a variance of +/−25 nm.

In some embodiments, the average center-to-center distance between molecules of about 315 nm. In some embodiments, the plurality of analytes (e.g., nucleic acid molecules) may be deposited adjacent to a surface such that adjacent analytes of the plurality of analytes may have average center-to-center spacings of at least 10 nanometers (nm), nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, or more. The average center-to-center spacings may be less than or equal to 500 nm, 490 nm, 480 nm, 470 nm, 460 nm, 450 nm, 440 nm, 430 nm, 420 nm, 410 nm, 400 nm, 390 nm, 380 nm, 370 nm, 360 nm, 350 nm, 340 nm, 330 nm, 320 nm, 310 nm, 300 nm, 290 nm, 280 nm, 270 nm, 260 nm, 250 nm, 240 nm, 230 nm, 220 nm, 210 nm, 200 nm, 190 nm, 180 nm, 170 nm, 160 nm, 150 nm, 140 nm, 130 nm, 120 nm, 110 nm, 100 nm, 50 nm, or less.

In some embodiments, the concatemers comprise a coating to achieve a lower threshold of center-to-center distances between adjacent concatemers to minimize crosstalk during detection. In some embodiments, after binding the concatemers to the surface, the coating is dissolved and the CATs attached to the surface and can be sequenced.

Another protein such as BSA may be used, either by chemically crosslinking to the CAT or the protein binding partner, or by attaching the spacer protein (e.g. BSA) to an oligonucleotide complementary to the common library adapter sequence through strepavidin interaction. Using BSA to coat the CAT may have the additional benefit of making a protein gel in the bound layer of CATs which may make the local environment for the enzymatic reaction more similar to the natural environment of the nucleus where polymerases normally act.

One may also be able to hybridize long single stranded oligonucleotides that are partially complementary to the common library adapter sequence and extend beyond that sequence without homology. In some embodiments, the long single stranded oligonucleotides are the hairs mentioned above in Paragraph [00113]. Such long oligonucleotides may act to increase the size of the CAT without altering the number of sequencing substrates it contains. After surface attachment, these long oligonucleotides may be washed away, and each CAT may collapse towards the center of its attachment site, increasing the effective center to center distance between adjacent CATs.

DNA may also be used to modify the protein binding partner (by crosslinking or attachments such as strep-avidin) to create a surface that has attractive protein binding sites separated by repellant areas, for instance due to their negative charge.

Deposition of a Closely-Packed Concatemer Layer onto an Unpatterned Surface

One of the limitations to optimum packing density of biological analytes from an aqueous solution onto an unpatterned, adherent solid surface is that the random binding of the analytes onto the surface does not provide for maximal close-packing due to the inability of the adhered analyte to move laterally and minimize spacing between bound molecules. As a result, this random irreversible sticking of analytes produces spacing defects in what may otherwise be arranged into a maximally close-packed array.

However, many biological analytes, including proteins and nucleic acids, are known to be surface active and migrate to the air-water interface that results in a lowering of the surface tension at that interface, to produce a metastable monolayer of biomolecules. In this case, the surface-active analytes are free to move laterally at the interface and achieve a maximal close-packed density, with unfavorable hydrophobic interactions in solution being the driving force for maximal packing.

Therefore, in some embodiments, close-packed, spontaneously formed monolayer constructs of biomolecules at the air-water interface can be transferred or deposited onto a solid surface by pulling or dragging a bolus of the biomolecule solution across the solid surface that is already in contact with air. Thereby, the close-packed biomolecule construct at the air-water interface is deposited onto the solid surface from the point of three-phase (air-water solid) contact as the bolus moves across the solid surface.

In some embodiments, a protein layer may be laid down on the surface before the CATs are added. Then the CATs may be added to the already laid down protein layer. This sequential addition may be particularly effective if the binding protein is the modified partner.

Sequencing

Sequencing Work Flow

In some embodiments, provided herein are methods to detect the sequences of polynucleotides from the concatemers, e.g., through forming a densely-packed layer on an unpatterned surface and performing cycled sequencing by synthesis (see, e.g., FIG. 23). In some embodiments, said surface is patterned.

The detection of targets and their authentication based on repeat hybridizations is a key feature enabling target identification and counting for quantification.

Syncing and Signal Calling (ddNTP Capping of Unreacted Oligonucleotides)

In some embodiments, the sequencing by synthesis includes addition of an irreversible ddNTP terminator after an extension cycle to cap unextended oligonucleotides. For example, after getting maximal initiation and/or extension with mixture of labeled and cold reversible terminators, a cycle of extension (e.g., with a different polymerase that can, better incorporate ddNTPs) and very high concentrations of all four ddNTPs. This operation may irreversibly terminate the extension of any sequencing template within a CAT that failed to extend at the cycle in question. Although this may lead to progressive loss of signal, proportional to the inefficiency of initiation or extension, importantly it may also reduce background at subsequent cycles of those templates within the CAT that 'skipped' extension at any cycle, a process which results in mixed signal from lagging synthesis on some of the identical templates within the CAT.

This process may lead to increased synchronization of templates within a CAT, yielding less signal from lagging templates, so purer signal from the correct base in the sequence. All other things being equal, it may lead to longer effective sequence reads.

Reaction

The CATs have several identical copies of the target DNA, but the last copy made during rolling circle amplification is unique in that it contains an actively extending 3' end. This ssCircle and its actively extending end are likely to be near the center of the ball of DNA that is the CAT, so it is near the center of the exclusion zone within the monolayer of CATs. It is also away from the surface on which that monolayer is formed. Raising the actively extending end away from the surface may increase the accessibility for the chemicals and enzymes used in the sequencing reaction, and also perhaps raise the dye labels above the focal plane of background fluorescence on the surface. These properties make it ideal for single-molecule sequencing.

Paired End Sequencing

UMI Embodiment

Unique Molecular identifiers (UMIs) have been used to tag molecules to enable identification of duplicate PCR products and also to enable double stranded sequencing applications that reduce error.

In some embodiments, adapters that contain UMIs are incorporated into the circularized DNA template used to form the concatemer.

Figure 24:
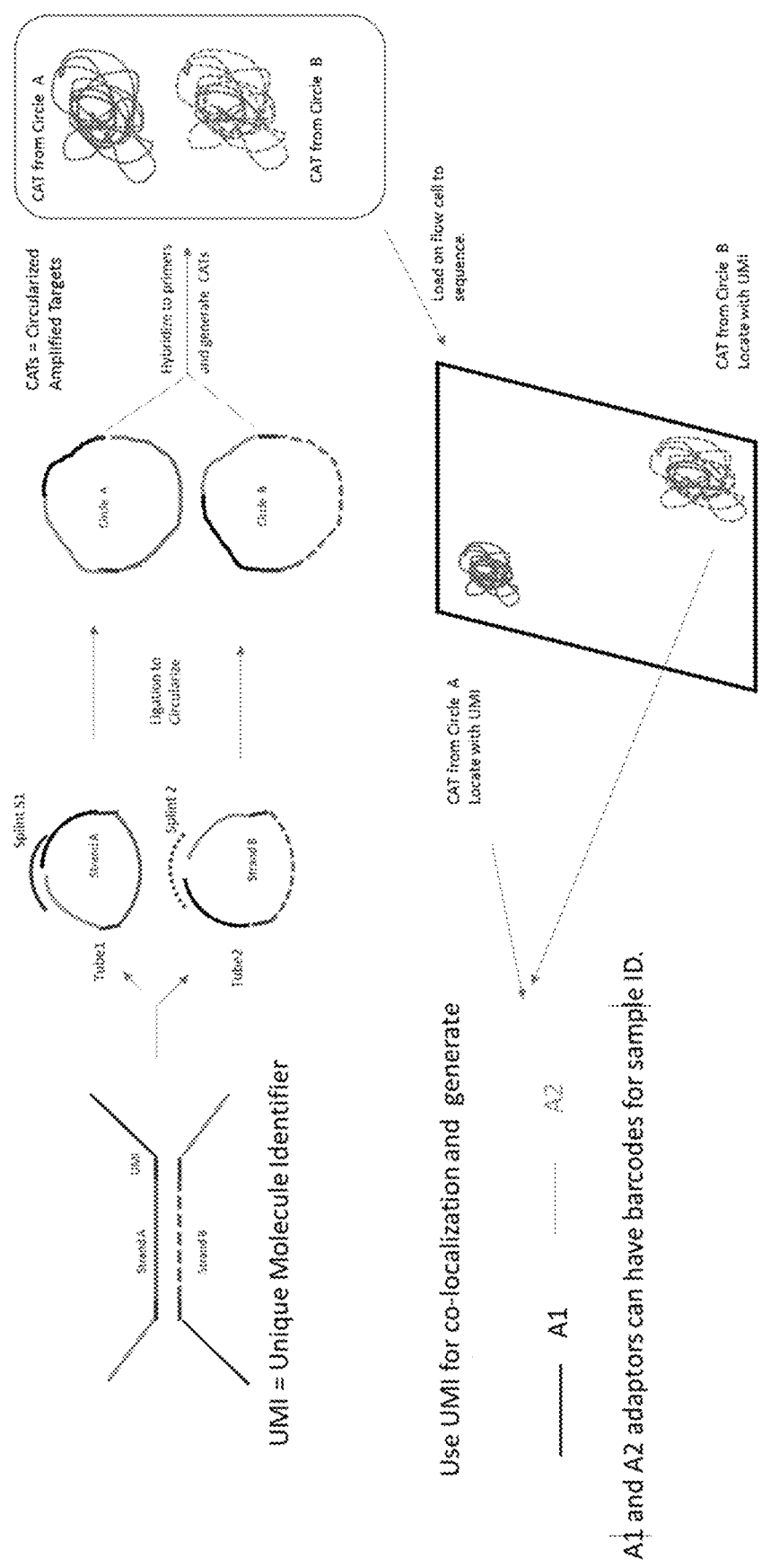
FIG. 24 depicts an embodiment of the use of a unique molecule identifier to include source information (or other information) in each concatemer, according to an embodiment of the present disclosure.

In one embodiment, UMI A1 and A2 adaptors are added to the 5' and 3' ends of Strand A and B, as shown in FIG. 24. A1 and A2 can have barcodes for sample ID. They also have regions used for ligation/circle generation and sequencing primer binding regions to enable sequencing both strands. The adaptors may also have the UMI sequences.

After the completion of sequencing the UMIs can be used to locate circles emanating from the same DNA fragment and analyzed as paired end reads. Paired end reads are useful for mapping if the read lengths are short.

Although UMI may be used, many applications, such as NIPT, PCR amplified panels, and large portions of the genome can be reliably sequenced without having paired end capability.

Imaging and Cycled Detection

As described herein, each of the detection methods and systems required cycled detection to achieve sub-diffraction limited imaging. Cycled detection includes the binding and imaging or probes, such as antibodies or nucleotides, bound to detectable labels that can emit a visible light optical signal. By using positional information from a series of images of a field from different cycles, deconvolution to resolve signals from densely packed substrates can be used effectively to identify individual optical signals from signals obscured due to the diffraction limit of optical imaging. After multiple cycles the precise location of the molecule may become increasingly more accurate. Using this information additional calculations can be performed to aid in crosstalk correction regarding known asymmetries in the crosstalk matrix occurring due to pixel discretization effects.

Methods for Optical Detection of Analytes

In some embodiments, optical signals are digitized, and analytes are identified based on a code (ID code) of digital signals for each analyte.

As described herein, analytes are deposited to a solid substrate, and probes are bound to the analytes. Each of the probes comprises tags and specifically binds to a target analyte. In some embodiments, the tags are fluorescent molecules that emit the same fluorescent color, and the signals for additional fluors are detected at each subsequent pass. During a pass, a set of probes comprising tags are contacted with the substrate allowing them to bind to their targets. An image of the substrate is captured, and the detectable signals are analyzed from the image obtained after each pass. The information about the presence and/or absence of detectable signals is recorded for each detected position (e.g., target analyte) on the substrate.

In some embodiments, the present disclosure comprises methods that include operations for detecting optical signals emitted from the probes comprising tags, counting the signals emitted during multiple passes and/or multiple cycles at various positions on the substrate, and analyzing the signals as digital information using aK-bit based calculation to identify each target analyte on the substrate. Error correction can be used to account for errors in the optically-detected signals, as described below.

In some embodiments, a substrate is bound with analytes comprising N target analytes. To detect N target analytes, M cycles of probe binding and signal detection are chosen. Each of the M cycles includes 1 or more passes, and each pass includes N sets of probes, such that each set of probes specifically binds to one of the N target analytes. In certain embodiments, there are N sets of probes for the N target analytes.

In each cycle, there is a predetermined order for introducing the sets of probes for each pass. In some embodiments, the predetermined order for the sets of probes is a randomized order. In other embodiments, the predetermined order for the sets of probes is a non-randomized order. In one embodiment, the non-random order can be chosen by a computer processor. The predetermined order is represented in a key for each target analyte. A key is generated that includes the order of the sets of probes, and the order of the probes is digitized in a code to identify each of the target analytes.

In some embodiments, each set of ordered probes is associated with a distinct tag for detecting the target analyte, and the number of distinct tags is less than the number of N target analytes. In that case, each N target analyte is matched with a sequence of M tags for the M cycles. The ordered sequence of tags is associated with the target analyte as an identifying code.

Quantification of Optically-Detected Probes

After the detection process, the signals from each probe pool are counted, and the presence or absence of a signal and the color of the signal can be recorded for each position on the substrate.

From the detectable signals, K bits of information are obtained in each of M cycles for the N distinct target analytes. The K bits of information are used to determine L total bits of information, such that $K \times M = L$ bits of information and $L \geq \log 2 (N)$. The L bits of information are used to determine the identity (and presence) of N distinct target analytes. If only one cycle (M=1) is performed, then $K \times 1 = L$. However, multiple cycles (M>1) can be performed to generate more total bits of information L per analyte. Each subsequent cycle provides additional optical signal information that is used to identify the target analyte.

In practice, errors in the signals occur, and this confounds the accuracy of the identification of target analytes. For instance, probes may bind the wrong targets (e.g., false positives) or fail to bind the correct targets (e.g., false negatives). Methods are provided, as described below, to account for errors in optical and electrical signal detection.

Electrical Detection Methods

In other embodiments, electrical detection methods are used to detect the presence of target analytes on a substrate. Target analytes are tagged with oligonucleotide tail regions and the oligonucleotide tags are detected using ion-sensitive field-effect transistors (ISFET, or a pH sensor), which measures hydrogen ion concentrations in solution. ISFETs are described in further detail in U.S. Pat. No. 7,948,015, filed on Dec. 14, 2007, to Rothberg et al., and U.S. Publication No. 2010/0301398, filed on May 29, 2009, to Rothberg et al., which are both incorporated by reference in their entireties.

ISFETs present a sensitive and specific electrical detection system for the identification and characterization of analytes. In one embodiment, the electrical detection methods disclosed herein are carried out by a computer (e.g., a processor). The ionic concentration of a solution can be converted to a logarithmic electrical potential by an electrode of an ISFET, and the electrical output signal can be detected and measured.

ISFETs have previously been used to facilitate DNA sequencing. During the enzymatic conversion of single-stranded (ss) DNA into double-stranded DNA, hydrogen ions are released as each nucleotide is added to the DNA molecule. An ISFET detects these released hydrogen ions and can determine when a nucleotide has been added to the DNA molecule. By synchronizing the incorporation of the nucleoside triphosphate (dATP, dCTP, dGTP, and dTTP), the DNA sequence may also be determined. For example, if no electrical output signal is detected when the single-stranded DNA template is exposed to dATP's, but an electrical output signal is detected in the presence of dGTP's, the DNA sequence is composed of a complementary cytosine base at the position in question.

In one embodiment, an ISFET is used to detect a tail region of a probe and then identify corresponding target analyte. For example, a target analyte can be deposited on a substrate, such as an integrated-circuit chip that contains one or more ISFETs. When the corresponding probe (e.g., aptamer and tail region) is added and specifically binds to the target analyte, nucleotides and enzymes (polymerase) are added for transcription of the tail region. The ISFET detects the release hydrogen ions as electrical output signals and measures the change in ion concentration when the dNTP's are incorporated into the tail region. The amount of hydrogen ions released corresponds to the lengths and stops of the tail region, and this information about the tail regions can be used to differentiate among various tags.

The simplest type of tail region is one composed entirely of one homopolymeric base region. In this case, there are four possible tail regions: a poly-A tail, a poly-C tail, a poly-G tail, and a poly-T tail. However, it is often desirable to have a great diversity in tail regions.

One method of generating diversity in tail regions is by providing stop bases within a homopolymeric base region of a tail region. A stop base is a portion of a tail region comprising at least one nucleotide adjacent to a homopolymeric base region, such that the at least one nucleotide is composed of a base that is distinct from the bases within the homopolymeric base region. In one embodiment, the stop base is one nucleotide. In other embodiments, the stop base comprises a plurality of nucleotides. Generally, the stop base is flanked by two homopolymeric base regions. In an embodiment, the two homopolymeric base regions flanking a stop base are composed of the same base. In another embodiment, the two homopolymeric base regions are composed of two different bases. In another embodiment, the tail region contains more than one stop base.

In one example, an ISFET can detect a minimum threshold number of 100 hydrogen ions. Target Analyte 1 is bound to a composition with a tail region composed of a 100-nucleotide poly-A tail, followed by one cytosine base, followed by another 100-nucleotide poly-A tail, for a tail region length total of 201 nucleotides. Target Analyte 2 is bound to a composition with a tail region composed of a 200-nucleotide poly-A tail. Upon the addition of dTTP's and under conditions conducive to polynucleotide synthesis, synthesis on the tail region associated with Target Analyte 1 may release 100 hydrogen ions, which can be distinguished from polynucleotide synthesis on the tail region associated with Target Analyte 2, which may release 200 hydrogen ions. The ISFET may detect a different electrical output signal for each tail region. Furthermore, if dGTP's are added, followed by more dTTP's, the tail region associated with Target Analyte 1 may then release one, then 100 more hydrogen ions due to further polynucleotide synthesis. The distinct electrical output signals generated from the addition of specific nucleoside triphosphates based on tail region compositions allow the ISFET to detect hydrogen ions from each of the tail regions, and that information can be used to identify the tail regions and their corresponding target analytes.

Various lengths of the homopolymeric base regions, stop bases, and combinations thereof can be used to uniquely tag each analyte in a sample. Additional description about electrical detection of aptamers and tail regions to identify target analytes in a substrate are described in U.S. Provisional Application No. 61/868,988, which is incorporated by reference in its entirety.

In other embodiments, antibodies are used as probes in the electrical detection method described above. The antibodies may be primary or secondary antibodies that bind via a linker region to an oligonucleotide tail region that acts as tag.

These electrical detection methods can be used for the simultaneous detection of hundreds (or even thousands) of distinct target analytes. Each target analyte can be associated with a digital identifier, such that the number of distinct digital identifiers is proportional to the number of distinct target analytes in a sample. The identifier may be represented by a number of bits of digital information and is encoded within an ordered tail region set. Each tail region in an ordered tail region set is sequentially made to specifically bind a linker region of a probe region that is specifically bound to the target analyte. Alternatively, if the tail regions are covalently bonded to their corresponding probe regions, each tail region in an ordered tail region set is sequentially made to specifically bind a target analyte.

In one embodiment, one cycle is represented by a binding and stripping of a tail region to a linker region, such that polynucleotide synthesis occurs and releases hydrogen ions, which are detected as an electrical output signal. Thus, number of cycles for the identification of a target analyte is equal to the number of tail regions in an ordered tail region set. The number of tail regions in an ordered tail region set is dependent on the number of target analytes to be identified, as well as the total number of bits of information to be generated. In another embodiment, one cycle is represented by a tail region covalently bonded to a probe region specifically binding and being stripped from the target analyte.

The electrical output signal detected from each cycle is digitized into bits of information, so that after all cycles have been performed to bind each tail region to its corresponding linker region, the total bits of obtained digital information can be used to identify and characterize the target analyte in question. The total number of bits is dependent on a number of identification bits for identification of the target analyte, plus a number of bits for error correction. The number of bits for error correction is selected based on the desired robustness and accuracy of the electrical output signal. Generally, the number of error correction bits may be 2 or 3 times the number of identification bits.

Decoding the Order and Identity of Detected Analytes

The probes used to detect the analytes are introduced to the substrate in an ordered manner in each cycle. A key is generated that encodes information about the order of the probes for each target analyte. The signals detected for each analyte can be digitized into bits of information. The order of the signals provides a code for identifying each analyte, which can be encoded in bits of information.

Error-Correction Methods

In optical and electrical detection methods described above, errors can occur in binding and/or detection of signals. In some cases, the error rate can be as high as one in five (e.g., one out of five fluorescent signals is incorrect). This equates to one error in every five-cycle sequence. Actual error rates may not be as high as 20%, but error rates of a few percent are possible. In general, the error rate depends on many factors including the type of analytes in the sample and the type of probes used. In an electrical detection method, for example, a tail region may not properly bind to the corresponding probe region on an aptamer during a cycle. In an optical detection method, an antibody probe may not bind to its target or bind to the wrong target.

Additional cycles are generated to account for errors in the detected signals and to obtain additional bits of information, such as parity bits. The additional bits of information are used to correct errors using an error correcting code. In one embodiment, the error correcting code is a Reed-Solomon code, which is a non-binary cyclic code used to detect and correct errors in a system. In other embodiments, various other error correcting codes can be used. Other error correcting codes include, for example, block codes, convolution codes, Golay codes, Hamming codes, BCH codes, AN codes, Reed-Muller codes, Gappa codes, Hadamard codes, Walsh codes, Hagelbarger codes, polar codes, repetition codes, repeat-accumulate codes, erasure codes, online codes, group codes, expander codes, constant-weight codes, tornado codes, low-density parity check codes, maximum distance codes, burst error codes, luby transform codes, fountain codes, and raptor codes. See Error Control Coding, 2nd Ed., S. Lin and DJ Costello, Prentice Hall, New York, 2004. Examples are also provided below that demonstrate the method for error-correction by adding cycles and obtaining additional bits of information.

One example of a Reed-Solomon code includes a RS (15,9) code with 4-bit symbols, where n=15, k=9, s=4, and t=3, and n=2s−1 and k=n−2t, "n" being the number of symbols, "k" being the number of data symbols, "s" being the size of each symbol in bits, and "t" being the number of errors that can be corrected, and "2t" being the number of parity symbols. There are nine data symbols (k=9) and six parity symbols (2t=6). If base-X numbers are used, and X=4, then each fluorescent color is represented by two bits (0 and 1). A pair of colors may be represented by a four-bit symbol that includes two high bits and two low bits.

Since base-4 was chosen, seven probe pools, or a sequence of seven colors, are used to identify each target analyte. This sequence is represented by 3½, 4-bit symbols. The remaining 5½ data symbols are set to zero. A Reed-Solomon RS (15,9) encoder then generates the six parity symbols, represented by 12 additional probe pools. Thus, a total of 19 probe pools (7+12) are required to obtain error correction for t=3 symbols.

Monte Carlo simulations of error-correcting code performance have been performed assuming seven probe pools, to identify up to 16,384 distinct targets. Using these simulations, the maximum permissible raw error rate (associated with identifying a fluorescent label) to achieve a corrected error rate of 10-5 was determined for different numbers of parity bits.

In some embodiments, a key is generated that includes the expected bits of information associated with an analyte (e.g., the expected order of probes and types of signals for the analyte). These expected bits of information for a particular analyte are compared with the actual L bits of information that are obtained from the target analyte. Using the Reed-Solomon approach, an allowance of up to t errors in the signals can be tolerated in the comparison of the expected bits of information and the actual L bits of information.

In some embodiments, a Reed-Solomon decoder is used to compare the expected signal sequence with an observed signal sequence from a particular probe. For example, seven probe pools may be used to identify a target analyte, the expected color sequence being BGGBBYY, represented by 14 bits. Additional parity pools may then be used for error correction. For example, six 4-bit parity symbols may be used.

Methods and systems using cycled probe binding and optical detection are described in US Publication No. 2015/0330974, Digital Analysis of Molecular Analytes Using Single Molecule Detection, published Nov. 19, 2015, and US Publication No. 2018/0252936, High Speed Scanning With Acceleration Tracking, published Sep. 6, 2018, are each incorporated herein by reference herein in its entirety.

In some embodiments, the raw images are obtained using sampling that is at least at the Nyquist limit to facilitate more accurate determination of the oversampled image. Increasing the number of pixels used to represent the image by sampling in excess of the Nyquist limit (oversampling) increases the pixel data available for image processing and display.

Theoretically, a bandwidth-limited signal can be perfectly reconstructed if sampled at the Nyquist rate or above it. The Nyquist rate is defined as twice the highest frequency component in the signal. Oversampling improves resolution, reduces noise and helps avoid aliasing and phase distortion by relaxing anti-aliasing filter performance requirements. A signal is said to be oversampled by a factor of N if it is sampled at N times the Nyquist rate.

Thus, in some embodiments, each image is taken with a pixel size no more than half the wavelength of light being observed. In some embodiments, a pixel size of less than about 200 nm×200 nm is used in detection to achieve sampling at or above the Nyquist limit. Sampling at a frequency of at least the Nyquist limit during raw imaging of the substrate is preferred to optimize the resolution of the system or methods described herein. This can be done in conjunction with the deconvolution methods and optical systems described herein to resolve features on a substrate below the diffraction limit with high accuracy.

Processing Images from Different Cycles

There are several barriers overcome by the present invention to achieve sub-diffraction limited imaging.

Pixelation error is present in raw images and prevents identification of information present from the optical signals due to pixelation. Sampling at least at the Nyquist frequency and generation of an oversampled image as described herein each assist in overcoming pixilation error.

The point-spread (PSF) of various molecules overlap because the PSF size is greater than the pixel size (below Nyquist) and because the center-to-center spacing is so small that crosstalk due to spatial overlap occurs. Nearest neighbor e.g. variable regression (for center-to center crosstalk correction) can be used to help with deconvolution of multiple overlapping optical signals. But this can be improved if we know the relative location of each analyte on the substrate and have good alignment of images of a field. In some embodiments, machine learning (e.g. artificial intelligence or "A.I.") can be used to help with deconvolution of multiple overlapping optical signals. In some embodiments, the machine learning processes input data over multiple cycles of probe binding and imaging to deconvolve further images.

After multiple cycles the precise location of the molecule may become increasingly more accurate. Using this information additional calculations can be performed to aid in deconvolution by correcting for known asymmetries in the spatial overlap of optical signals occurring due to pixel discretization effects and the diffraction limit. They can also be used to correct for overlap in emission spectrum from different emission spectrum.

Highly accurate relative positional information for each analyte can be achieved by overlaying images of the same field from different cycles to generate a distribution of measured peaks from optical signals of different probes bound to each analyte. This distribution can then be used to generate a peak signal that corresponds to a single relative location of the analyte. Images from a subset of cycles can be used to generate relative location information for each analyte. In some embodiments, this relative position information is provided in a localization file.

The specific area imaged for a field for each cycle may vary from cycle to cycle. Thus, to improve the accuracy of identification of analyte position for each image, an alignment between images of a field across multiple cycles can be performed. From this alignment, offset information compared to a reference file can then be identified and incorporated into the deconvolution algorithms to further increase the accuracy of deconvolution and signal identification for optical signals obscured due to the diffraction limit. In some embodiments, this information is provided in a Field Alignment File.

Signal Detection (Cross-Talk/Nearest Neighbor)

Once relative positional information is accurately determined for analytes on a substrate and field images from each cycle are aligned with this positional information, analysis of each oversampled image using crosstalk and nearest neighbor regression can be used to accurately identify an optical signal from each analyte in each image.

In some embodiments, a plurality of optical signals obscured by the diffraction limit of the optical system are identified for each of a plurality of biomolecules deposited on a substrate and bound to probes comprising a detectable label. In some embodiments, the probes are incorporated nucleotides and the series of cycles is used to determine a sequence of a polynucleotide deposited on the array using sequencing by synthesis.

Simulations of Deconvolution Applied to Images

Figure 3:
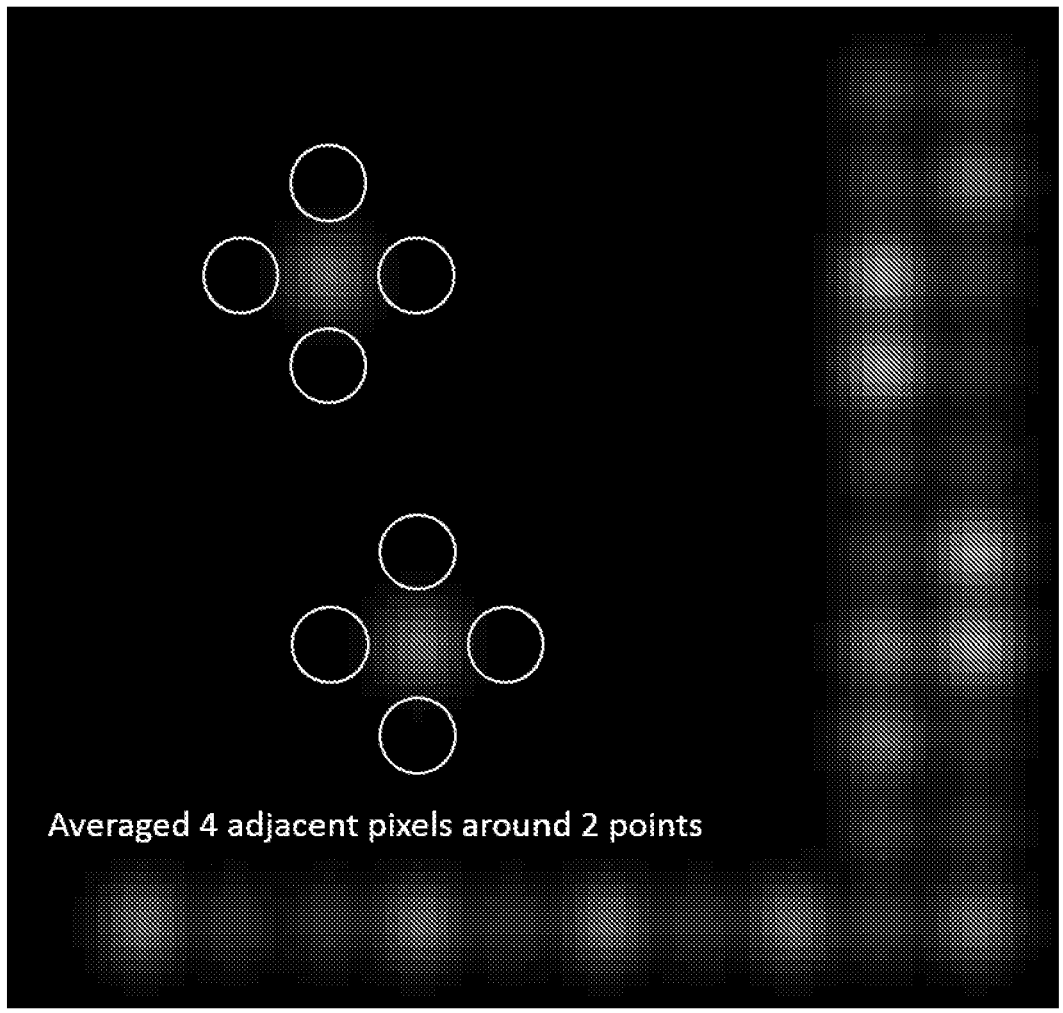
FIG. 3 shows crosstalk calculations for simulated detection of individual analytes on a 600 nm pitch processed with a 2× filter.

Molecular densities are limited by crosstalk from neighboring molecules. FIG. 3 depicts simulated images of single analytes. This particular image is a simulation of a layer of analytes on a 600 nm pitch that has been processed with a 2× oversampled filter. Crosstalk into eight adjacent spots is averaged as a function of array pitch and algorithm type.

Figure 4:
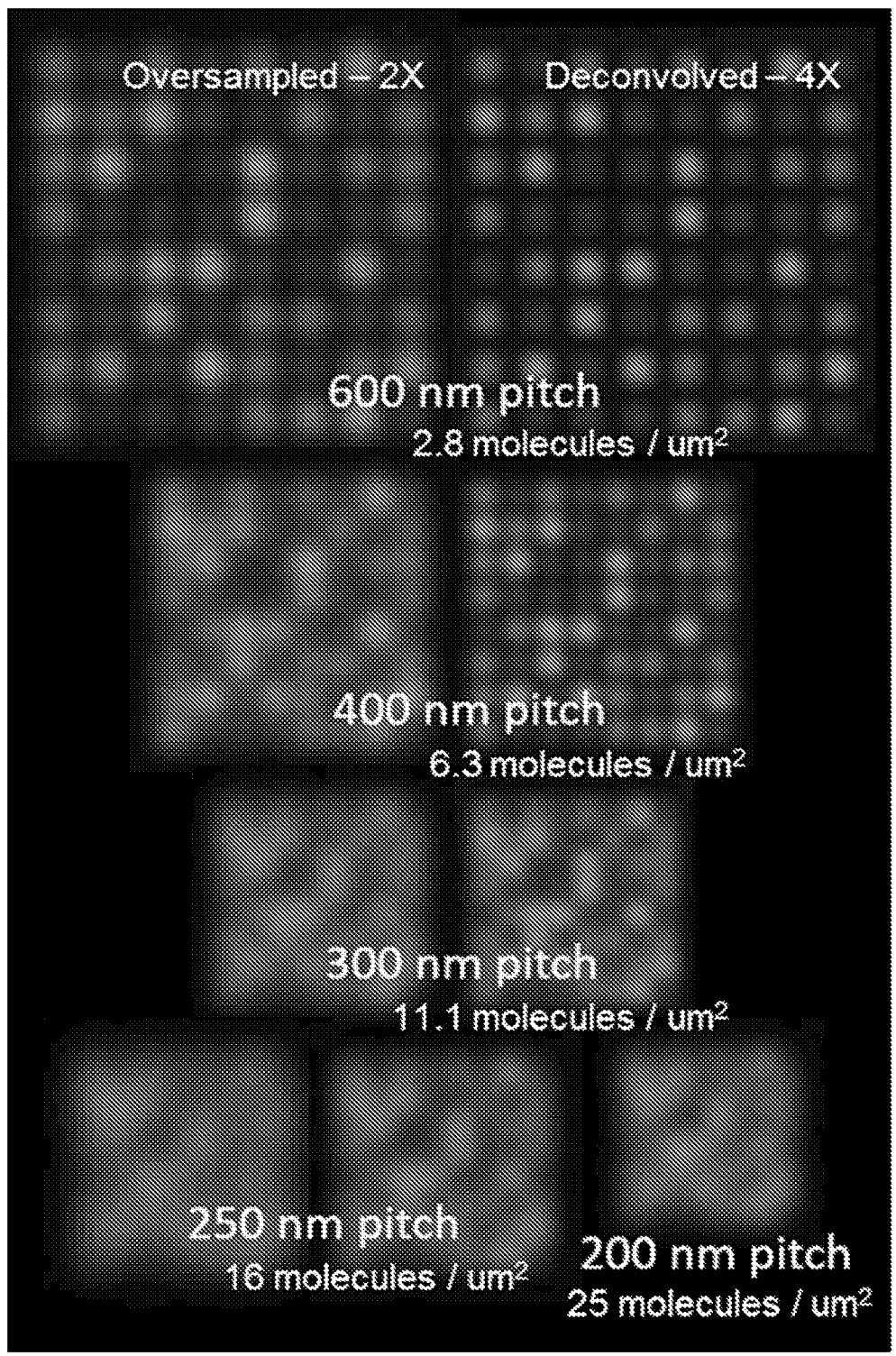
FIG. 4 shows Oversampled 2× (left) vs. Oversampled 4× and Deconvolved (right) simulations of images of detection of single analytes on a substrate at center-to-center distances of 400 nm, 300 nm, and 250 nm. A single image of Oversampled 4× and Deconvolved at a center-to-center distance of 200 nm is also shown.
Figure 5:
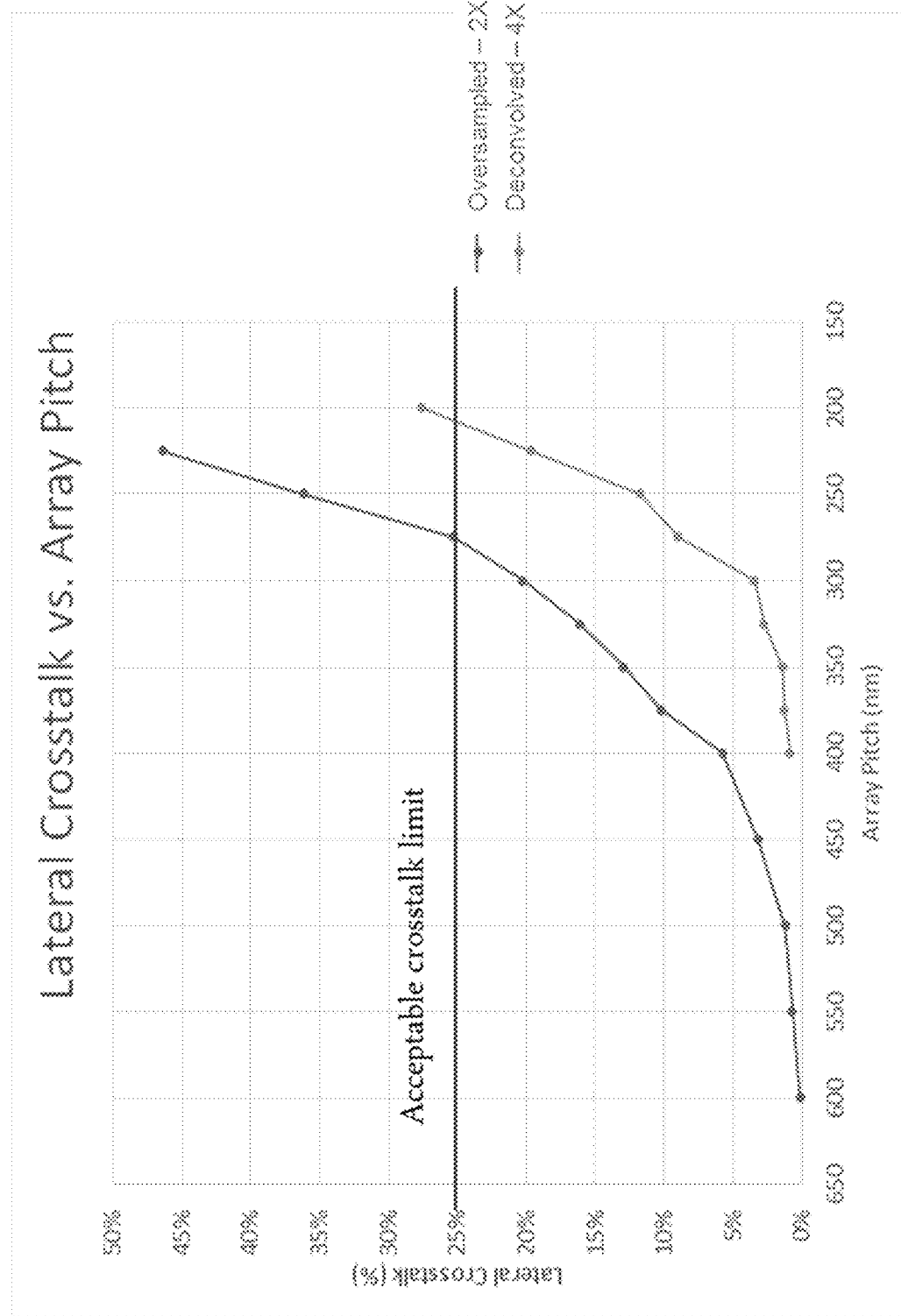
FIG. 5 shows a plot of crosstalk between adjacent spots at different center-to-center distances between single analytes (array pitch (nm)) processed using Oversampled 2× vs. Oversampled 4× and Deconvolved simulations.

FIG. 4 is a series of images processed with multiple pitches and two variations of image processing algorithms, the first is a 2× oversampled image and the second is a 4× oversampled image with deconvolution, as described herein. FIG. 5 is the crosstalk analysis of these two types of image processing at pitches down to 200 nm. Acceptable crosstalk levels at or below 25% with 2× oversample occurs for pitches at or above 275 nm. Acceptable crosstalk levels at or below 25% with 4× deconvolution using the point spread function of the optical system occurs for pitches at or above 210 nm.

The physical size of the molecule may broaden the spot roughly half the size of the binding area. For example, for an 80 nm spot the pitch may be increased by roughly 40 nm. Smaller spot sizes may be used, but this may have the trade-off that fewer copies may be allowed and greater illumination intensity may be required. A single copy provides the simplest sample preparation but requires the greatest illumination intensity.

Methods for sub-diffraction limit imaging discussed to this point involve image processing techniques of oversampling, deconvolution and crosstalk correction. Described herein are methods and systems that incorporate determination of the precise relative location analytes on the substrate using information from multiple cycles of probe optical signal imaging for the analytes. Using this information additional calculations can be performed to aid in crosstalk correction regarding known asymmetries in the crosstalk matrix occurring due to pixel discretization effects.

Methods

Figure 6:
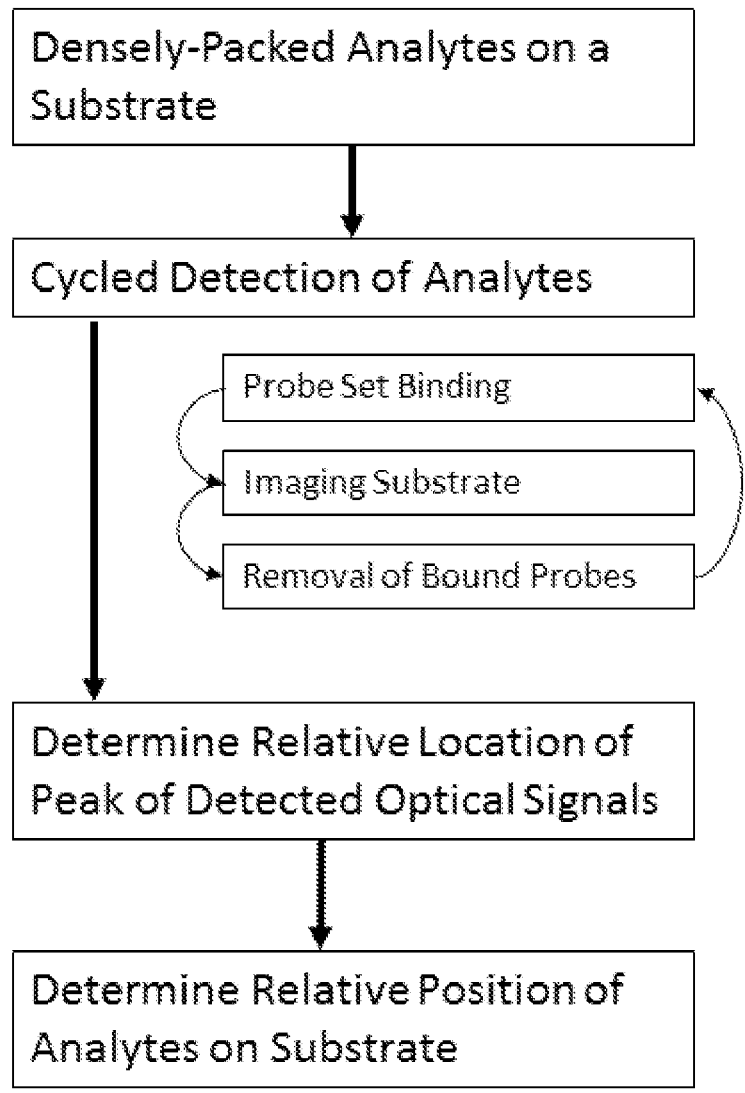
FIG. 6 depicts a flowchart for a method of determining the relative positions of analytes on a substrate with high accuracy, according to an embodiment of the present disclosure.

In some embodiments, as shown in FIG. 6, provided herein is a method for accurately determining a relative position of analytes deposited on the surface of a densely packed substrate. The method includes first providing a substrate comprising a surface, wherein the surface comprises a plurality of analytes deposited on the surface at discrete locations. Then, a plurality of cycles of probe binding and signal detection on said surface is performed. Each cycle of detection includes contacting the analytes with a probe set capable of binding to target analytes deposited on the surface, imaging a field of said surface with an optical system to detect a plurality of optical signals from individual probes bound to said analytes at discrete locations on said surface, and removing bound probes if another cycle of detection is to be performed. From each image, a peak location from each of said plurality of optical signals from images of said field from at least two (i.e., a subset) of said plurality of cycles is detected. The location of peaks for each analyte is overlaid, generating a cluster of peaks from which an accurate relative location of each analyte on the substrate is then determined.

Figure 7:
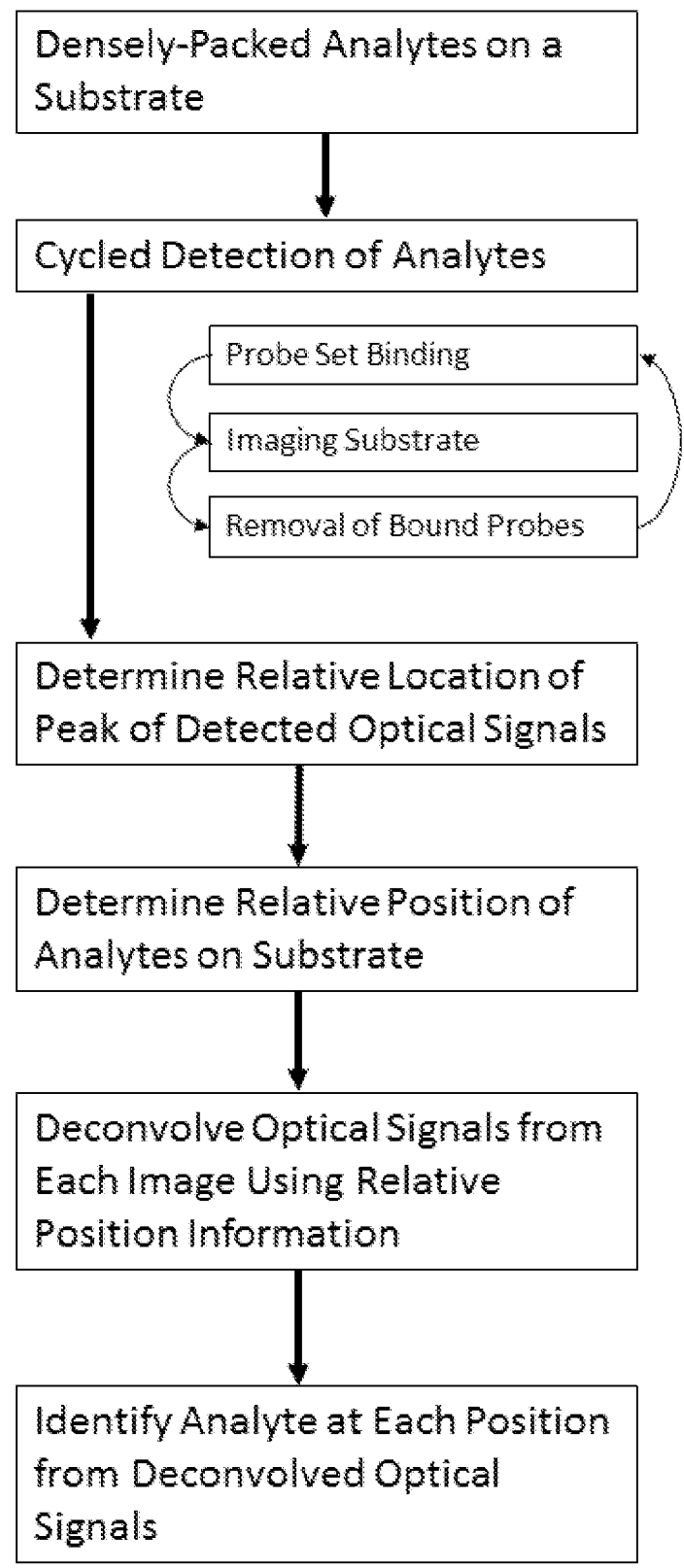
FIG. 7 depicts a flowchart for a method of identifying individual analytes from deconvolved optical signals detected from a substrate, according to an embodiment of the present disclosure.

In some embodiments, as shown in FIG. 7, the accurate position information for analytes on the substrate is then used in a deconvolution algorithm incorporating position information (e.g., for identifying center-to-center spacing between neighboring analytes on the substrate) can be applied to the image to deconvolve overlapping optical signals from each of said images. In some embodiments, the deconvolution algorithm includes nearest neighbor variable regression for spatial discrimination between neighboring analytes with overlapping optical signals.

Figure 8:
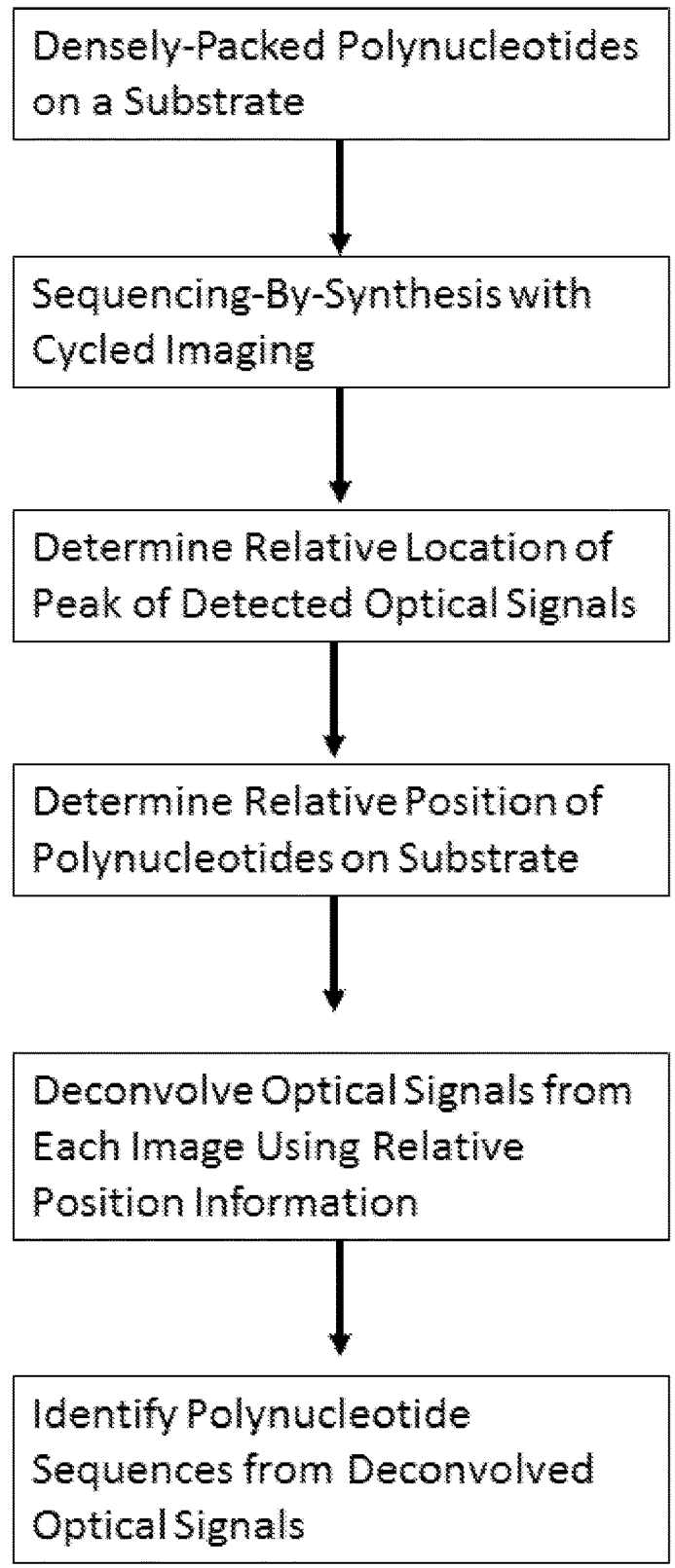
FIG. 8 depicts a flowchart for a method of sequencing polynucleotides deposited on a substrate, according to an embodiment of the present disclosure.

In some embodiments, as shown in FIG. 8, the method of analyte detection is applied for sequencing of individual polynucleotides deposited on a substrate.

Figure 9:
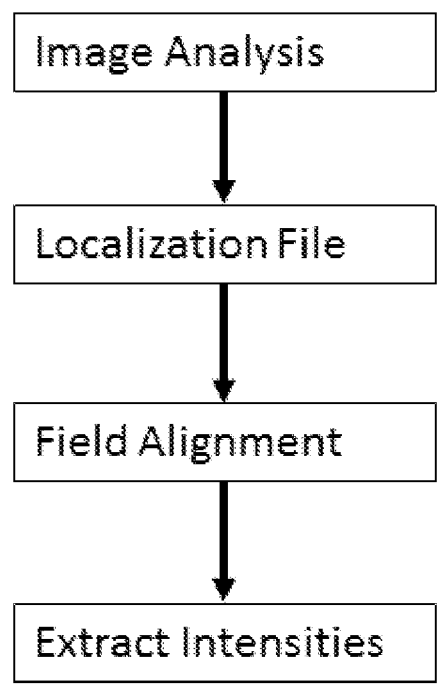
FIG. 9 shows an overview of operations in an optical signal detection process from cycled detection, according to an embodiment of the present disclosure.
Figure 11:
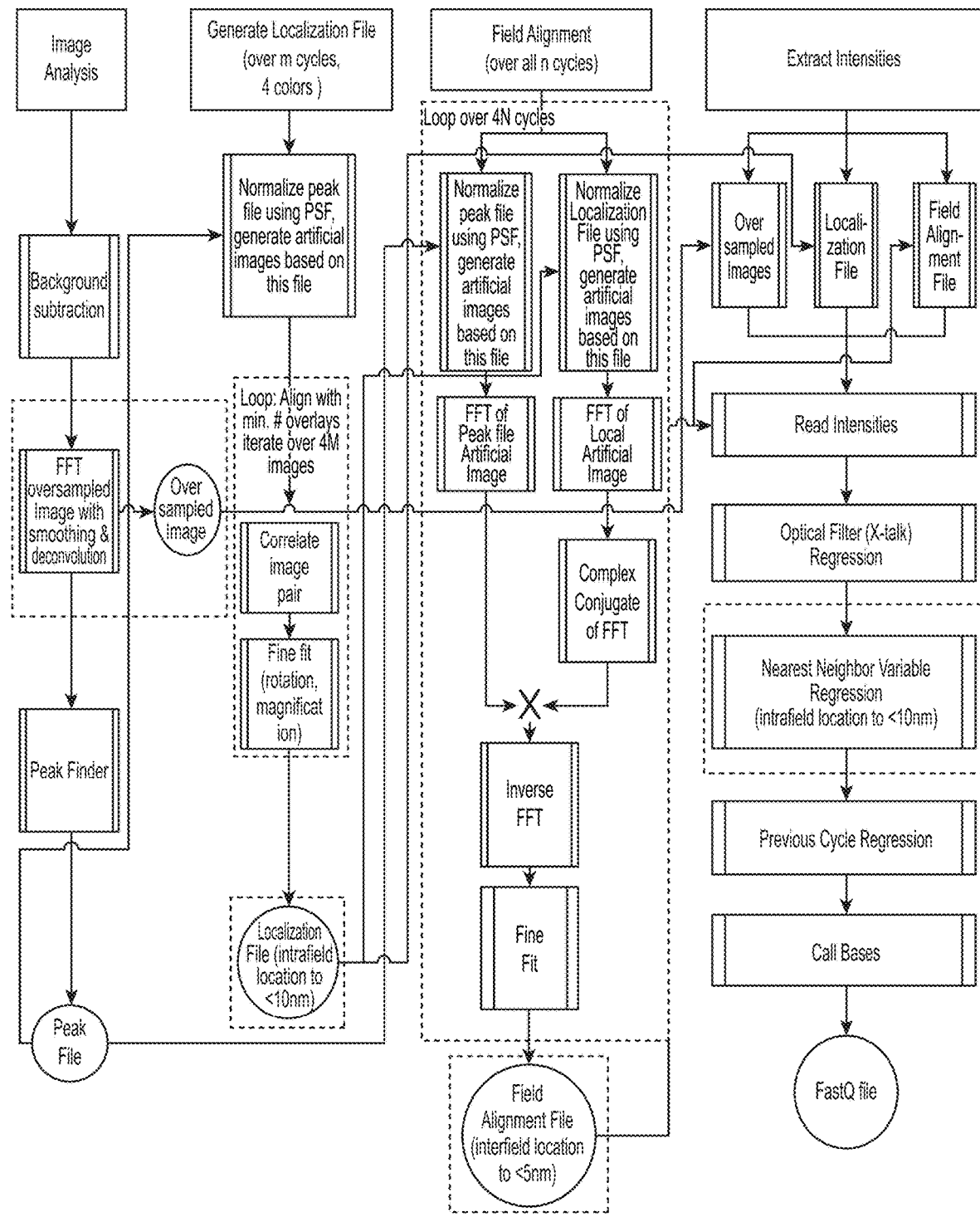
FIG. 11 depicts a detailed flowchart of operations for an optical signal detection and deconvolution process for images from cycled detection of a densely-packed substrate, according to an embodiment of the present disclosure.

In some embodiments, optical signals are deconvolved from densely packed substrates as shown in FIG. 11. The operations can be divided into four different sections as shown in FIG. 9: 1) Image Analysis, which includes generation of oversampled images from each image of a field for each cycle, and generation of a peak file (i.e., a data set) including peak location and intensity for each detected optical signal in an image. 2) Generation of a Localization File, which includes alignment of multiple peaks generated from the multiple cycles of optical signal detection for each analyte to determining an accurate relative location of the analyte on the substrate. 3) Generation of a Field Alignment file, which includes offset information for each image to align images of the field from different cycles of detection with respect to a selected reference image. 4) Extract Intensities, which uses the offset information and location information in conjunction with deconvolution modeling to determine an accurate identity of signals detected from each oversampled image. The "Extract Intensities" operation can also include other error correction, such as previous cycle regression used to correct for errors in sequencing by synthesis processing and detection. The operations performed in each section are described in further detail below.

Under the image analysis operations shown in FIG. 10A and FIG. 11, the images of each field from each cycle are processed to increase the number of pixels for each detected signal, sharpen the peaks for each signal, and identify peak intensities form each signal. This information is used to generate a peak file for each field for each cycle that includes a measure of the position of each analyte (from the peak of the observed optical signal), and the intensity, from the peak intensity from each signal. In some embodiments, the image from each field first undergoes background subtraction to perform an initial removal of noise from the image. Then, the images are processed using smoothing and deconvolution to generate an oversampled image, which includes artificially generated pixels based on modeling of the signal observed in each image. In some embodiments, the oversampled image can generate 4 pixels, 9 pixels, or 16 pixels from each pixel from the raw image.

Peaks from optical signals detected in each raw image or present in the oversampled image are then identified and intensity and position information for each detected analyte is placed into a peak file for further processing.

In some embodiments, N raw images corresponding to all images detected from each cycle and each field of a substrate or output into N oversampled images and N peak files for each imaged field. The peak file comprises a relative position of each detected analyte for each image. In some embodiments, the peak file also comprises intensity information for each detected analyte. In some embodiments, one peak file is generated for each color and each field in each cycle. In some embodiments, each cycle further comprises multiple passes, such that one peak file can be generated for each color and each field for each pass in each cycle. In some embodiments, the peak file specifies peak locations from optical signals within a single field.

In preferred embodiments, the peak file includes XY position information from each processed oversampled image of a field for each cycle. The XY position information comprises estimated coordinates of the locations of each detected detectable label from a probe (such as a fluorophore) from the oversampled image. The peak file can also include intensity information from the signal from each individual detectable label.

Generation of an oversampled image is used to overcome pixelation error to identify information present that cannot be extracted due to pixelation. Initial processing of the raw image by smoothing and deconvolution helps to provide more accurate information in the peak files so that the position of each analyte can be determined with higher accuracy, and this information subsequently can be used to provide a more accurate determination of signals obscured in diffraction limited imaging.

In some embodiments, the raw images are obtained using sampling that is at least at the Nyquist limit to facilitate more accurate determination of the oversampled image. Increasing the number of pixels used to represent the image by sampling in excess of the Nyquist limit (oversampling) increases the pixel data available for image processing and display.

Theoretically, a bandwidth-limited signal can be perfectly reconstructed if sampled at the Nyquist rate or above it. The Nyquist rate is defined as twice the highest frequency component in the signal. Oversampling improves resolution, reduces noise and helps avoid aliasing and phase distortion by relaxing anti-aliasing filter performance requirements. A signal is said to be oversampled by a factor of N if it is sampled at N times the Nyquist rate.

Thus, in some embodiments, each image is taken with a pixel size no more than half the wavelength of light being observed. In some embodiments, a pixel size of less than about 200 nm×200 nm is used in detection to achieve sampling at or above the Nyquist limit.

Smoothing uses an approximating function capture important patterns in the data, while leaving out noise or other fine-scale structures/rapid phenomena. In smoothing, the data points of a signal are modified so individual points are reduced, and points that are lower than the adjacent points are increased leading to a smoother signal. Smoothing is used herein to smooth the diffraction limited optical signal detected in each image to better identify peaks and intensities from the signal.

Although each raw image is diffraction limited, described herein are methods that result in collection of multiple signals from the same analyte from different cycles. An embodiment of this method is shown in the flowchart in FIG. 10B. These multiple signals from each analyte are used to determine a position much more accurate than the diffraction limited signal from each individual image. They can be used to identify molecules within a field at a resolution of less than 5 nm. This information is then stored as a localization file, as shown in FIG. 11. The highly accurate position information can then be used to greatly improve signal identification from each individual field image in combination with deconvolution algorithms, such as cross-talk regression and nearest neighbor variable regression.

As shown in FIG. 11, the operations for generating a localization file use the location information provided in the peak files to determine relative positions of a set of analytes on the substrate. In some embodiments, each localization file contains relative positions from sets of analytes from a single imaged field of the substrate. The localization file combines position information from multiple cycles to generate highly accurate position information for detected analytes below the diffraction limit.

In some embodiments, the relative position information for each analyte is determined on average to less than a 10 nm standard deviation (i.e., RMS, or root mean square). In some embodiments, the relative position information for each analyte is determined on average to less than a 10 nm 2× standard deviation. In some embodiments, the relative position information for each analyte is determined on average to less than a 10 nm 3× standard deviation. In some embodiments, the relative position information for each analyte is determined to less than a 10 nm median standard deviation. In some embodiments, the relative position information for each analyte is determined to less than a 10 nm median 2× standard deviation. In some embodiments, the relative position information for each analyte is determined to less than a 10 nm median 3× standard deviation.

From a subset of peak files for a field from different cycles, a localization file is generated to determine a location of analytes on the array. As shown in FIG. 11, in some embodiments, a peak file is first normalized using a point spread function to account for aberrations in the optical system. The normalized peak file can be used to generate an artificial normalized image based on the location and intensity information provided in the peak file. Each image is then aligned. In some embodiments, the alignment can be performed by correlating each image pair and performing a fine fit. Once aligned, position information for each analyte from each cycle can then be overlaid to provide a distribution of position measurements on the substrate. This distribution is used to determine a single peak position that provides a highly accurate relative position of the analyte on the substrate. In some embodiments, a Poisson distribution is applied to the overlaid positions for each analyte to determine a single peak.

The peaks determined from at least a subset of position information from the cycles are then recorded in a localization file, which comprises a measure of the relative position of each detected analyte with an accuracy below the diffraction limit. As described, images from only subset of cycles are needed to determine this information.

As shown in FIG. 11, a normalized peak file from each field for each cycle and color and the normalized localization file can be used to generate offset information for each image from a field relative to a reference image of the field. This offset information can be used to improve the accuracy of the relative position determination of the analyte in each raw image for further improvements in signal identification from a densely packed substrate and a diffraction limited image. In some embodiments, this offset information is stored as a field alignment file. In some embodiments, the position information of each analyte in a field from the combined localization file and field alignment file is less than 10 nm RMS, less than 5 nm RMS, or less than 2 nm RMS.

In some embodiments, a field alignment file is generated by alignment of images from a single field by determining offset information relative to a master file from the field. One field alignment file is generated for each field. This file is generated from all images of the field from all cycles, and includes offset information for all images of the field relative to a reference image from the field.

In some embodiments, before alignment, each peak file is normalized with a point spread function, followed by generation of an artificial image from the normalized peak file and Fourier transform of the artificial image. The Fourier transform of the artificial image of the normalized peak file is then convolved with a complex conjugate of the Fourier transform of an artificial image from the normalized localization file for the corresponding field. This is done for each peak file for each cycle. The resulting files then undergo an inverse Fourier transform to regenerate image files, and the image files are aligned relative to the reference file from the field to generate offset information for each image file. In some embodiments, this alignment includes a fine fit relative to a reference file.

The field alignment file thus contains offset information for each oversampled image, and can be used in conjunction with the localization file for the corresponding field to generate highly accurate relative position for each analyte for use in the subsequent "Extract Intensities" operations.

As an example where 20 cycles are performed on a field, and one image is generated for each of 4 colors to be detected, thus generating 80 images of the field, one Field Alignment file is generated for all 80 images (20 cycles*4 colors) taken of the field. In some embodiments, the field alignment file contents include: the field, the color observed for each image, the operation type in the cycled detection (e.g., binding or stripping), and the image offset coordinates relative to the reference image.

In some embodiments, during the alignment process XY "shifts" or "residuals" needed to align 2 images are calculated, and the process is repeated for remaining images, best fit residual to apply to all is calculated.

Figure 10C:
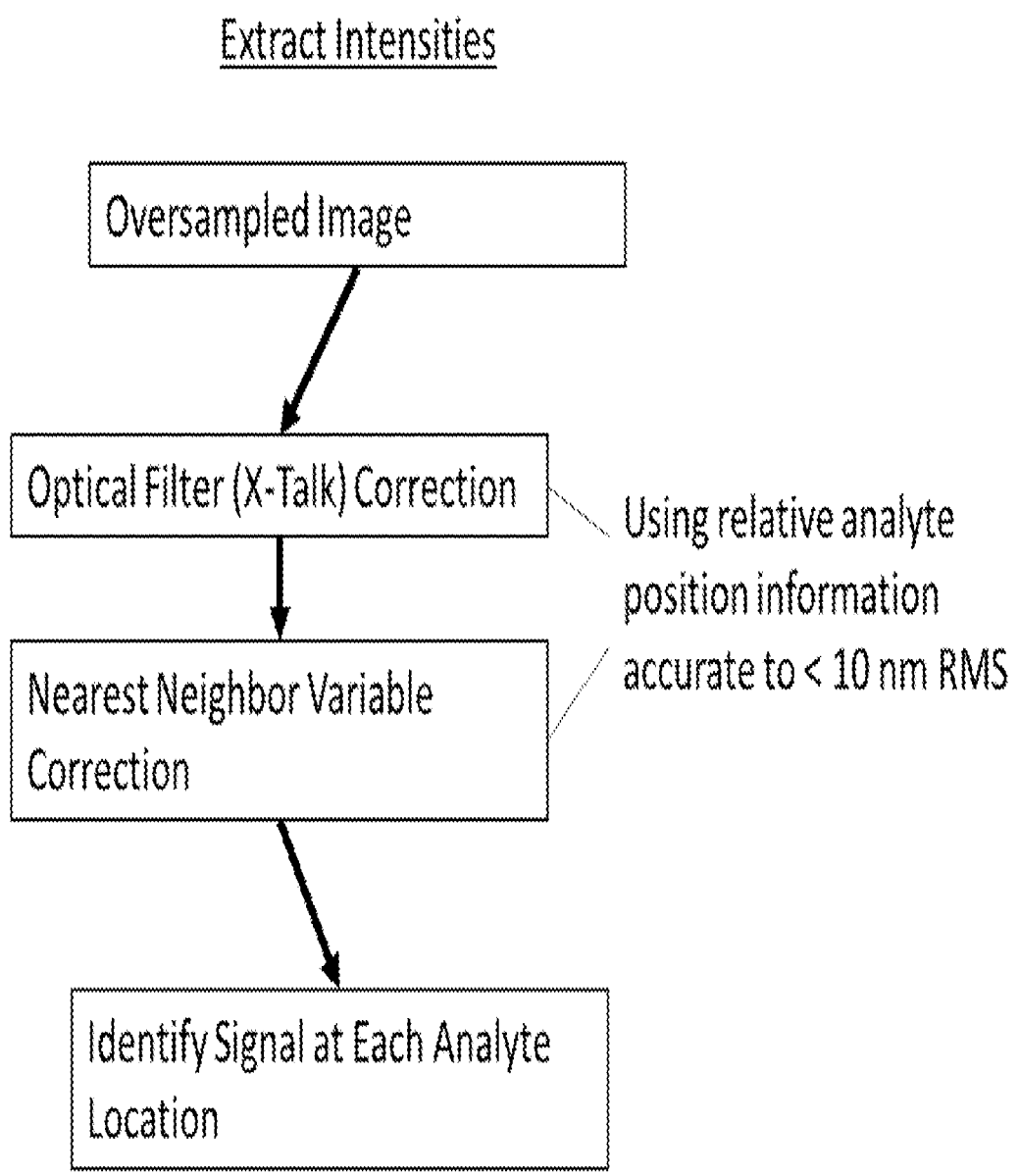
FIG. 10C shows a flowchart of operations for identification of overlapping optical signals from an image using accurate relative positional information and image deconvolution algorithms, according to an embodiment of the present disclosure.

In some embodiments, residuals that exceed a threshold are thrown out, and best fit is re-calculated. This process is repeated until all individual residuals are within the threshold Each oversampled image is then deconvolved using the accurate position information from the localization file and the offset information from the field alignment file. An embodiment of the intensity extraction operation is shown in FIG. 10C and FIG. 11. The Point Spread Function (PSF) of various molecules overlap because the center-to-center spacing is so small that the point-spread function of signals from adjacent analytes overlaps. Nearest neighbor variable regression in combination with the accurate analyte position information and/or offset information can be used to deconvolve signals from adjacent analytes that have a center-to-center distance that inhibits resolution due to the diffraction limit. The use of the accurate relative position information for each analyte facilitates spatial deconvolution of optical signals from neighboring analytes below the diffraction limit. In some embodiments, the relative position of neighboring analytes is used to determine an accurate center-to-center distance between neighboring analytes, which can be used in combination with the point spread function of the optical system to estimate spatial cross-talk between neighboring analytes for use in deconvolution of the signal from each individual image. This enables the use of substrates with a density of analytes below the diffraction limit for optical detection techniques, such as polynucleotide sequencing.

In certain embodiments, emission spectra overlap between different signals (i.e. "cross-talk"). For example, during sequencing by synthesis, the four dyes used in the sequencing process typically have some overlap in emission spectra.

In particular embodiments, a problem of assigning a color (for example, a base call) to different features in a set of images obtained for a cycle when crosstalk occurs between different color channels and when the crosstalk is different for different sets of images can be solved by cross-talk regression in combination with the localization and field alignment files for each oversampled image to remove overlapping emission spectrums from optical signals from each different detectable label used. This further increases the accuracy of identification of the detectable label identity for each probe bound to each analyte on the substrate.

Thus, in some embodiments, identification of a signal and/or its intensity from a single image of a field from a cycle as disclosed herein uses the following features: 1) Oversampled Image—provides intensities and signals at defined locations. 2) Accurate Relative Location—Localization File (provides location information from information from at least a subset of cycles) and Field Alignment File (provides offset/alignment information for all images in a field). 3) Image Processing—Nearest Neighbor Variable Regression (spatial deconvolution) and Cross-talk regression (emission spectra deconvolution) using accurate relative position information for each analyte in a field. Accurate identification of probes (e.g., antibodies for detection or complementary nucleotides for sequencing) for each analyte.

Image Processing Simulations

The effects of the methods and systems disclosed herein are illustrated in simulated cross-talk plots shown in FIG. 12A, FIG. 12B, FIG. 13A and FIG. 13B. For each of these figures, a cross-talk plot showing the intensity of emission spectrum correlated with one of four fluorophores at each detected analyte in a 10 um×10 um region is shown. Each axis corresponding to one of the four fluorophores extends to each corner of the plot. Thus, a spot located in the center of the plot may have equal contribution of intensity from all four fluorophores. Emission intensity detected from an individual fluorophore during an imaging cycle is assigned to move the spot in a direction either towards X, Y; X, -Y; -X, Y; or -X, ¬Y. Thus, separation of populations of spots along these four axes indicates a clear deconvolved signal from a fluorophore at an analyte location. Each simulation is based on detection of 1024 molecules in a 10.075 um×10.075 um region, indicating a density of 10.088 molecules per micron squared, or an average center-to-center distance between molecules of about 315 nm. This is correlated with an imaging region of about 62×62 pixels at a pixel size of less than about 200 nm×200 nm.

In some embodiments, the average center-to-center distance between molecules is about 150 nm to about 500 nm. In some embodiments, the average center-to-center distance between molecules is about 150 nm to about 175 nm, about 150 nm to about 200 nm, about 150 nm to about 225 nm, about 150 nm to about 250 nm, about 150 nm to about 275 nm, about 150 nm to about 300 nm, about 150 nm to about 325 nm, about 150 nm to about 350 nm, about 150 nm to about 375 nm, about 150 nm to about 400 nm, about 150 nm to about 500 nm, about 175 nm to about 200 nm, about 175 nm to about 225 nm, about 175 nm to about 250 nm, about 175 nm to about 275 nm, about 175 nm to about 300 nm, about 175 nm to about 325 nm, about 175 nm to about 350 nm, about 175 nm to about 375 nm, about 175 nm to about 400 nm, about 175 nm to about 500 nm, about 200 nm to about 225 nm, about 200 nm to about 250 nm, about 200 nm to about 275 nm, about 200 nm to about 300 nm, about 200 nm to about 325 nm, about 200 nm to about 350 nm, about 200 nm to about 375 nm, about 200 nm to about 400 nm, about 200 nm to about 500 nm, about 225 nm to about 250 nm, about 225 nm to about 275 nm, about 225 nm to about 300 nm, about 225 nm to about 325 nm, about 225 nm to about 350 nm, about 225 nm to about 375 nm, about 225 nm to about 400 nm, about 225 nm to about 500 nm, about 250 nm to about 275 nm, about 250 nm to about 300 nm, about 250 nm to about 325 nm, about 250 nm to about 350 nm, about 250 nm to about 375 nm, about 250 nm to about 400 nm, about 250 nm to about 500 nm, about 275 nm to about 300 nm, about 275 nm to about 325 nm, about 275 nm to about 350 nm, about 275 nm to about 375 nm, about 275 nm to about 400 nm, about 275 nm to about 500 nm, about 300 nm to about 325 nm, about 300 nm to about 350 nm, about 300 nm to about 375 nm, about 300 nm to about 400 nm, about 300 nm to about 500 nm, about 325 nm to about 350 nm, about 325 nm to about 375 nm, about 325 nm to about 400 nm, about 325 nm to about 500 nm, about 350 nm to about 375 nm, about 350 nm to about 400 nm, about 350 nm to about 500 nm, about 375 nm to about 400 nm, about 375 nm to about 500 nm, or about 400 nm to about 500 nm. In some embodiments, the average center-to-center distance between molecules is about 150 nm, about 175 nm, about 200 nm, about 225 nm, about 250 nm, about 275 nm, about 300 nm, about 325 nm, about 350 nm, about 375 nm, about 400 nm, or about 500 nm. In some embodiments, the average center-to-center distance between molecules is at least about 150 nm, about 175 nm, about 200 nm, about 225 nm, about 250 nm, about 275 nm, about 300 nm, about 325 nm, about 350 nm, about 375 nm, or about 400 nm. In some embodiments, the average center-to-center distance between molecules is at most about 175 nm, about 200 nm, about 225 nm, about 250 nm, about 275 nm, about 300 nm, about 325 nm, about 350 nm, about 375 nm, about 400 nm, or about 500 nm.

Figure 12B:
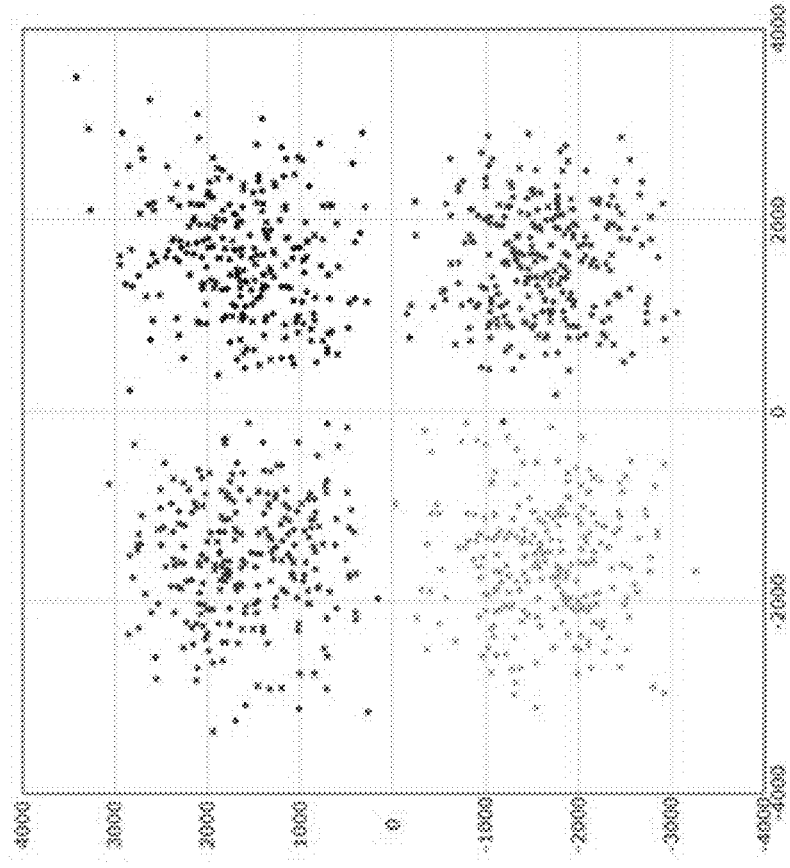
FIG. 12B shows a cross-talk plot of fluorophore intensity between four fluorophores from a 4× oversampled image.
Figure 12A:
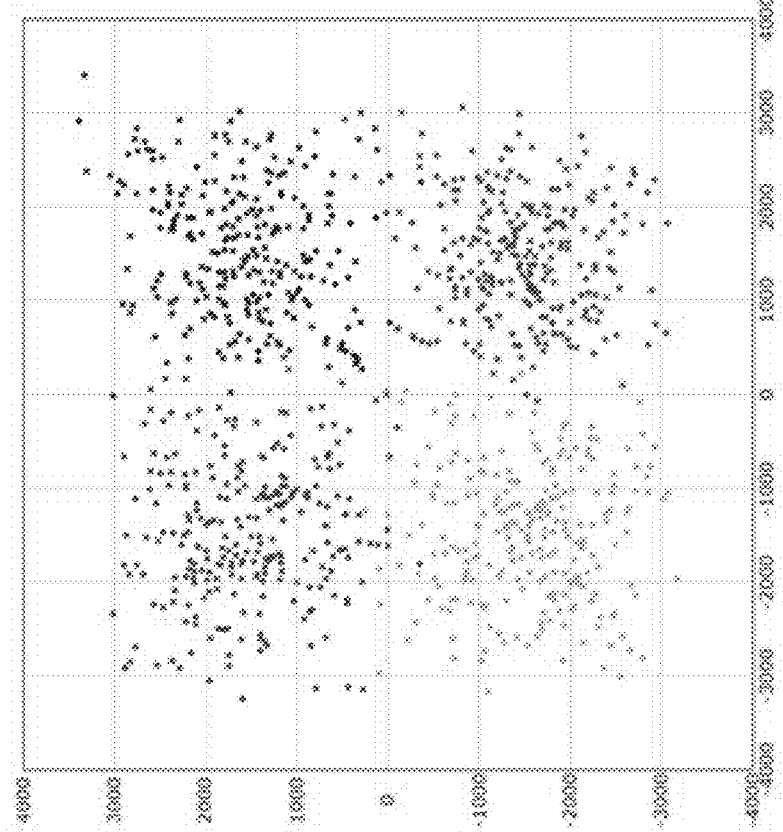
FIG. 12A shows a cross-talk plot of fluorophore intensity between four fluorophores from optical signals detected from the raw image.
Figure 13B:
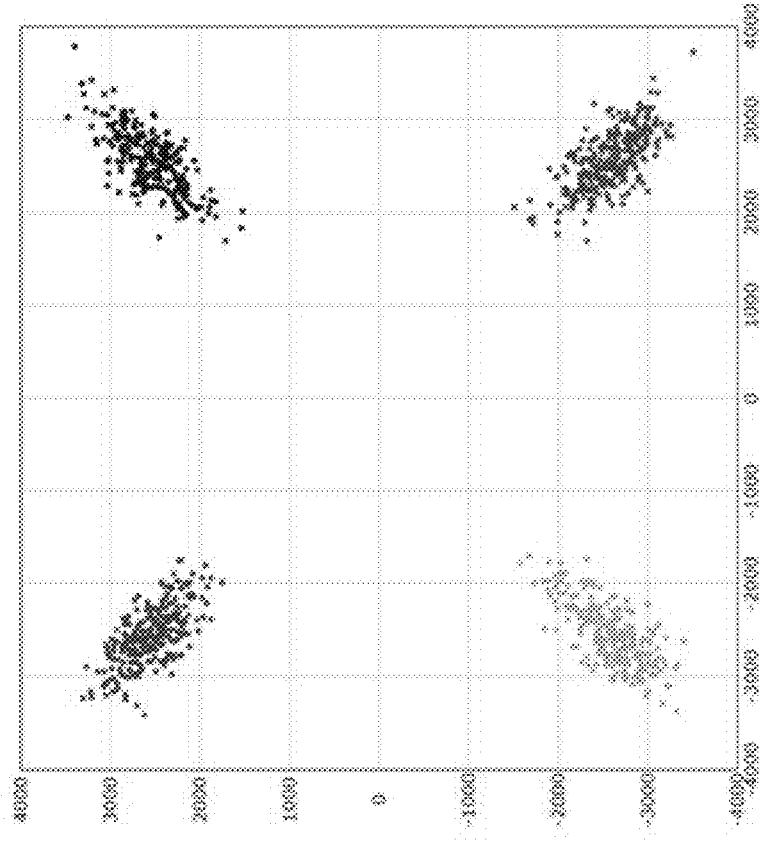
FIG. 13B shows a cross-talk plot of fluorophore intensity between four fluorophores from a 4× oversampled and deconvolved image using a deconvolution algorithm with accurate analyte position information, according to an embodiment of the present disclosure.
Figure 13A:
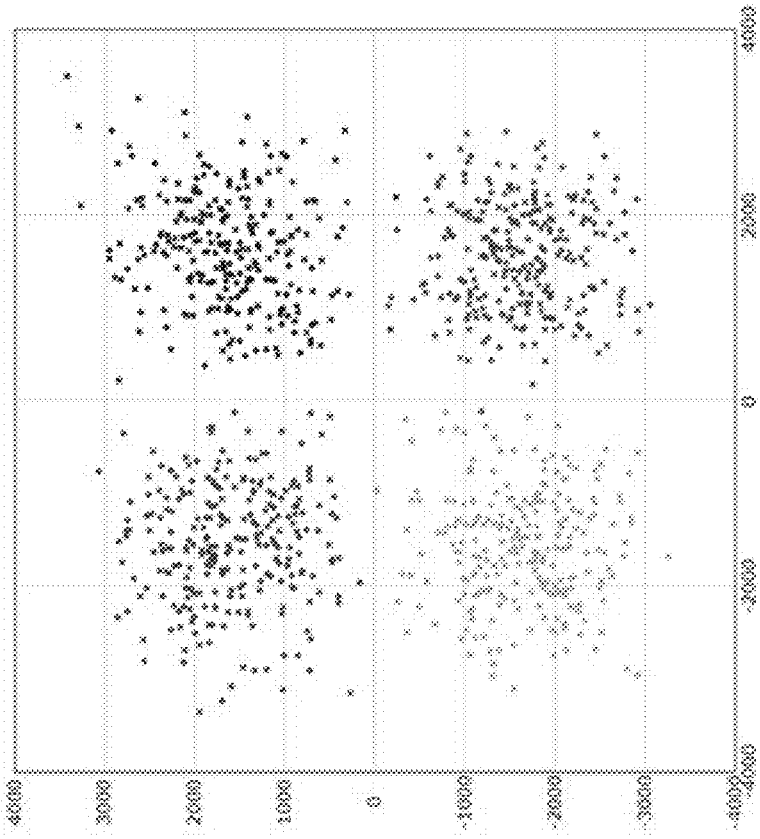
FIG. 13A shows a cross-talk plot of fluorophore intensity between four fluorophores from a 4× oversampled image without deconvolution or nearest neighbor correction.

FIG. 12A shows the cross-talk plot of fluorophore intensity between the four fluorophores from optical signals detected from the raw image. FIG. 12B and FIG. 13A each shows the separation between the four fluorophores achieved by generating a 4× oversampled image, indicating the achievement of some removal of cross-talk at each analyte. FIG. 13B shows a cross-talk plot for the same imaging region but with deconvolution and nearest neighbor regression performed as shown in FIG. 11 and described herein. As compared with FIG. 13A and FIG. 12A, each analyte detected shows clear separation of its optical signal from the other fluorophores, indicating a highly accurate fluorophore identification for each analyte.

Figure 14A:
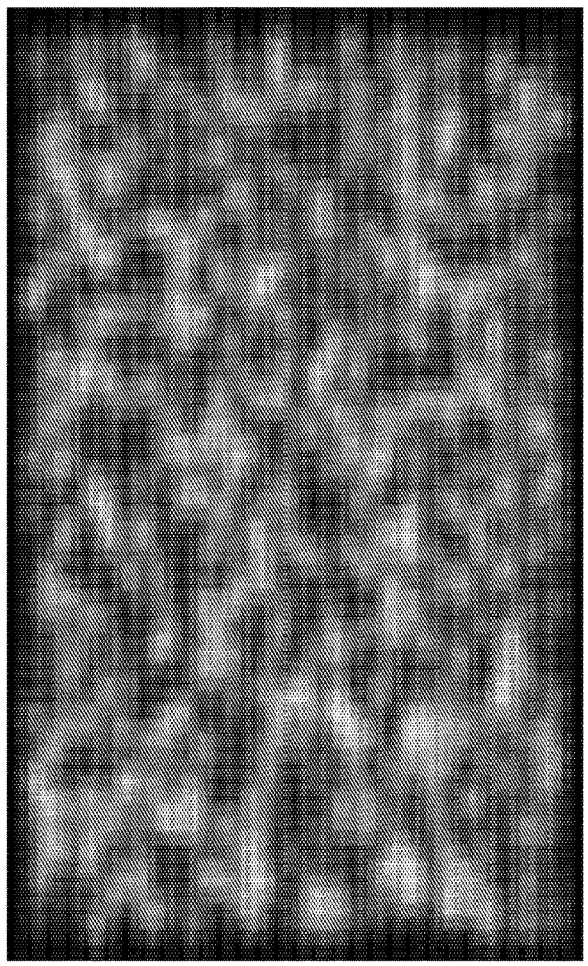
FIG. 14A shows a simulated four-color composite of a raw image of a field at a center-to-center spacing between analytes of about 315 nm.
Figure 14B:
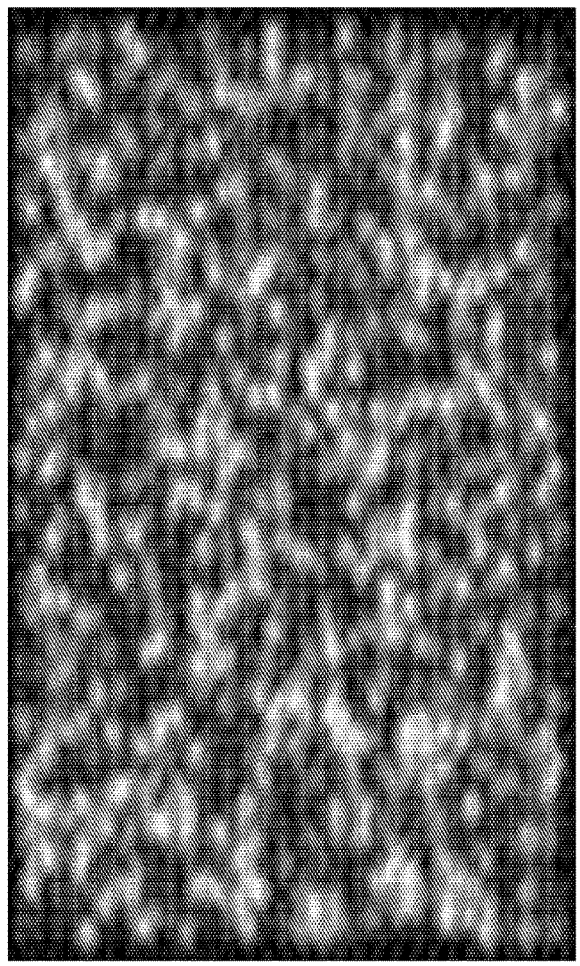
FIG. 14B shows a simulated four-color composite of a deconvolved image at a center-to-center spacing between analytes of about 315 nm.

FIG. 14A and FIG. 14B show a simulated four-color composite of each detected 10.075 μm×10.075 um region as simulated above. This visually represents the clarity between analytes form the raw image (FIG. 14A) and the image processed as described herein (FIG. 14B).

Sequencing

The methods described above and in FIG. 11 also facilitate sequencing by sequencing by synthesis using optical detection of complementary reversible terminators incorporated into a growing complementary strand on a substrate comprising densely packed polynucleotides. Thus, signals correlating with the sequence of neighboring polynucleotides at a center-to-center distance below the diffraction limit can be reliably detected using the methods and optical detection systems described herein. Image processing during sequencing can also include previous cycle regression based on clonal sequences repeated on the substrate or on the basis of the data itself to correct for errors in the sequencing reaction or detection. In some embodiments, the polynucleotides deposited on the substrate for sequencing are concatemers. A concatemer can comprise multiple identical copies of a polynucleotide to be sequenced. Thus, each optical signal identified by the methods and systems described herein can refer to a single detectable label (e.g., a fluorophore) from an incorporated nucleotide, or can refer to multiple detectable labels bound to multiple locations on a single concatemer, such that the signal is an average from multiple locations. The resolution that may occur may not be between individual detectable labels, but between different concatemers deposited to the substrate.

In some embodiments, molecules to be sequenced, single or multiple copies, may be bound to the surface using covalent linkages, by hybridizing to capture oligonucleotide on the surface, or by other non-covalent binding. The bound molecules may remain on the surface for hundreds of cycles and can be re-interrogated with different primer sets, following stripping of the initial sequencing primers, to confirm the presence of specific variants.

In one embodiment, the fluorophores and blocking groups may be removed using chemical reactions.

In another embodiment, the fluorescent and blocking groups may be removed using UV light.

In one embodiment, the molecules to be sequenced may be deposited on reactive surfaces that have 50-100 nM diameters and these areas may be spaced at a pitch of 150-300 nM. These molecules may have barcodes, attached onto them for target deconvolution and a sequencing primer binding region for initiating sequencing. Buffers may contain appropriate amounts of DNA polymerase to enable an extension reaction. These may contain 10-100 copies of the target to be sequenced generated by any of the gene amplification methods available (PCR, whole genome amplification etc.)

In another embodiment, single target molecules, tagged with a barcode and a primer annealing site may be deposited on a 20-50 nM diameter reactive surface spaced with a pitch of 60-150 nM. The molecules may be sequenced individually.

In one embodiment, a primer may bind to the target and may be extended using one dNTP at a time with a single or multiple fluorophore (s); the surface may be imaged, the fluorophore may be removed and washed and the process repeated to generate a second extension. The presence of multiple fluorophores on the same dNTP may enable defining the number of repeats nucleotides present in some regions of the genome (2 to 5 or more).

In a different embodiment, following primer annealing, all four dNTPs with fluorophores and blocked 3' hydroxyl groups may be used in the polymerase extension reaction, the surface may be imaged and the fluorophore and blocking groups removed and the process repeated for multiple cycles.

In another embodiment, the sequences may be inferred based on ligation reactions that anneal specific probes that ligate based on the presence of a specific nucleotides at a given position.

A random array may be used which may have improved densities over prior art random arrays using the techniques outlined above, however random arrays generally have 4× to 10× reduced areal densities of ordered arrays. Advantages of a random array include a uniform, non-patterned surface for the chip and the use of shorter nucleic acid strands because there is no need to rely on the exclusionary properties of longer strands.

Computer Systems

Figure 28:
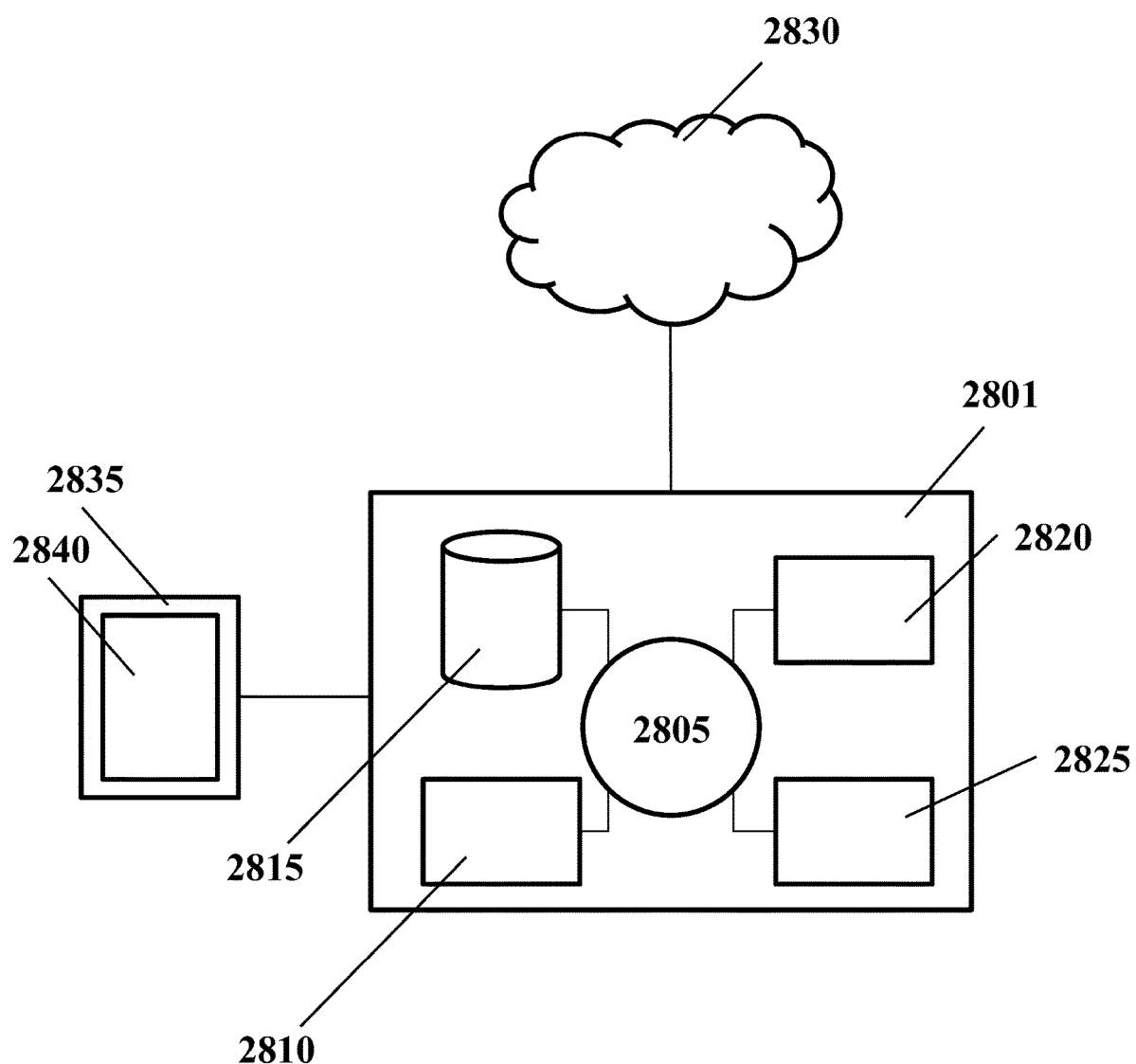
FIG. 28 shows a computer system that is programmed or otherwise configured to implement methods provided herein.

The present disclosure provides computer systems that are programmed to implement methods of the disclosure. FIG. 28 shows a computer system 2801 that is programmed or otherwise configured to direct the methods described herein and utilize the systems described herein. The computer system 2801 can regulate various aspects of the present disclosure, such as, for example, directing the cycles of probe binding described herein. The computer system 2801 can be an electronic device of a user or a computer system that is remotely located with respect to the electronic device. The electronic device can be a mobile electronic device.

The computer system 2801 includes a central processing unit (CPU, also "processor" and "computer processor" herein) 2805, which can be a single core or multi core processor, or a plurality of processors for parallel processing. The computer system 2801 also includes memory or memory location 2810 (e.g., random-access memory, read-only memory, flash memory), electronic storage unit 2815 (e.g., hard disk), communication interface 2820 (e.g., network adapter) for communicating with one or more other systems, and peripheral devices 2825, such as cache, other memory, data storage and/or electronic display adapters. The memory 2810, storage unit 2815, interface 2820 and peripheral devices 2825 are in communication with the CPU 2805 through a communication bus (solid lines), such as a motherboard. The storage unit 2815 can be a data storage unit (or data repository) for storing data. The computer system 2801 can be operatively coupled to a computer network ("network") 2830 with the aid of the communication interface 2820. The network 2830 can be the Internet, an internet and/or extranet, or an intranet and/or extranet that is in communication with the Internet. The network 2830 in some cases is a telecommunication and/or data network. The network 2830 can include one or more computer servers, which can enable distributed computing, such as cloud computing. The network 2830, in some cases with the aid of the computer system 2801, can implement a peer-to-peer network, which may enable devices coupled to the computer system 2801 to behave as a client or a server.

The CPU 2805 can execute a sequence of machine-readable instructions, which can be embodied in a program or software. The instructions may be stored in a memory location, such as the memory 2810. The instructions can be directed to the CPU 2805, which can subsequently program or otherwise configure the CPU 2805 to implement methods of the present disclosure. Examples of operations performed by the CPU 2805 can include fetch, decode, execute, and writeback.

The CPU 2805 can be part of a circuit, such as an integrated circuit. One or more other components of the system 2801 can be included in the circuit. In some cases, the circuit is an application specific integrated circuit (ASIC).

The storage unit 2815 can store files, such as drivers, libraries and saved programs. The storage unit 2815 can store user data, e.g., user preferences and user programs. The computer system 2801 in some cases can include one or more additional data storage units that are external to the computer system 2801, such as located on a remote server that is in communication with the computer system 2801 through an intranet or the Internet.

The computer system 2801 can communicate with one or more remote computer systems through the network 2830. For instance, the computer system 2801 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2801 via the network 2830.

Methods as described herein can be implemented by way of machine (e.g., computer processor) executable code stored on an electronic storage location of the computer system 2801, such as, for example, on the memory 2810 or electronic storage unit 2815. The machine executable or machine readable code can be provided in the form of software. During use, the code can be executed by the processor 2805. In some cases, the code can be retrieved from the storage unit 2815 and stored on the memory 2810 for ready access by the processor 2805. In some situations, the electronic storage unit 2815 can be precluded, and machine-executable instructions are stored on memory 2810.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 2801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2801 can include or be in communication with an electronic display 2835 that comprises a user interface (UI) 2840 for providing, for example, the detectable signal sequences mentioned herein or the identification of analytes as mentioned herein or the location of analytes as disclosed herein or any other information disclosed herein. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 2805. The algorithm can, for example, direct the optical modules disclosed herein to capture an image or direct probe binding.

Equivalents and Scope

Those skilled in the art will recognize, or be able to ascertain using no more than routine experimentation, many equivalents to the specific embodiments in accordance with the present disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the present disclosure, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

EXAMPLES

Section and table headings are not intended to be limiting.

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present disclosure may employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pennsylvania: Mack Publishing Company, 1990); Carey and Sundberg Advanced Organic Chemistry 3rd Ed. (Plenum Press) Vols A and B (1992).

Example 1: Dense Packing of Molecules

Methods below will describe how to utilize a square ordered array where the pitch ranges between 200 nm and 333 nm. Additional methods will be described that allow even smaller pitches. An imaging system is described in International Application PCT/US2018/020737, filed Mar. 2, 2018 and incorporated herein by reference, which will be used as a reference system which enables sub-diffraction limit imaging. The optical system can include multiple 2,048 by 2,048 pixel cameras operating up to 100 Hz frames per second (fps) with field size 332.8 um by 332.8 um. This system is capable of measuring as little as a single fluor at and above 90 fps. Using this system with 1-10 copies (or 1-10 fluorophores) per molecule at 85 fps achieves the necessary throughput to image a 63 mm×63 mm slide in under 15 minutes. Biochemistry cycles and imaging are continuously and simultaneously performed, either by using two chips or by dividing a single chip into at least 2 regions.

Example 2: Single-Molecule Sequencing Using Sequencing by Synthesis

Single-molecule sequencing using sequencing-by-synthesis approach was evaluated on the Apton System. To test the methodology, single-stranded DNA templates with 5' phosphate group were first attached to the chip with a tecarbohydrazide activated silicon surface of the flow cell through EDC (1-Ethyl-3-(3-mplate dimethylaminopropyl)carbodiimide) chemistry. The sequencing primer was the annealed the target deposited on the surface. The sequencing templates used in our initial studies included synthetic oligonucleotide containing EGFR L858R, EGFR T790M, and BRAF V600E mutations and two cDNA samples reversed transcribed from ERCC 00013 and ERCC 00171 control RNA transcripts. After DNA template immobilization and primer annealing, the flow cell is loaded on the Apton instrument for sequencing reactions, which involves multiple cycles of enzymatic single nucleotide incorporation reaction, imaging to detect fluorescence dye detection, followed by chemical cleavage. Terminator IX DNA Polymerase from NEB was used for single base extension reaction, which is a 9° NTM DNA Polymerase variant with an enhanced ability to incorporate modified dideoxynucleotides. Four dNTPs used in the reaction are labeled with 4 different cleavable fluorescent dyes and blocked at 3'-OH group with a cleavable moiety (dCTP-AF488, dATP-AFCy3, dTTP-TexRed, and dGTP-Cy5 from MyChem). During each sequencing reaction cycle, a single labeled dNTP is incorporated and the reaction is terminated because of the 3'-blocking group on dNTP. After dNTP incorporation, the unincorporated nucleotides are removed from the flow-cell by washing and the incorporated fluorescent dye labeled nucleotide is imaged to identify the base. After the images are captured, the fluorescent dye and blocking moiety are cleaved from the incorporated nucleotide using 100 mM TCEP ((tris(2-carboxyethyl)phosphine), pH9.0), allowing subsequent addition of the next complementary nucleotide in next cycle. This extension, detection and cleavage cycle is then repeated to increase the read length.

Figure 15A:
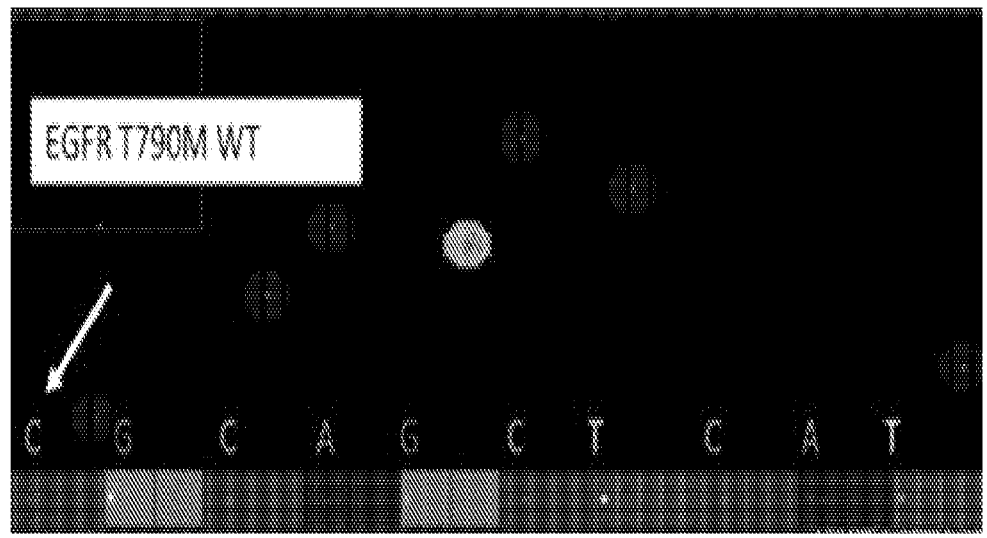
FIG. 15A shows results of sequencing of a 1:1 mixture of synthetic oligonucleotide templates corresponding to the region around codon 790 in the EGFR gene containing equal amounts of mutant and wild type (WT) targets.
Figure 15A:
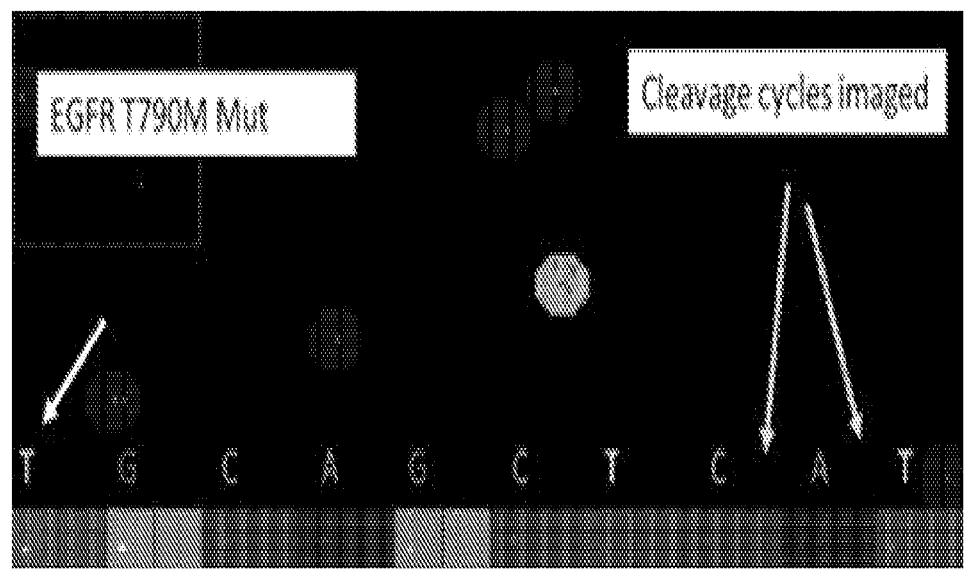

FIG. 15A shows results of sequencing of a 1:1 mixture of synthetic oligonucleotide templates corresponding to the region around codon 790 in the EGFR gene containing equal amounts of mutant and wild type (WT) targets. Images from incorporation of dye labeled nucleotides used to sequence synthetic templates corresponding to a region of the EGFR gene near codon 790 with a mutation at the first base (C-incorporation in WT & T-incorporation in mutant) after the primer. The montage in FIG. 15A depicts images from alternating base incorporation and cleavage cycles. This data exhibits the ability of the system to detect 10 cycles of base incorporation. Arrows indicate the base change observed.

The synthetic oligonucleotides used were around 60 nucleotides long. A primer that had a sequence ending one base prior to the mutation in codon 790 was used to enable the extension n reaction. The surface was imaged post incorporation of nucleotides by the DNA polymerase and after the cleavage reaction with TCEP. The yellow circle indicates the location of the template molecule that was aligned using data from 10 consecutive cycles of dye incorporation. Molecules were identified with known color incorporation sequences, following that the actual base incorporations are identified by visual inspections which is labor—intensive.

Figure 15B:
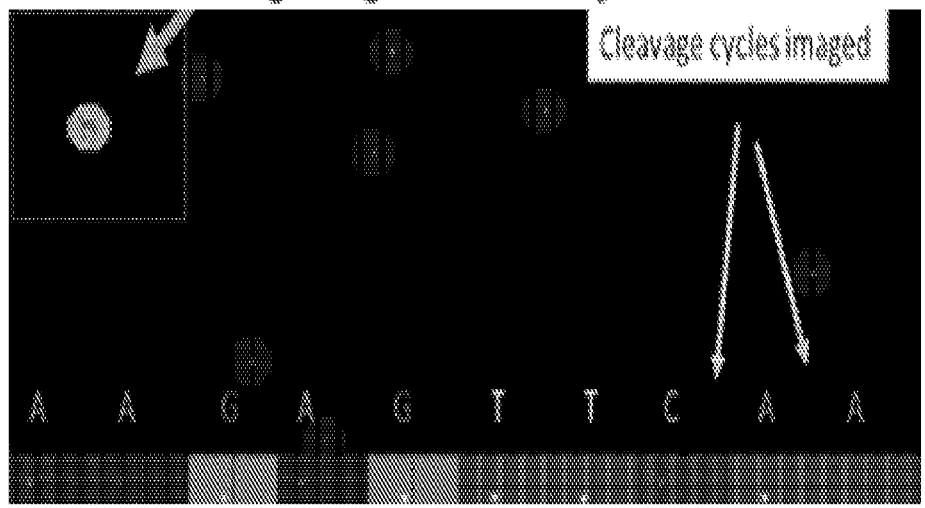
FIG. 15B depicts images from alternating base incorporation and cleavage cycles.
Figure 15B:
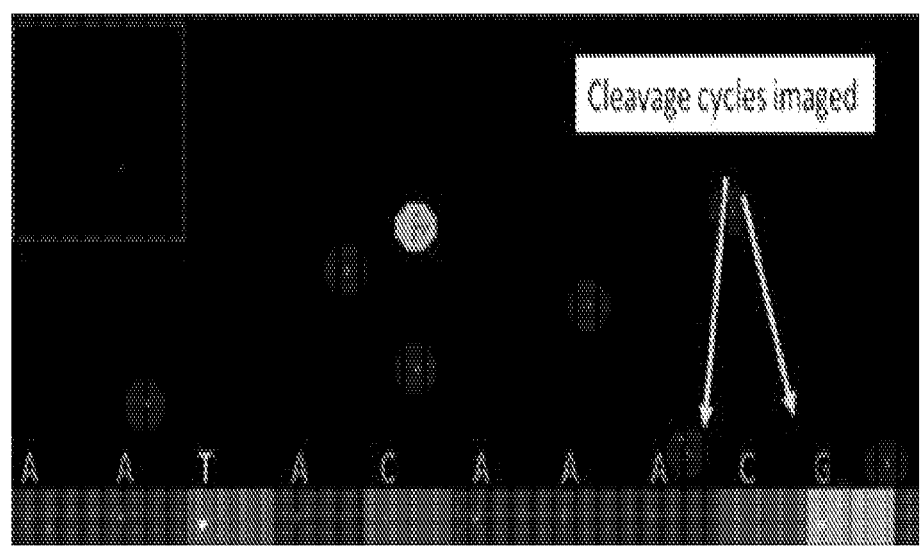

Dye labeled nucleotides were used to sequence cDNA generated from RNA templates. RNA used was generated by T7 transcription from cloned ERCC control plasmids. FIG. 15B depicts images from alternating base incorporation and cleavage cycles. The data exhibits the ability of the system to detect 10 cycles of base incorporation. The sequence observed were correct. Yellow arrows indicate the cleavage cycles.

Figure 16:
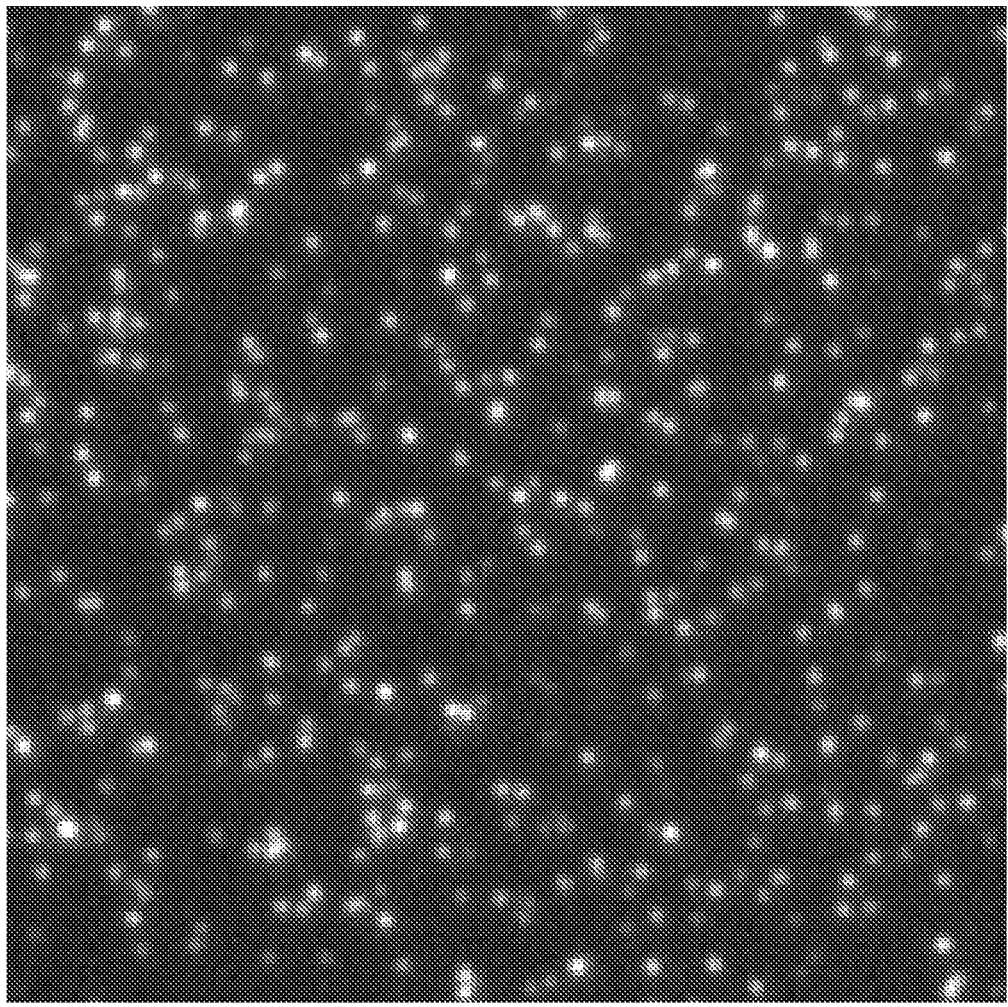
FIG. 16 is an image of single analytes deposited on a substrate and bound by a probe comprising a fluorophore.

Specifically, cDNA templates corresponding to transcripts generated from the ERCC (External RNA Controls Consortium) control plasmids by T7 transcription were sequenced. The cDNA molecule generated were >350 nucleotides long. The surface was imaged post incorporation of nucleotides by the DNA polymerase and after the cleavage reaction with TCEP. The yellow circle in FIG. 15B indicates the location of the template molecule that was aligned using data from 10 consecutive cycles of dye incorporation. Data indicated ability to manually detect 10 cycles of nucleotide incorporation by manual viewing of images Example 3: Relative Location Determination for Analyte Variants FIG. 16 is an image of single molecules deposited on a substrate and bound by a probe comprising a fluorophore. The molecules are anti-ERK antibodies bound to ERK protein from cell lysate which has been covalently attached to the solid support. The antibodies are labeled with 3-5 fluorophores per molecule. Similar images are attainable with single fluor nucleic acid targets, e.g., during sequencing by synthesis.

Figure 17:
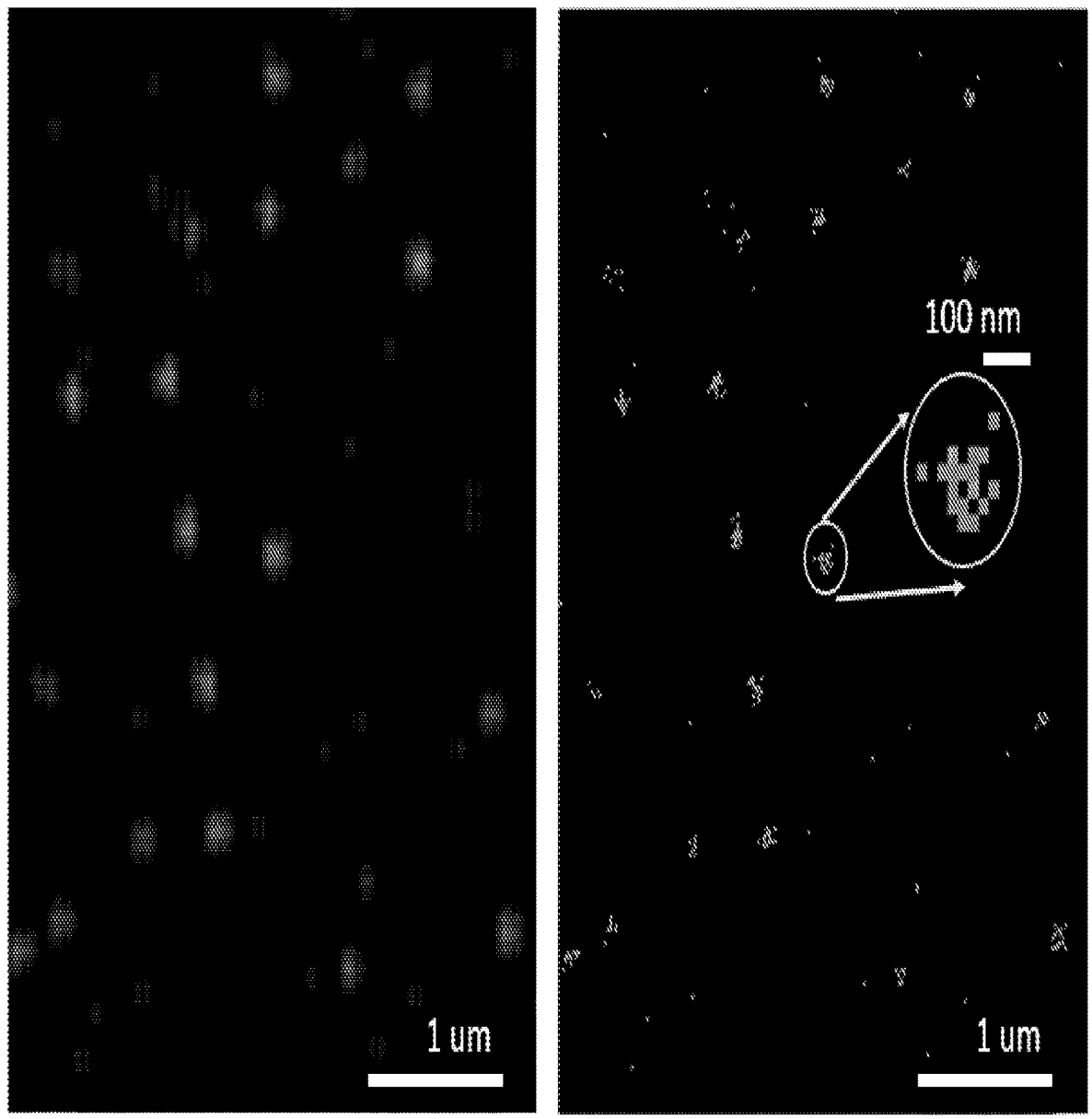
FIG. 17, right panel, shows peaks from oversampled images of a field from each cycle overlaid from several analytes on a substrate (clusters of peaks). The left panel is the smoothed version of the right panel, recapitulating a Gaussian distribution of peaks from an analyte across a plurality of cycles with a highly accurate peak indicating relative positional information.
Figure 18:
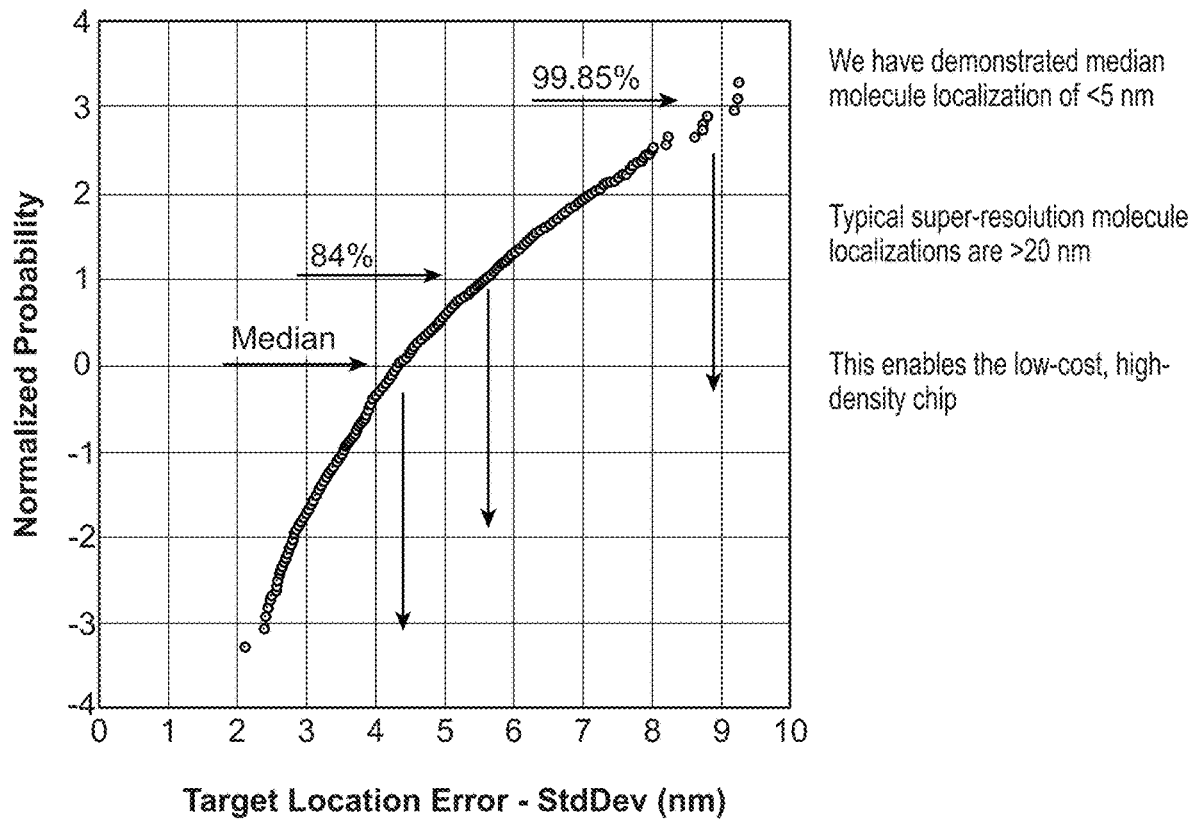
FIG. 18 shows localization variation for each of a plurality of molecules found in a field. The median localization variance is 5 nm and the 3 sigma localization variance is under 10 nm.

To improve accuracy of detection, the molecules undergo successive cycles of probe binding and stripping, in this case 30 cycles. In each round, the image is processed to determine the location of the molecules. The images are background subtracted, oversampled by 2×, after which peaks are identified. Multiple layers of cycles are overlaid on a 20 nm grid. The location variance is the standard deviation, or the radius divided by the square root of the number of measurements. FIG. 17, right panel, shows each peak from each cycle overlaid. The left panel is the smoothed version of the right panel. Each bright spot represents a molecule. The molecule locations are resolvable with molecule-to-molecule distances under 200 nm. FIG. 18 shows localization variation for each of a plurality of molecules found in a field. The median localization variance is 5 nm and the 3 sigma localization variance is under 10 nm.

Example 4: Densely-Packed Sequencing Substrates and Single-Sided Density

Figure 23A:
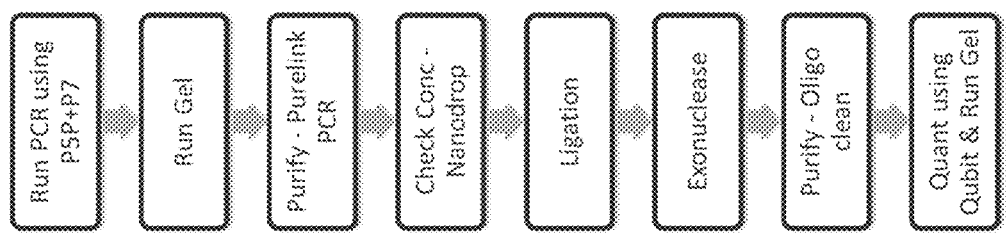
FIG. 23A shows a flow chart to form a library of circularized DNA comprising target sequences from a sample, according to an embodiment of the present disclosure.

Single-Stranded Circle Formation:

To prepare a library of concatemers comprising target sequences to distribute on the surface of a substrate in a randomly distributed close-packed layer, a sample comprising target sequences was amplified, purified, ligated to form circularized DNA, and quantified, as shown in FIG. 23A.

Amplification of Targets

An Illumina MiSeq library was purchased from SeqMatic (Fremont, CA) made with the standard protocol using *E. coli* DNA purchased from Affymetrix (Santa Clara, CA—PN 14380)

The library was amplified by PCR amplification. Each PCR reaction included the following components listed in Table 1:

TABLE 1

|  | One 50 ul Reaction (uL) |
|---|---|
| 10× Pfx Amplification buffer | 10 |
| 10 mM dNTP (Invitrogen) | 1.5 |
| 50 mM MgSO4 (stored at 4° C.) | 1 |
| Primer mix (1004) | 1.5 |
| Template DNA | 1-5 |
| Platinum Pfx DNA Polymerase (Invitrogen-ThermoFisher) | 0.4 |
| Pfx Enhancer (Invitrogen-ThermoFisher) | 2.5 |
| Water | Fill with water to 50 ul_, |

The primer mix is a 50:50 mix of P5-Phosphate (/5Phos/AAT GAT ACG GCG ACC ACC GA (SEQ ID NO: 1)) and P7 (CAA GCA GAA GAC GGC ATA CGA GAT (SEQ ID NO:2)) primers at 10 uM:

The PCR amplification was performed under the following conditions: 5 mM at 94° C. followed by 35 cycles of: 94° C., 15 sec; 55° C., 30 sec; and 68° C., 30 sec. An aliquot of the amplification product was run on a 2% gel to verify the library molecule size (300-500 base pairs in this instance). The PCR amplification product was then purified using a PureLink® Spin Column (Thermofisher) according to the manufacturer's protocol.

Circularization of Target DNA

The purified PCR amplification products were then subject to single strand circularization by ligation in the reaction mix described in Table 2:

TABLE 2

|  | Single reaction (uL) |
|---|---|
| 10× HiFi Taq DNA Ligase Buffer | 5 |
| DNA template (104) | 10 |
| Bridging oligonucleotide (100 uM) | 1 |
| HiFi Taq DNA Ligase (New England Biolabs, Ipswich, MA) | 1 |
| H2O | 33 |
| Total vol (at) | 50 |

The bridging oligonucleotide sequence was TCG GTG GTC GCC GTA TCA TTC AAG CAG AAG ACG GCA TAC GAG AT (SEQ ID NO: 3).

The ligation was performed under the following conditions: 30 sec at 95° C. followed by 40 cycles of: 95° C., 15 sec; 55° C., 2 min; and 62° C., 3 min.

After ligation, 14 each of Exonuclease I and Exonuclease III (New England Biolabs) were added and the reaction is incubated for an additional 45 min at 37° C. and 30 min at 85° C. The resulting material was purified using a Zymo-Spin™ Column (Oligo Clean & Concentrator™ kit Zymo Research, Irvine, CA) using the manufacturer's protocol. After purification, the concentration was measured using a Qubit 2.0 fluorometer (ThermoFisher) and Quant-iT Oli-Green® (ThermoFisher) with custom calibration samples using an oligonucleotide of known concentration.

Concatamer Formation from Circularized DNA

Concatemers from circularized DNA comprising the target sequence were formed in a reaction mix described in Table 3:

TABLE 3

|  | volume | buffer | Additional components |
|---|---|---|---|
| circular template | 10 μL | water |  |
| primer solution | 5 μL | 3× reaction buffer |  |
| Enzyme mix | 5 μL | 1× reaction buffer | 2 U/ul Phi29 DNA polymerase |

TABLE 3-continued

|  | volume | buffer | Additional components |
|---|---|---|---|
|  |  |  | 2 mM in each dNTP 0.004 U/uL iPPase (all from New England Biolabs, Ipswich, MA) |
| Reaction inactivation buffer | 5 μL | 0.25M EDTA, pH 8.0 (Sigma-Aldrich, St. Louis, MO) |  |

The primer solution was a 750 nM suspension of the primer (ATC TCG TAT GCC GTC TTC TGC TTG (SEQ ID NO: 4)) in 3× reaction buffer. The 10× reaction buffer was: 500 mM Tris-HCl, 100 mM (NH4)2SO4, 40 mM DTT, 100 mM MgCl2, pH 7.5 @ 25° C.

The circular template+primer mix was incubated for 10 mM at 90° C., and then 30 min at 30° C. A pre-warmed enzyme mix was then added as in Table 3 for 90 mM. The reaction was stopped with the addition of reaction inactivation buffer and stored at 4° C.

Figure 23B:
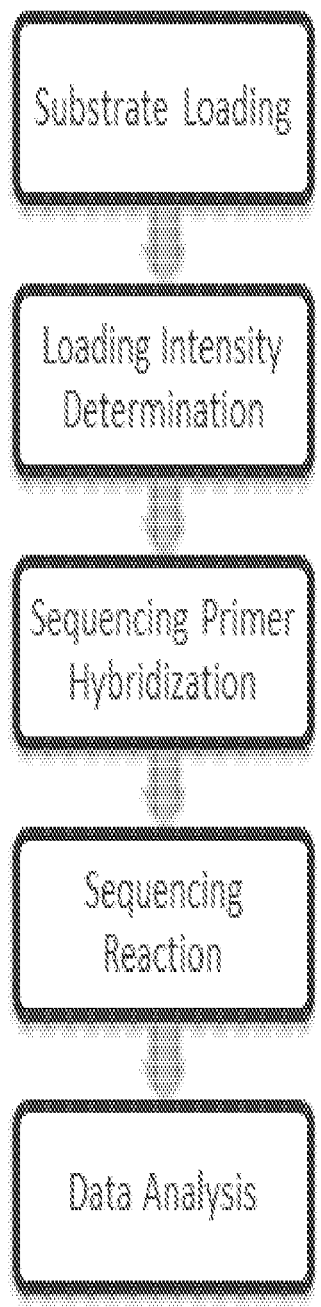
FIG. 23B shows a flow chart to load concatemers on a layer on a substrate and to sequence the concatemers, according to an embodiment of the present disclosure.

Concatemer libraries were then layered on a substrate to form a densely-packed, randomly distributed layer bound to the surface of a substrate, followed by sequencing the bound concatemers via imaging and image processing, and analysis of the data, as shown in FIG. 23B and as described below.

One microliter of the sequencing substrate was mixed with 19 ul of citrate phosphate buffer, and 10 ul was loaded onto a custom biochip and incubated overnight. The chip was then washed 2× with citrate phosphate buffer, 2× with potassium phosphate buffer and 2× with NA wash 3 buffer.

Figure 25A:
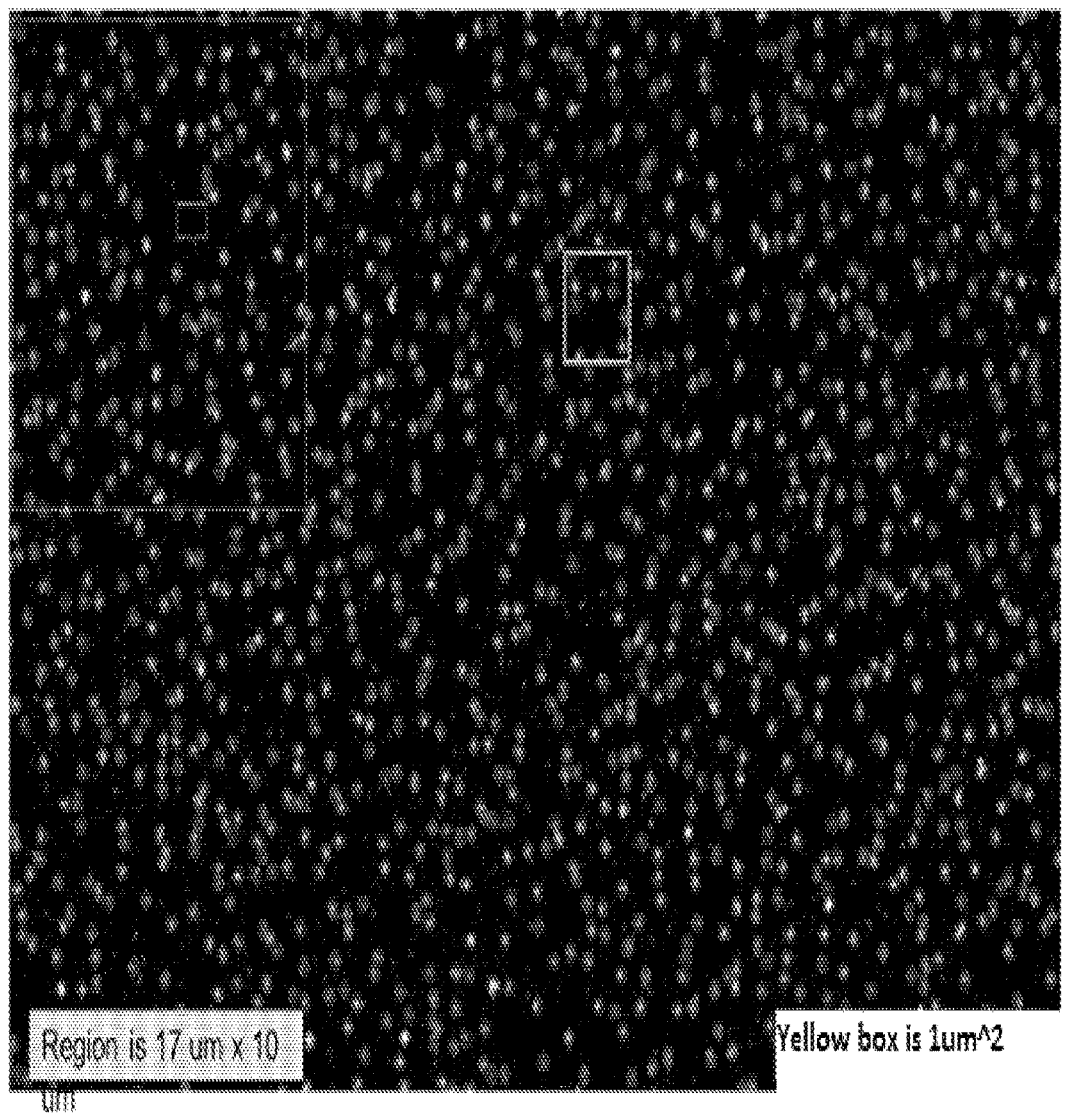
FIGS. 25A-25C show images of concatemer layers distributed at high density on the surface of a substrate, according to some embodiments of the present disclosure.
Figure 25B:
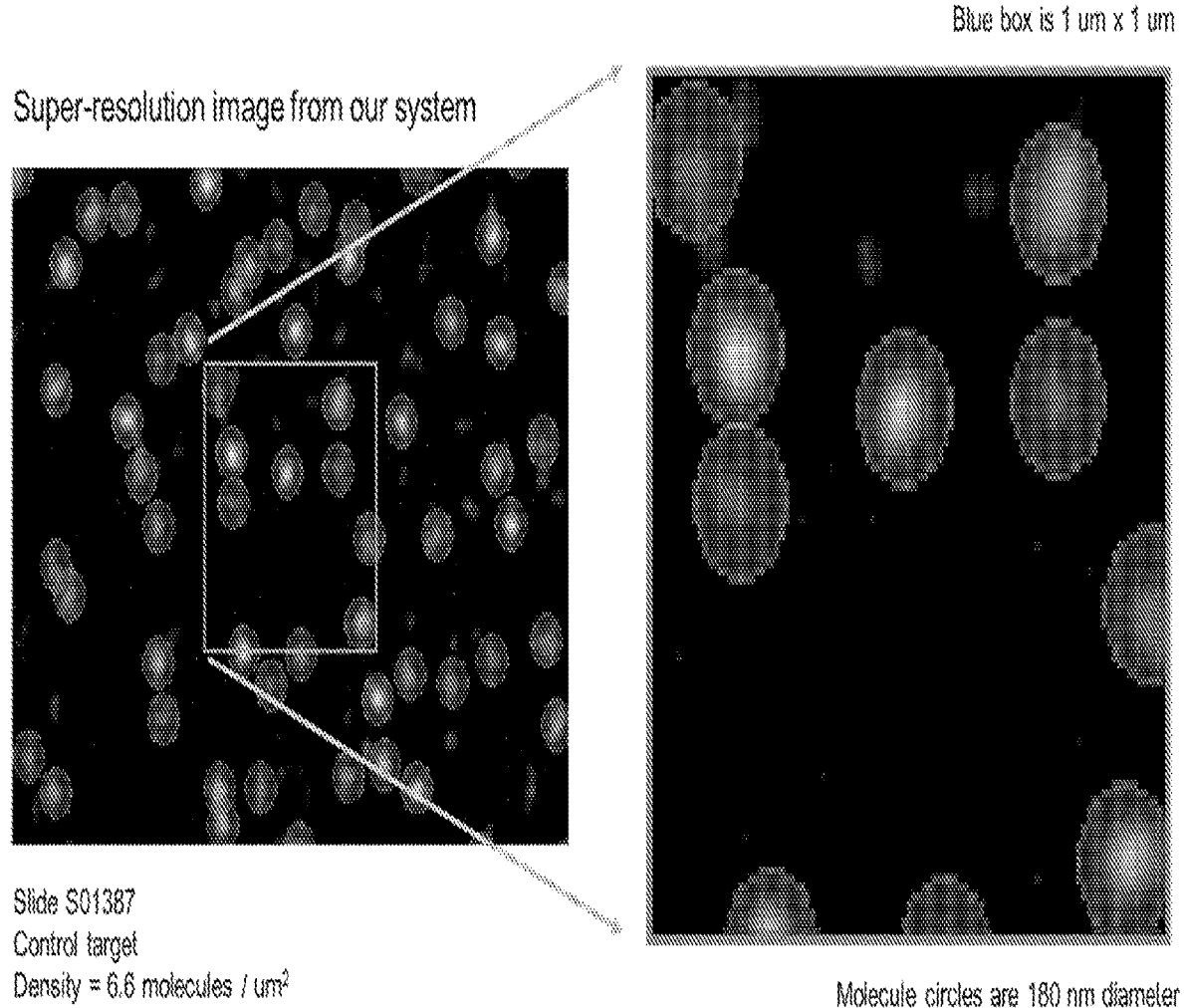
Figure 25C:
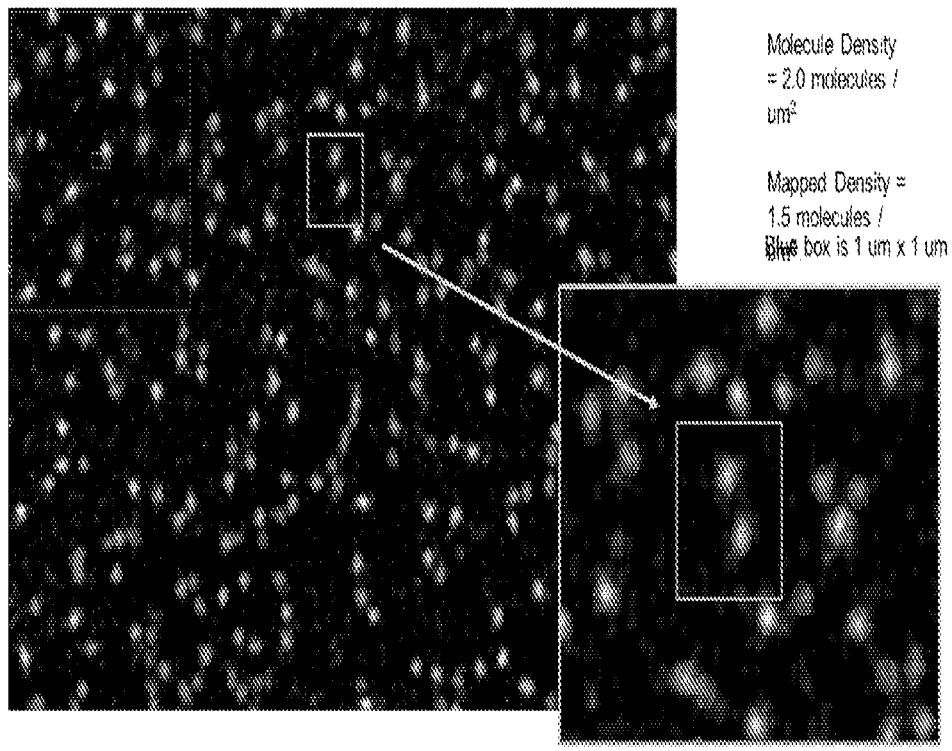
Figure 25D:
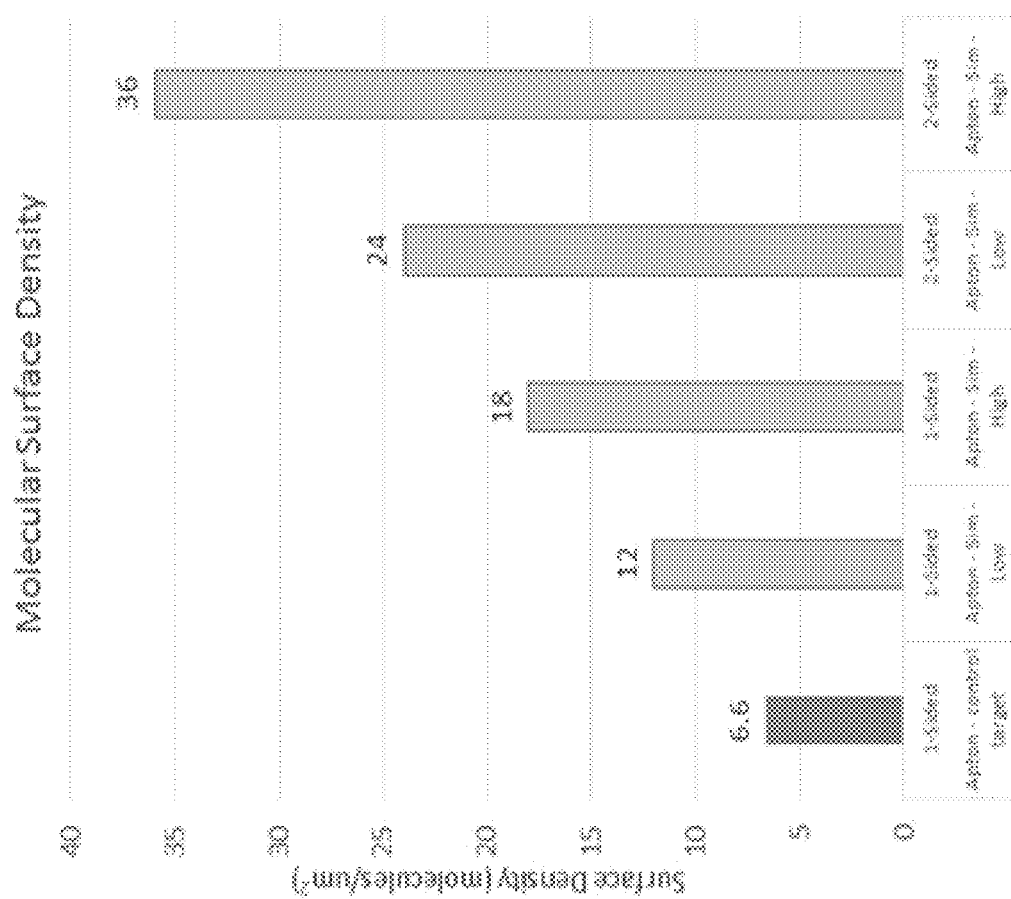
FIG. 25D depicts a graph of concatemer surface density, according to some embodiments of the present disclosure.
Figure 26A:
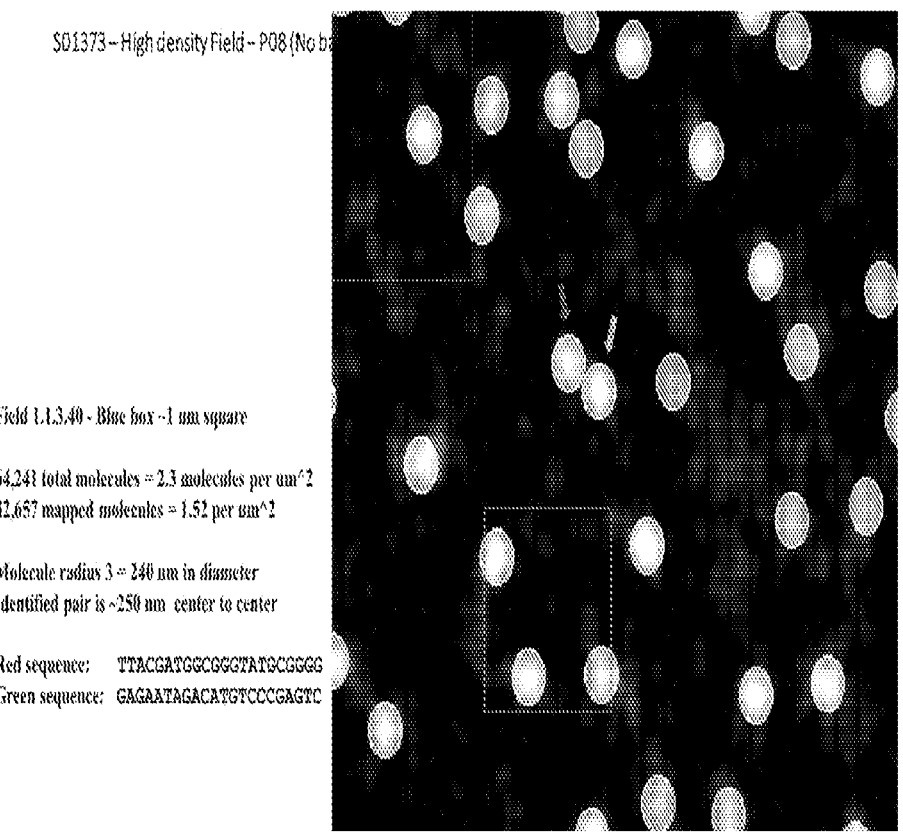
FIGS. 26A-26D depicts images of concatemers bound to a substrate used for sequencing a concatemer target, showing successful resolution of sequences (e.g. SEQ ID NOs: 6-13) between adjacent nearby concatemers.
Figure 26B:
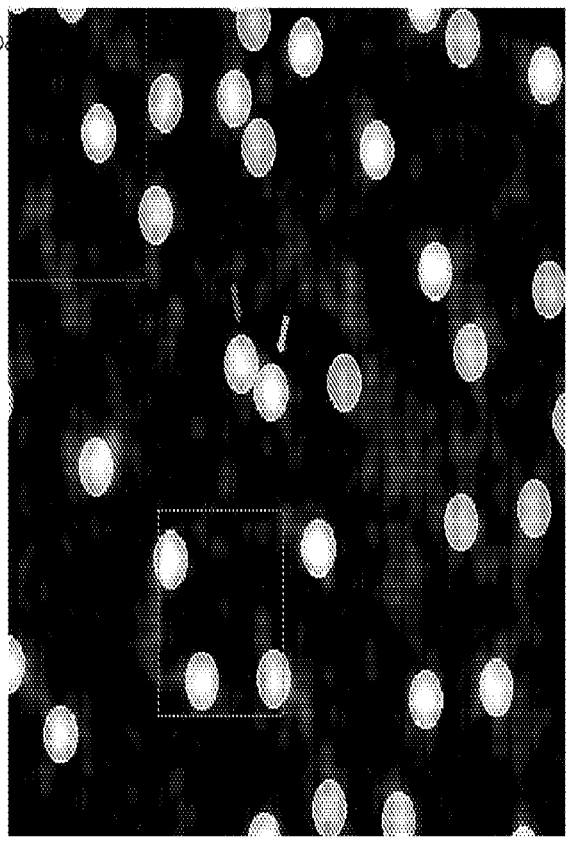
Figure 26C:
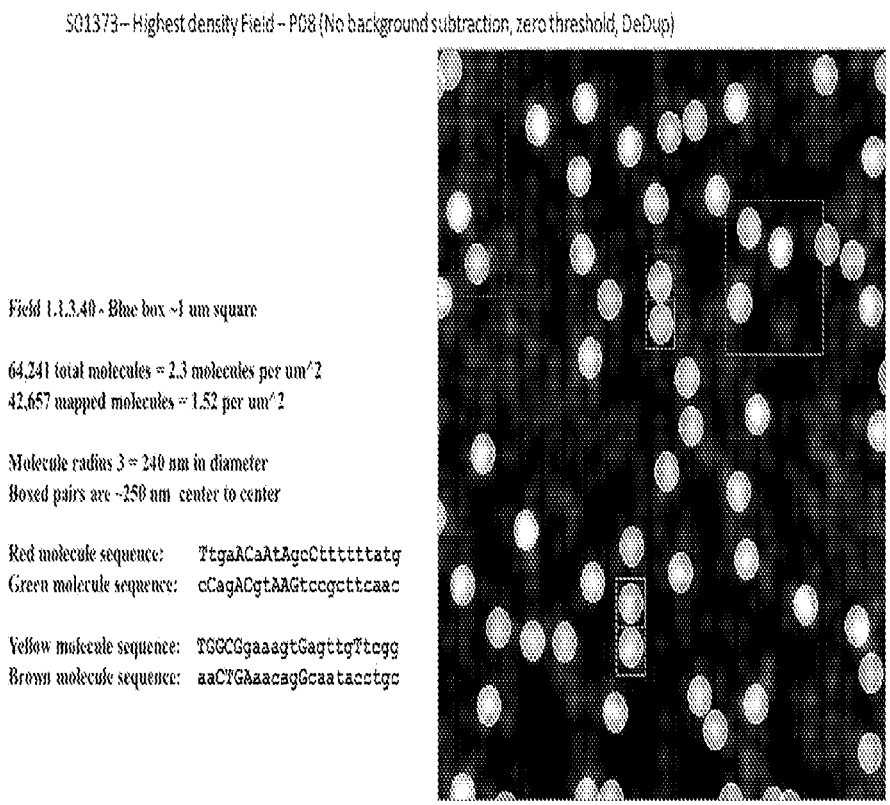
Figure 26D:
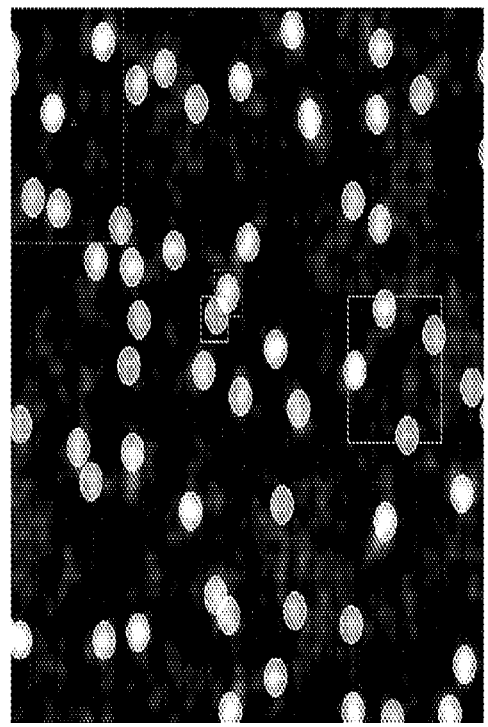

Fluorescent probe was bound to the concatemer layer bound to the surface of the chip to determine identity. Images showing the density are shown in FIGS. 25A-25C. FIG. 25D shows a plot of measured density of a 1-sided concatemer layer according to methods described herein (Apton—control target) and simulated distributions at higher densities (Apton—Sim).

Example 5: Sequencing *E. Coli* Reads

Imaging/Sequencing

Sequencing by synthesis was performed using standard sequencing chemistries. The chip comprising the densely packed concatemer layer was loaded into the AptonBio Sequencer and washed 6×5 mM at 60° C. with Wash1 (20 mM Tris-HCl, 10 mM (NH4)2 SO4, 10 mM KCl, 2 mM MgSo4, 0.1% 100, pH 8.8 @25° C., 50 mM NaCl). The sequencing oligo (ATC TCG TAT GCC GTC TTC TGC TTG (SEQ ID NO:4)) was diluted to 100 nM in hybridization buffer and incubated 1×1 mM followed by 2×10 mM at 60° C. with Wash1 washes between hybridization operations. Then thirty-two cycles of the following 8 operations were performed:

1—Cleavage: 225 sec at 60° C. with buffer in Table 4

TABLE 4

|  | Amount | Concentration (Working) |
|---|---|---|
| TCEP [add vendor] | 31.53 mg | 100 mM |
| ION NaOH | 40 uL |  |
| 5M Nacl | 11 uL | 50 mM |
| 1M Tris-HCL | 11 | ~1M |
| Total Volume | 1100 |  |

2—Wash: 240 sec at 30° C. in Phosphate buffer pH 8.
3—Imaging: Wash2 (20 mM Tris-HCl, 5 mM Ascorbic Acid (pH 8.8)
4—Wash: Wash1 at 60° C.
5—Extension: 450 sec at 60° C. with buffer in Table 5

TABLE 5

| | Concentration (Stock) | Concentration (Working) | Vol/reaction (μL) |
|---|---|---|---|
| ThermoPol Reaction Buffer (NEB) | 10× | 1× | 5 |
| dATP labeled reversible terminator (MyChem, LLC, San Diego) | 5 μM | 0.1 uM | 1 |
| dGTP labeled reversible terminator (MyChem, LLC, San Diego) | 5 uM | 0.1 uM | 1 |
| dTTP labeled reversible terminator (MyChem, LLC, San Diego) | 5 μM | 0.1 uM | 1 |
| dCTP labeled reversible terminator (MyChem, LLC, San Diego) | 5 uM | 0.1 uM | 1 |
| NaCl | 5M | 0.05M | 0.5 |
| Therminator X (New England Biolabs Ipswich, MA) | 10 U/μL | 0.05 U | 1.25 |
| Non-labeled dNTP Mix (MyChem, LLC, San Diego) | 10 uM | 0 to 1 uM | 0-5 |
| Water | | | 38.75-34.24 |
| Total | | | 50 |

6—Wash: Wash1 at 30° C.
7—Wash: 2 min at 30° C. in Phosphate buffer pH8.
8—Imaging: Wash 2.

Figure 27A:
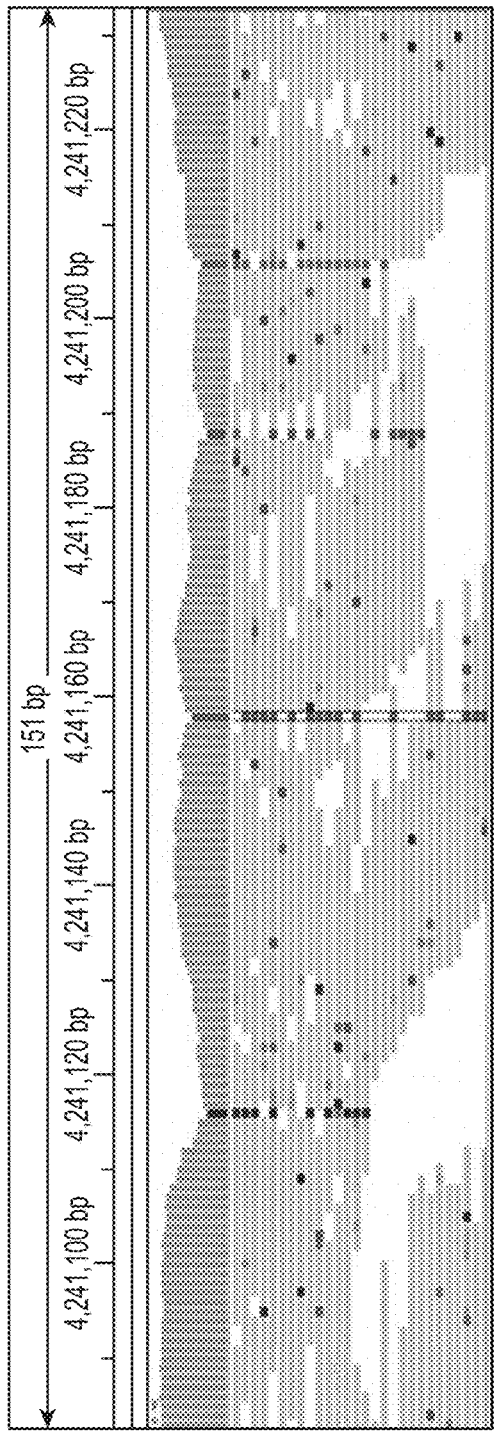
FIGS. 27A-27C show the results of sequencing by synthesis of *E. coli* using the methods and systems described herein.
Figure 27B:
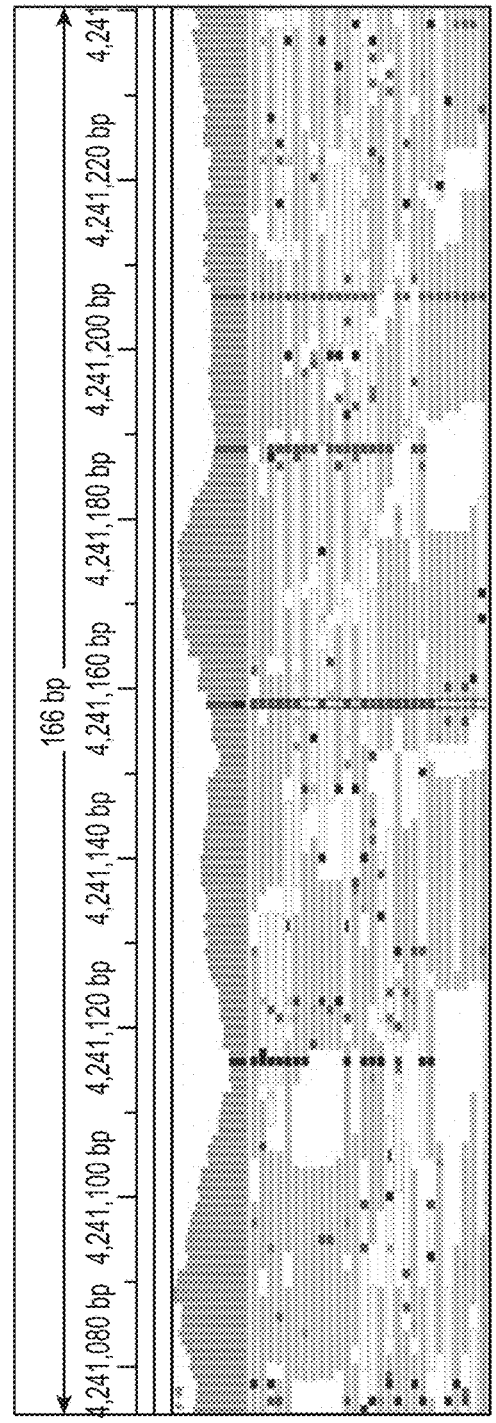

Results:
Reads of 30-40 bp are shown in FIG. 27A. Reads of 20-25 bp are shown in FIG. 27B.

Figure 27C:
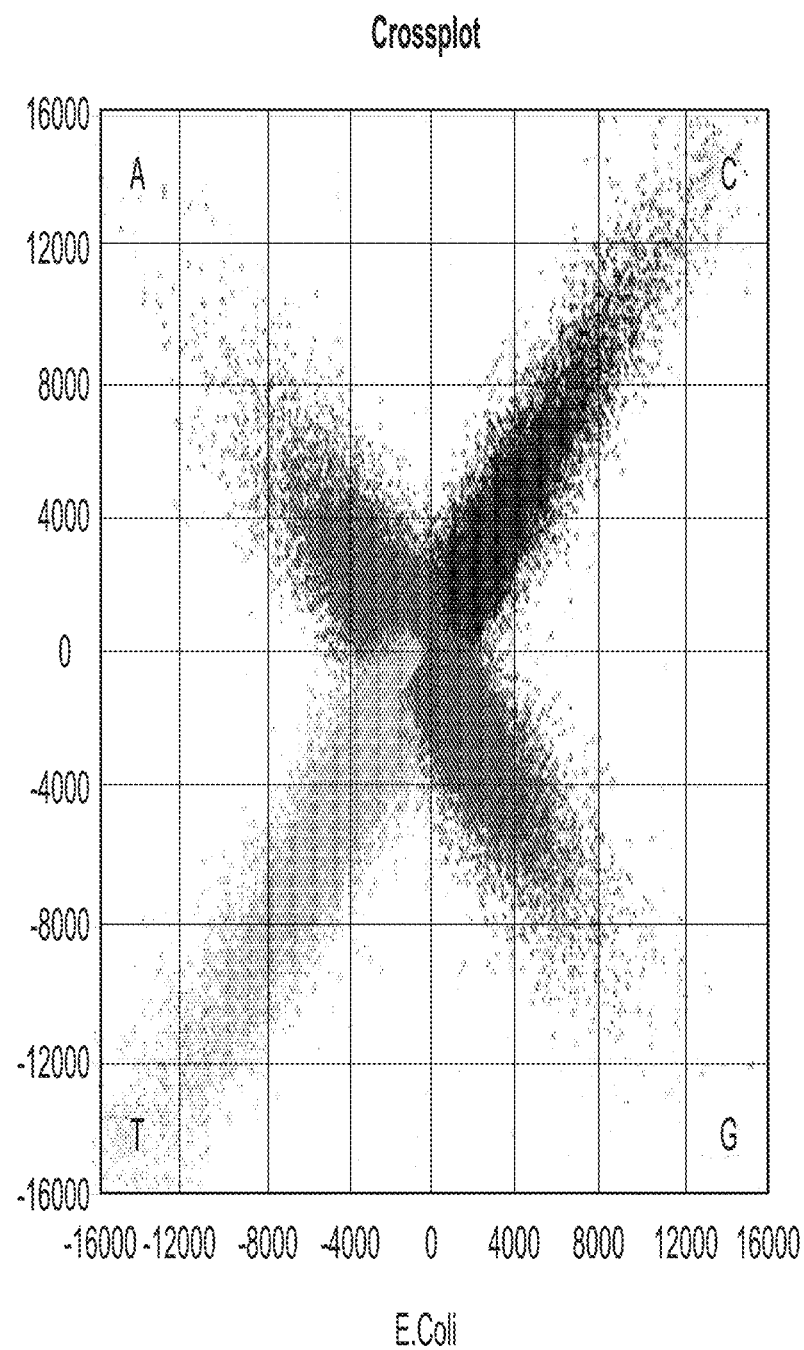

Crossplots shown in FIG. 27C show the resolution of base calling at individual spots for $E.\ coli$ sequencing.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed:

1. A method of sequencing a plurality of analytes disposed at high density on a surface of a substrate, comprising:
(a) performing a plurality of cycles of probe binding to a substrate comprising a surface, wherein said surface comprises a plurality of analytes immobilized adjacent to said surface, wherein at least two analytes of said plurality of analytes have a center-to-center distance of less than about 500 nanometers (nm), wherein a cycle of said plurality of cycles comprises:
(i) contacting said plurality of analytes with a plurality of probes, wherein a probe of said plurality of probes comprises a detectable label;
(ii) imaging a field of said surface with an optical system to detect an optical signal from each probe of said plurality of probes brought in contact with said plurality of analytes, thereby detecting a plurality of optical signals in said field for said cycle;
(b) determining a peak location of an analyte of said plurality of analytes from each of said plurality of optical signals by applying an optical distribution model to one or more overlaid optical signals of said plurality of optical signals; and
(c) identifying said analyte from said detectable label of said plurality of probes at said peak location across said plurality of cycles.

2. The method of claim 1, wherein said plurality of optical signals is overlapping.

3. The method of claim 1, further comprising overlaying said peak location of each optical signal of said plurality of optical signals to determine a relative position of each detected probe on said surface.

4. The method of claim 3, further comprising resolving said optical signals in each image of said field using said determined relative position and a resolving function.

5. The method of claim 4, wherein said resolving function comprises deconvolution.

6. The method of claim 1, wherein said plurality of analytes comprises a plurality of DNA concatemers.

7. The method of claim 1, wherein said plurality of analytes comprises proteins or peptides.

8. The method of claim 1, wherein said plurality of analytes is immobilized on said surface at an average density of more than 3 molecules per square micron.

9. The method of claim 1, wherein said center-to-center distance is due to, at least in part, a hydrophobic interaction between one or more adjacent analytes and an analyte of said plurality of analytes.

10. The method of claim 9, wherein said hydrophobic interaction is due to zwitterionic features of said plurality of analytes.

11. The method of claim 9, wherein said hydrophobic interaction is due to a repellant or attractive substance provided to said plurality of analytes.

* * * * *

SEQUENCE LISTING

```
Sequence total quantity: 13
SEQ ID NO: 1                moltype = DNA  length = 20
FEATURE                     Location/Qualifiers
source                      1..20
                            mol_type = other DNA
                            organism = synthetic construct
SEQUENCE: 1
aatgatacgg cgaccaccga                                                    20

SEQ ID NO: 2                moltype = DNA  length = 24
FEATURE                     Location/Qualifiers
source                      1..24
                            mol_type = other DNA
                            organism = synthetic construct
SEQUENCE: 2
caagcagaag acggcatacg agat                                               24

SEQ ID NO: 3                moltype = DNA  length = 44
FEATURE                     Location/Qualifiers
source                      1..44
                            mol_type = other DNA
                            organism = synthetic construct
SEQUENCE: 3
tcggtggtcg ccgtatcatt caagcagaag acggcatacg agat                         44

SEQ ID NO: 4                moltype = DNA  length = 24
FEATURE                     Location/Qualifiers
source                      1..24
                            mol_type = other DNA
                            organism = synthetic construct
SEQUENCE: 4
atctcgtatg ccgtcttctg cttg                                               24

SEQ ID NO: 5                moltype =      length =
SEQUENCE: 5
000

SEQ ID NO: 6                moltype = DNA  length = 22
FEATURE                     Location/Qualifiers
source                      1..22
                            mol_type = other DNA
```

-continued

```
                        organism = synthetic construct
SEQUENCE: 6
ttacgatggc gggtatgcgg gg                                                  22

SEQ ID NO: 7            moltype = DNA   length = 22
FEATURE                 Location/Qualifiers
source                  1..22
                        mol_type = other DNA
                        organism = synthetic construct
SEQUENCE: 7
gagaatagac atgtcccgag tc                                                  22

SEQ ID NO: 8            moltype = DNA   length = 22
FEATURE                 Location/Qualifiers
source                  1..22
                        mol_type = other DNA
                        organism = synthetic construct
SEQUENCE: 8
ttgaacaata gcctttttta tg                                                  22

SEQ ID NO: 9            moltype = DNA   length = 22
FEATURE                 Location/Qualifiers
source                  1..22
                        mol_type = other DNA
                        organism = synthetic construct
SEQUENCE: 9
ccagacgtaa gtccgcttca ac                                                  22

SEQ ID NO: 10           moltype = DNA   length = 22
FEATURE                 Location/Qualifiers
source                  1..22
                        mol_type = other DNA
                        organism = synthetic construct
SEQUENCE: 10
tggcggaaag tgagttgttc gg                                                  22

SEQ ID NO: 11           moltype = DNA   length = 22
FEATURE                 Location/Qualifiers
source                  1..22
                        mol_type = other DNA
                        organism = synthetic construct
SEQUENCE: 11
aactgaaaca ggcaatacct gc                                                  22

SEQ ID NO: 12           moltype = DNA   length = 22
FEATURE                 Location/Qualifiers
source                  1..22
                        mol_type = other DNA
                        organism = synthetic construct
SEQUENCE: 12
tataatctta ttctggtact aa                                                  22

SEQ ID NO: 13           moltype = DNA   length = 22
FEATURE                 Location/Qualifiers
source                  1..22
                        mol_type = other DNA
                        organism = synthetic construct
SEQUENCE: 13
ccgactccga cctgggtatt gt                                                  22
```